United States Patent
Qi et al.

(10) Patent No.: US 11,731,967 B2
(45) Date of Patent: Aug. 22, 2023

(54) INHIBITORS OF TRIM33 AND METHODS OF USE

(71) Applicant: Dana-Farber Cancer Institute, Inc., Boston, MA (US)

(72) Inventors: Jun Qi, Sharon, MA (US); Cheng-kui Pei, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 3 days.

(21) Appl. No.: 16/604,030

(22) PCT Filed: Apr. 27, 2018

(86) PCT No.: PCT/US2018/029850
§ 371 (c)(1),
(2) Date: Oct. 9, 2019

(87) PCT Pub. No.: WO2018/200988
PCT Pub. Date: Nov. 1, 2018

(65) Prior Publication Data
US 2020/0255422 A1    Aug. 13, 2020

Related U.S. Application Data

(60) Provisional application No. 62/491,817, filed on Apr. 28, 2017.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS

2003/0018032 A1   1/2003   Gerlach et al.

FOREIGN PATENT DOCUMENTS

| WO | 0127111 A1 | 4/2001 | |
| WO | WO-2008016648 A2 * | 2/2008 | ........... C07D 471/04 |
| WO | 2010116302 A1 | 10/2010 | |
| WO | 2012016133 A2 | 2/2012 | |
| WO | 2013019469 A1 | 2/2013 | |
| WO | 2015013635 A2 | 1/2015 | |
| WO | 20160201370 A1 | 12/2016 | |
| WO | 2017178992 A1 | 10/2017 | |
| WO | 2019070943 A1 | 4/2019 | |

OTHER PUBLICATIONS

Reutlinger et al. Mol. Inf. 2013, 32, 133-138.*
Registry No. 1243447-18-8, File Registry on STN, Sep. 28, 2010.*
Registry No. 314745-91-0, File Registry on STN, Jan. 18, 2001.*
Registry No. 1200800-55-0, File Registry on STN, Jan. 6, 2010.*
Mugherli, L. et al., "In Situ Assembly and Screening of Enzyme Inhibitors with Surface-Tension Microarrays", Angewandte Chemie, 2009, 121(41):7775-7780.
Shi, X., et al., "Loss of TRIM33 causes resistance to BET bromodomain inhibitors through MYC-and TGF-B-dependent mechanisms," 2016, PNAS, E4558-E4566.

* cited by examiner

*Primary Examiner* — Rebecca L Anderson
(74) *Attorney, Agent, or Firm* — Burns & Levinson, LLP; Daniel W. Clarke; Shawn P. Foley

(57) ABSTRACT

The application relates to a compound of Formula (I):

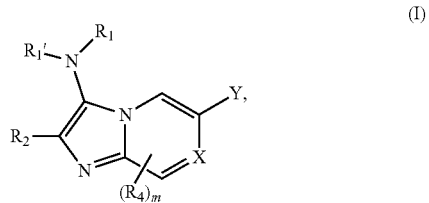

which modulates the activity of TRIM33, a pharmaceutical composition comprising the compound, and a method of treating or preventing a disease in which TRIM33 plays a role.

5 Claims, 52 Drawing Sheets

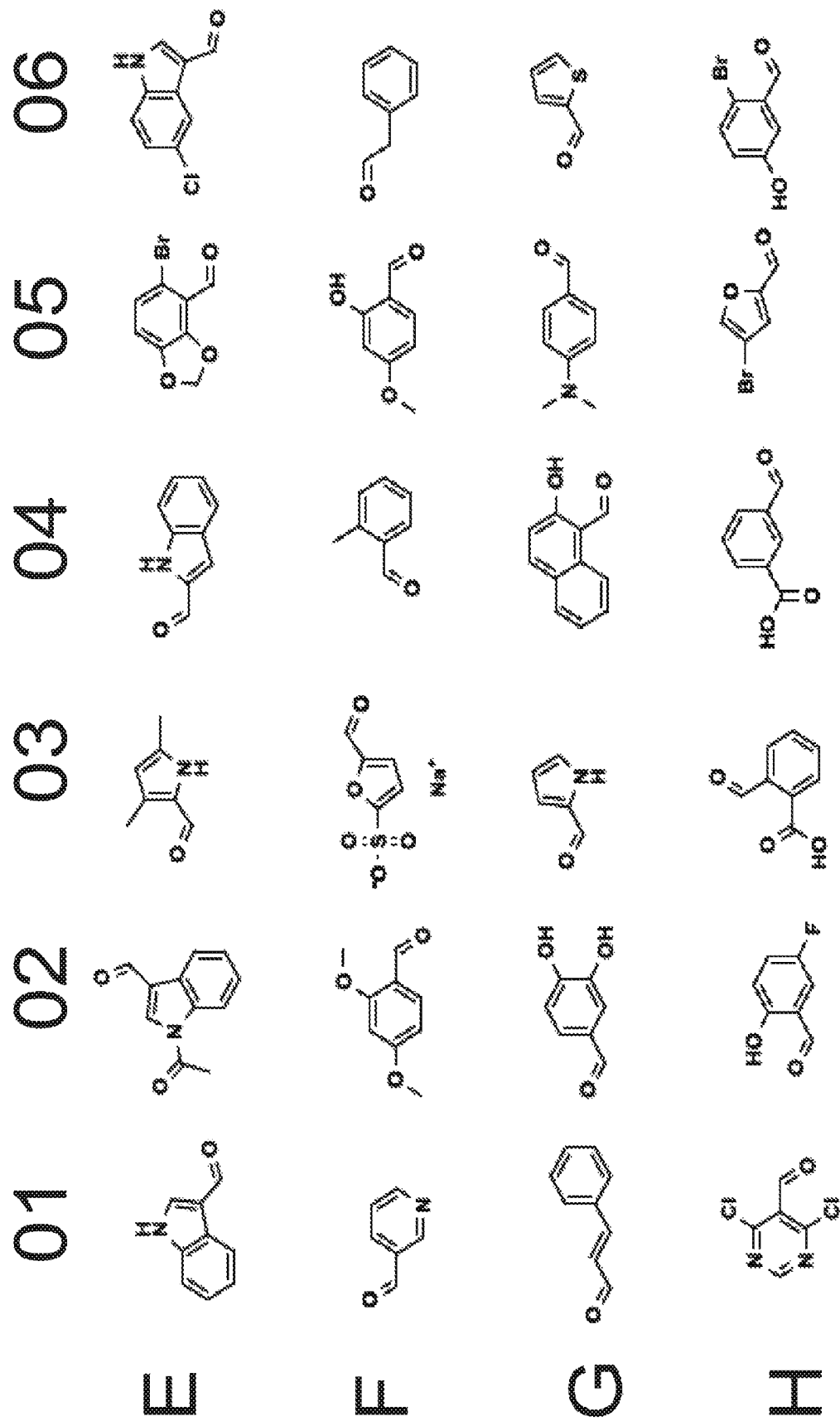

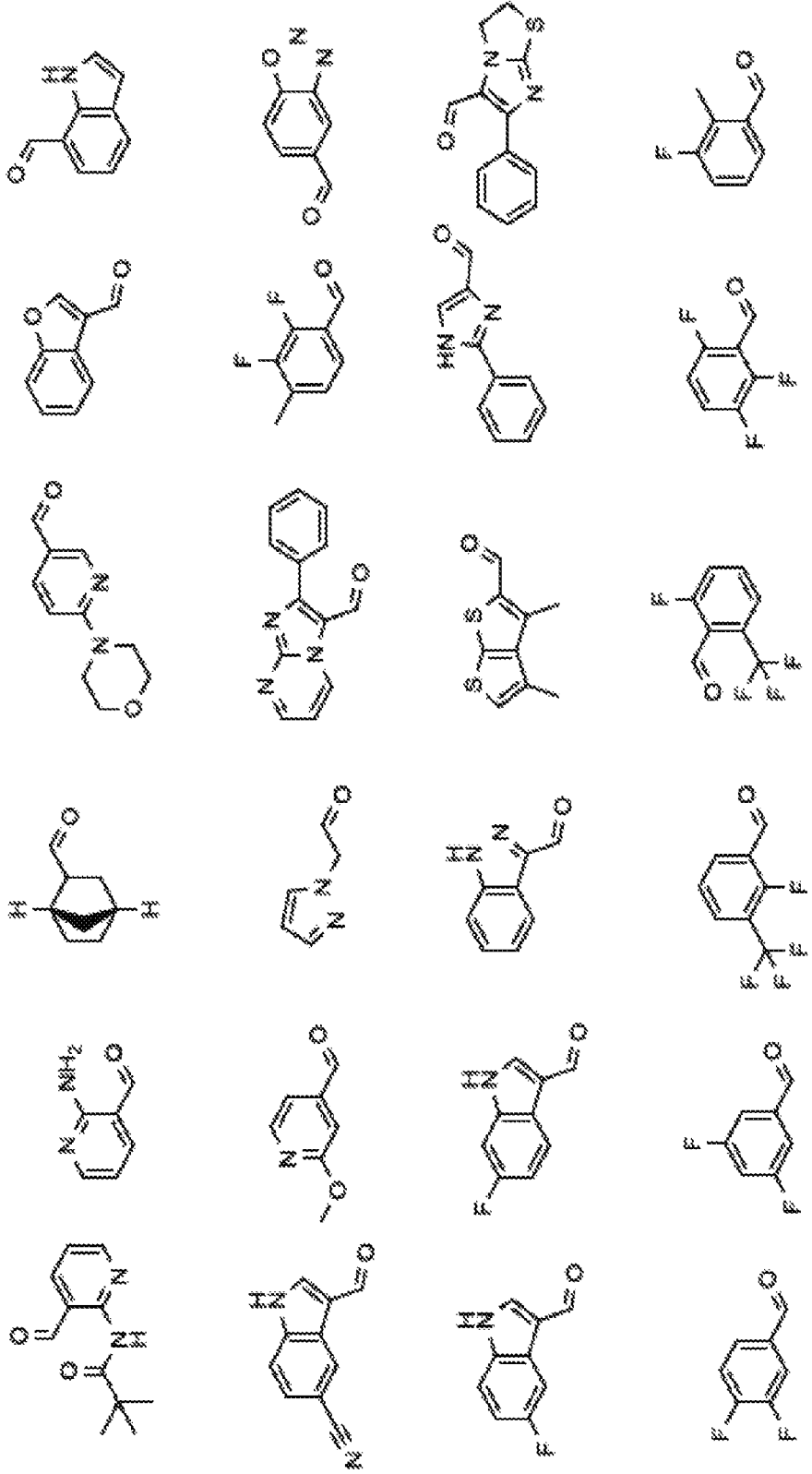

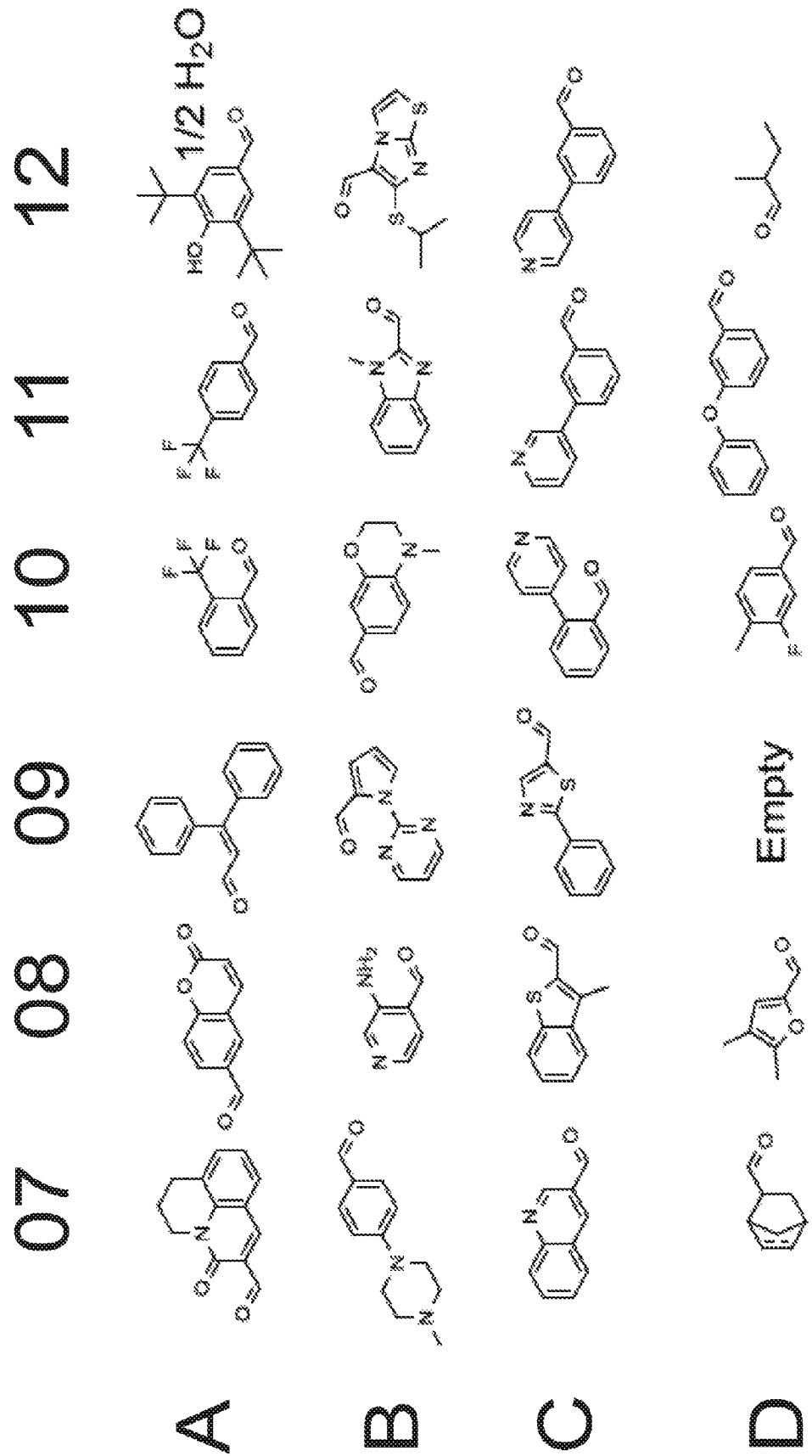

INHIBITORS OF TRIM33 AND METHODS OF USE

REFERENCE TO RELATED APPLICATIONS

This application is a U.S. National Phase application, filed under 35 U.S.C. § 371, of International Application No. PCT/US2018/029850, filed on Apr. 27, 2018, which claims the benefit of and priority to U.S. Provisional Application No. 62/491,817, filed on Apr. 28, 2017, the entire contents of each of which are incorporated herein by reference in their entireties.

BACKGROUND

Tripartite motif-containing protein 33 (TRIM33; also known as TIF1γ, RFG7, PTC7 and Ectodermin) is a multifunctional protein that is a key regulator of embryonic and adult hematopoiesis in vertebrates, facilitates efficient DNA repair, regulates mitosis, controls transcription elongation, and inhibits carcinogenesis. TRIM33 has been implicated in transforming growth factor-β (TGF-β) signalling, by binding to phosphorylated SMAD2/3 or monoubiquitylating SMAD4. TRIM33 has also been shown to act as a tumour suppressor in hepatocellular carcinoma, human chronic myelomonocytic leukemia, and pancreatic cancer.

Therapeutic targeting of lineage-specific dependencies has shown significant clinical benefit in patients with B cell malignancies. Reversible inhibition of normal B cell production and function is well tolerated in most individuals. TRIM33 is identified as playing a role in the lineage dependency in cancers of B cell origin. Thus, there is a need for novel and potent small molecule compounds selectively targeting TRIM33 for treating or preventing various malignancies, such as lineage-specific B cell malignancies. The present application addresses the need.

SUMMARY

The present application relates to compounds that are capable of inhibiting TRIM33 activity. A first aspect of the application relates to a compound of Formula I:

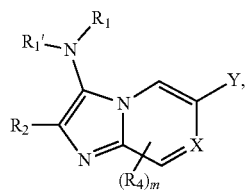

(I)

or a pharmaceutically acceptable salt or ester thereof, wherein X, Y, $R_1$, $R_1'$, $R_2$, $R_4$, and m are each described herein in detail below.

Another aspect of the present application relates to a pharmaceutical composition comprising a compound of the present application (e.g., a compound of Formula I), or a pharmaceutically acceptable salt or ester thereof, and a pharmaceutically acceptable carrier.

Another aspect of the present application relates to a method of inhibiting TRIM33, comprising administering to a subject in need thereof an effective amount of a compound of the present application (e.g., a compound of Formula I), or a pharmaceutically acceptable salt or ester thereof.

Another aspect of the present application relates to a method of treating or preventing a disease or disorder (e.g., cancer) in which TRIM33 plays a role, a cancer of B cell origin, or a lineage dependent disease or disorder in which TRIM33 plays a role, comprising administering to a subject in need thereof an effective amount of a compound of the present application (e.g., a compound of Formula I), or a pharmaceutically acceptable salt or ester thereof.

Another aspect of the present application relates to a compound of the present application (e.g., a compound of Formula I), or a pharmaceutically acceptable salt or ester thereof, for inhibiting TRIM33, or treating or preventing a disease or disorder (e.g., cancer) in which TRIM33 plays a role, a cancer of B cell origin, or a lineage dependent disease or disorder in which TRIM33 plays a role.

Another aspect of the present application relates to a compound of the present application (e.g., a compound of Formula I), or a pharmaceutically acceptable salt or ester thereof, for use in the manufacture of a medicament in the inhibition of TRIM33, or the treatment or prevention of a disease or disorder (e.g., cancer) in which TRIM33 plays a role, a cancer of B cell origin, or a lineage dependent disease or disorder in which TRIM33 plays a role.

Another aspect of the present application relates to use of a compound of the present application (e.g., a compound of Formula I), or a pharmaceutically acceptable salt or ester thereof, in inhibiting TRIM33, or treating or preventing a disease or disorder (e.g., cancer) in which TRIM33 plays a role, a cancer of B cell origin, or a lineage dependent disease or disorder in which TRIM33 plays a role.

The details of the application are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference.

BRIEF DESCRIPTION OF THE DRAWINGS

FIGS. 3A and 3B are plots showing TRIM33 modulating activity of compounds of the present application as listed in Table 2a.

FIGS. 4A and 4B are plots showing TRIM24 modulating activity of compounds of the present application as listed in Table 2a.

DETAILED DESCRIPTION

Compounds of the Application

Figure 1:
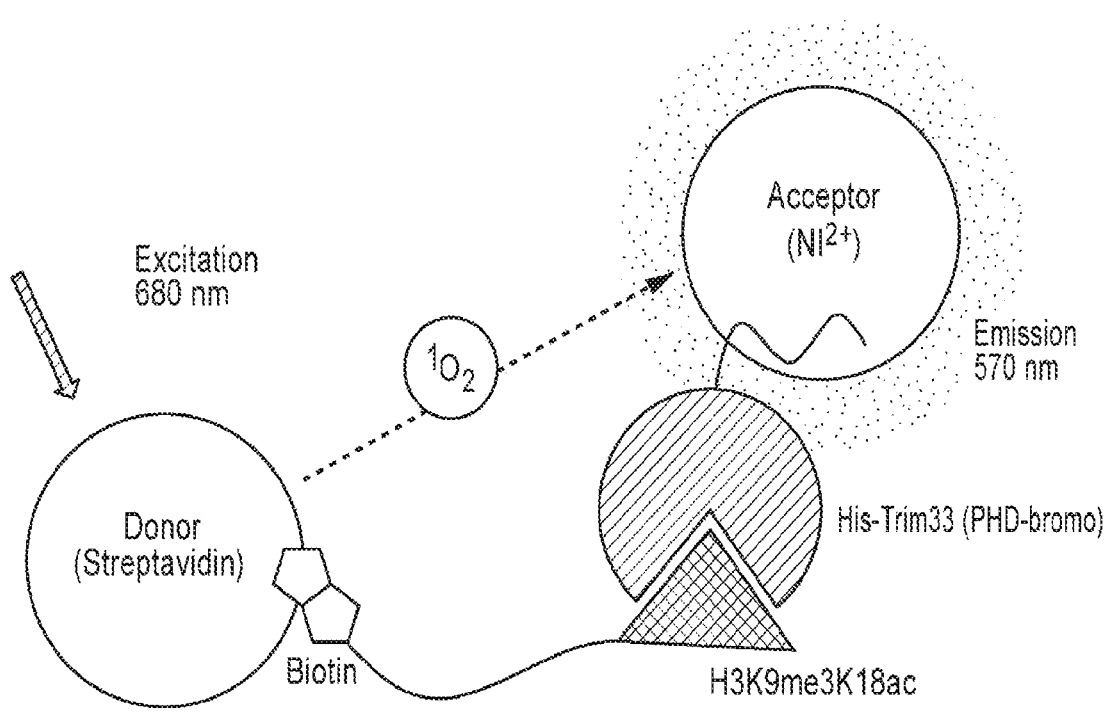
FIG. 1 is an illustration of the AlphaScreen assay for assessing the compounds of the present application.
Figure 2A:
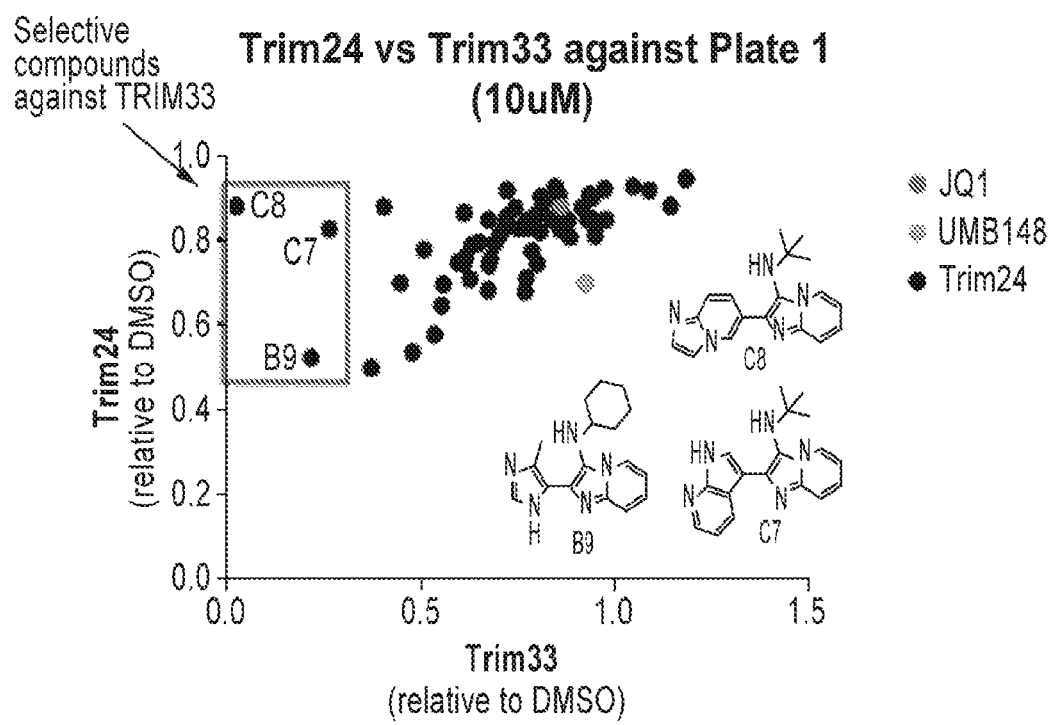
FIGS. 2A and 2B are plots displaying the TRIM24 (y-axis) and TRIM33 (x-axis) modulating activities of compounds of the present application or reference compounds at the indicated concentrations. As indicated, compounds such as Compounds C7, C8, and B9 (FIG. 2A) and Compounds B8, C9, and F9 (FIG. 2B) show selectivity for TRIM33 over TRIM24.
Figure 2B:
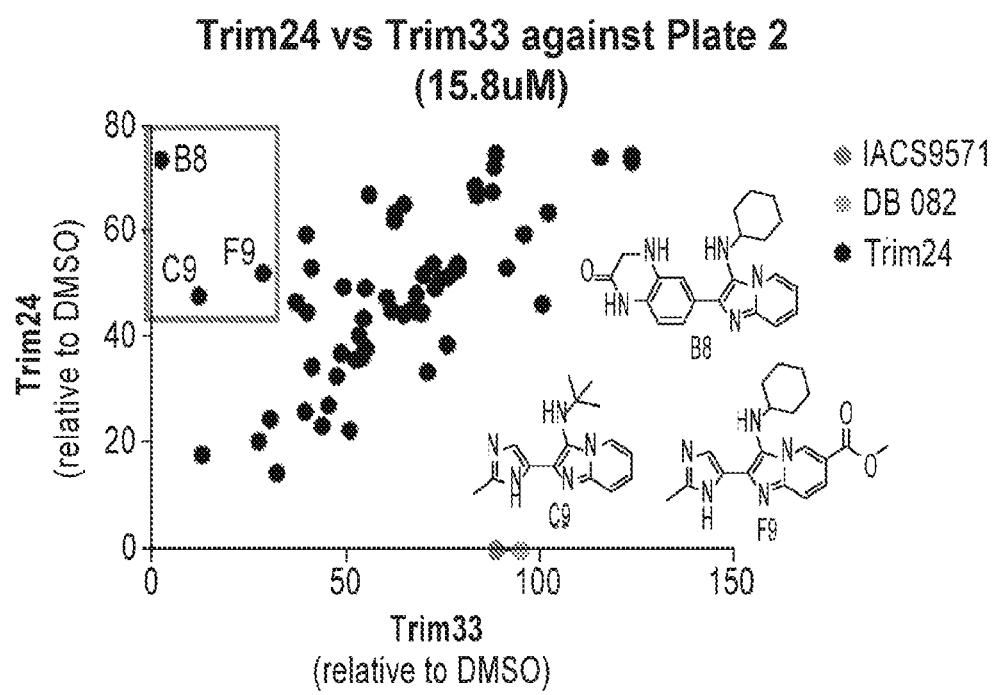
Figure 3A:
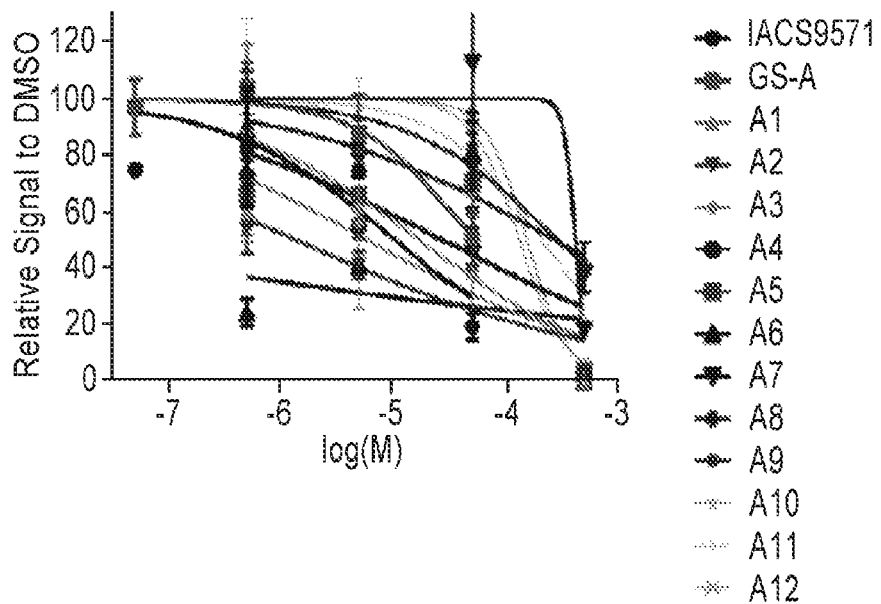
Figure 3A:
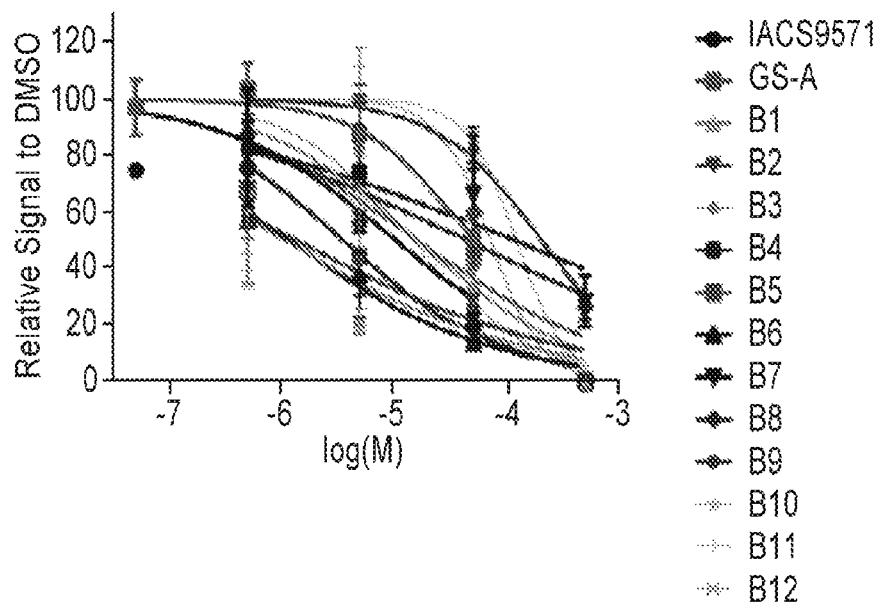
Figure 3A:
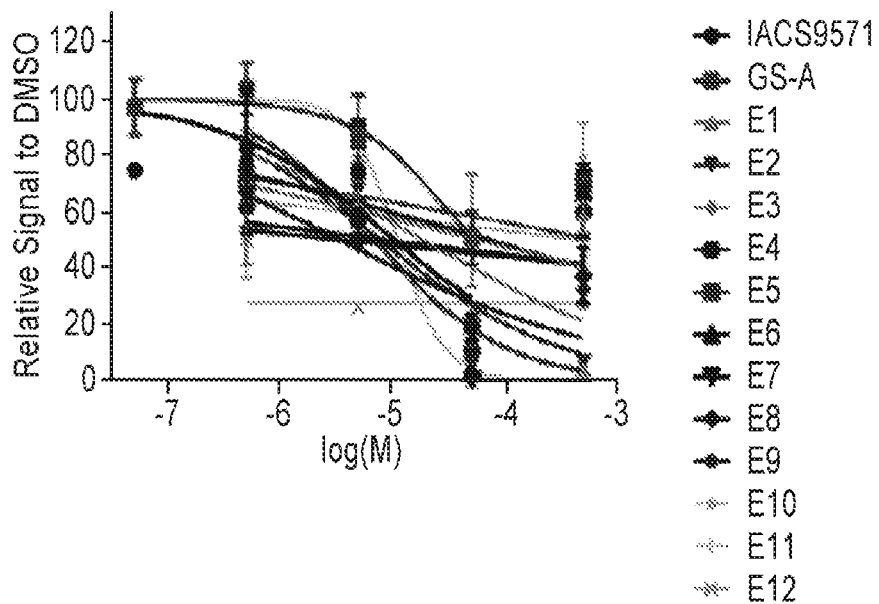
Figure 3A:
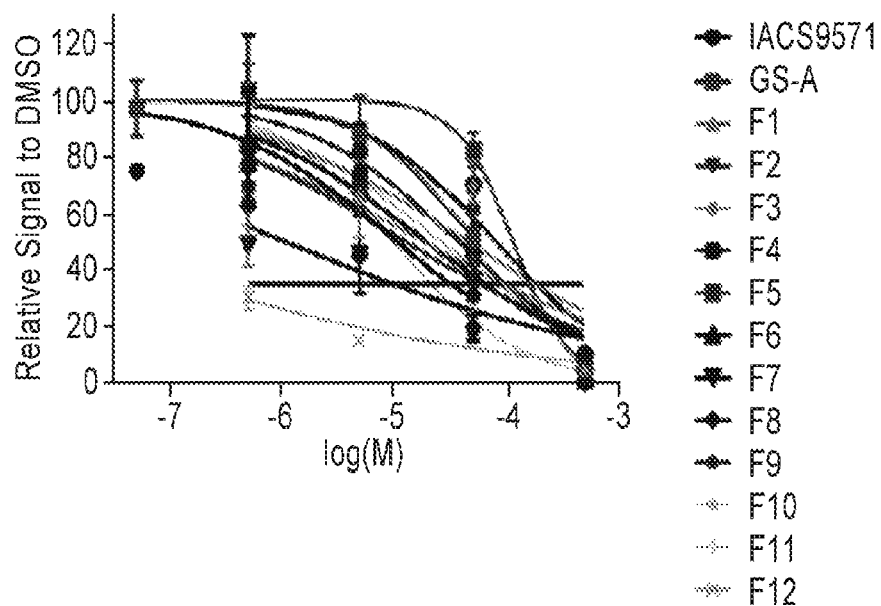
Figure 3B:
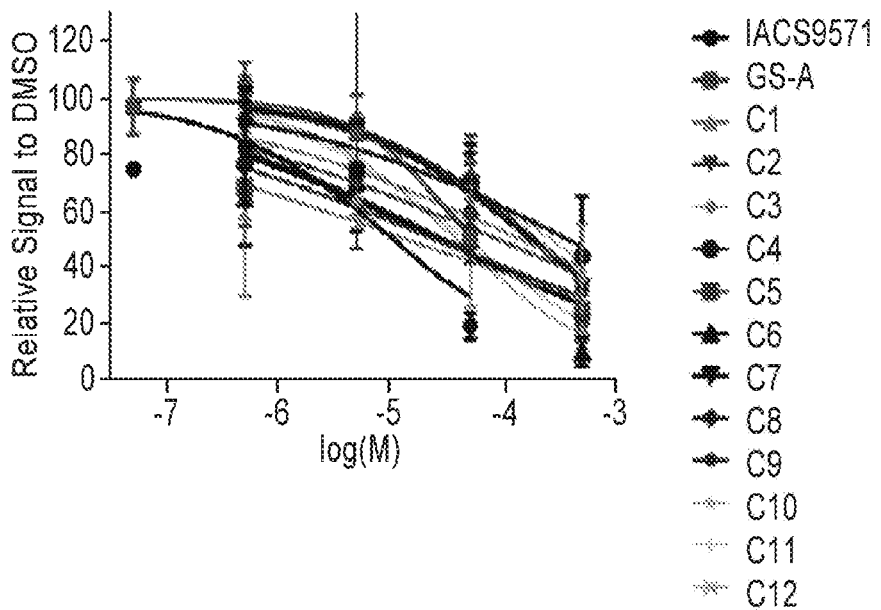
Figure 3B:
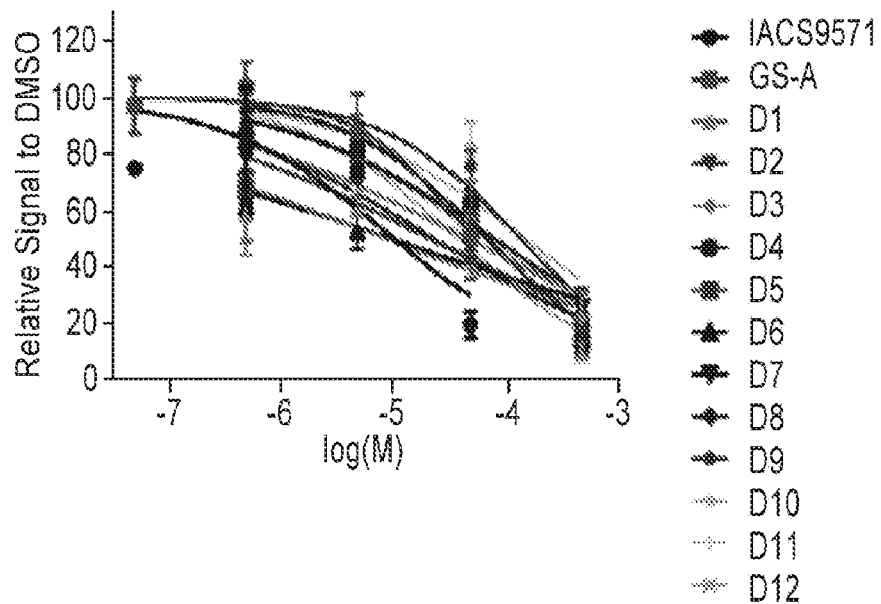
Figure 3B:
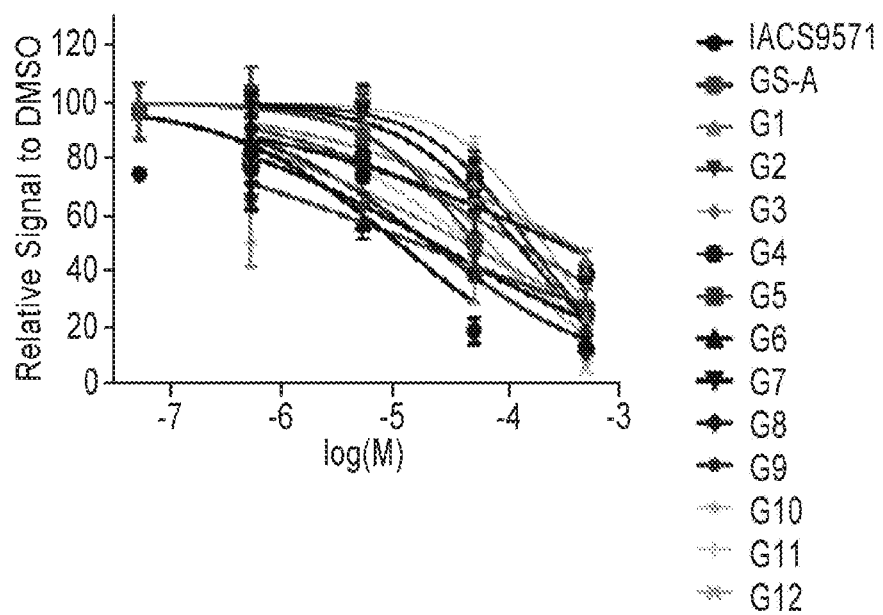
Figure 3B:
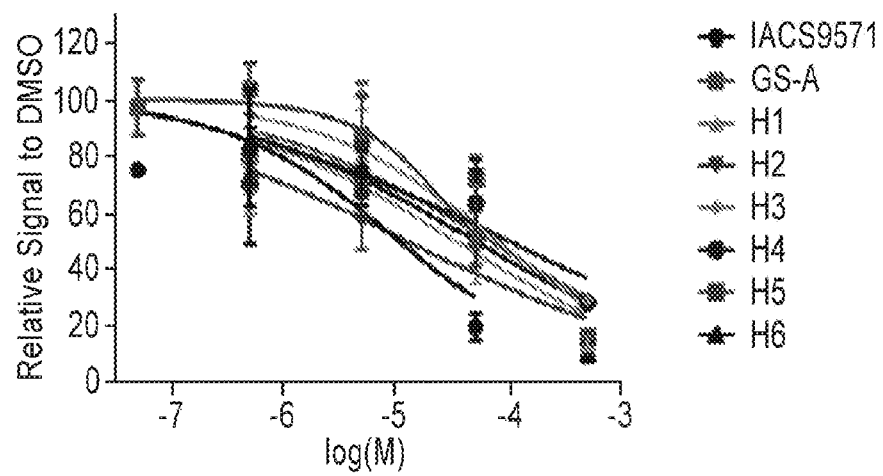
Figure 4A:
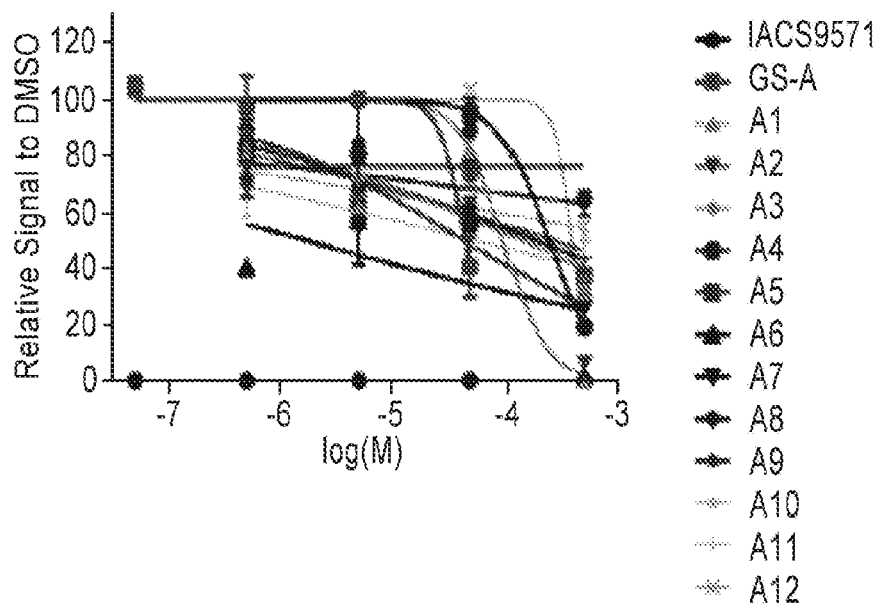
Figure 4A:
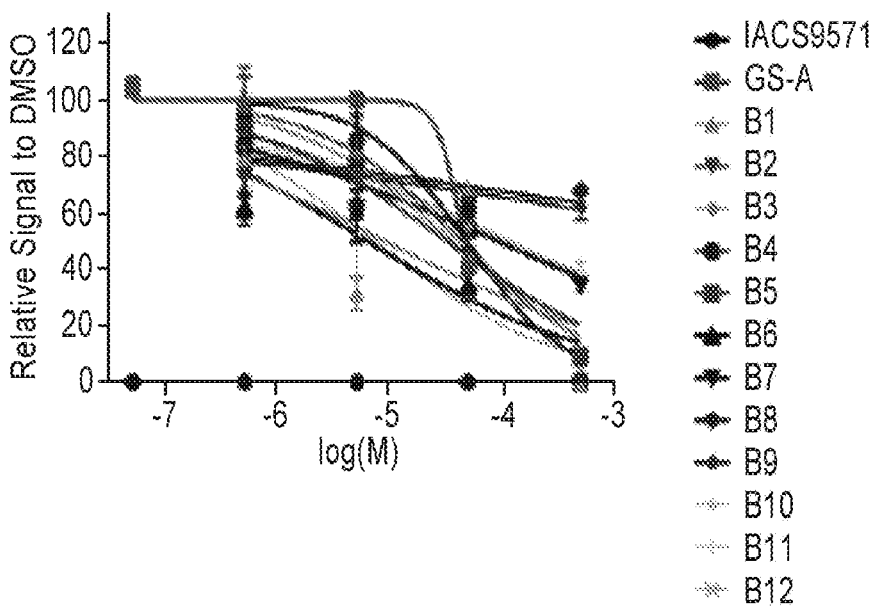
Figure 4A:
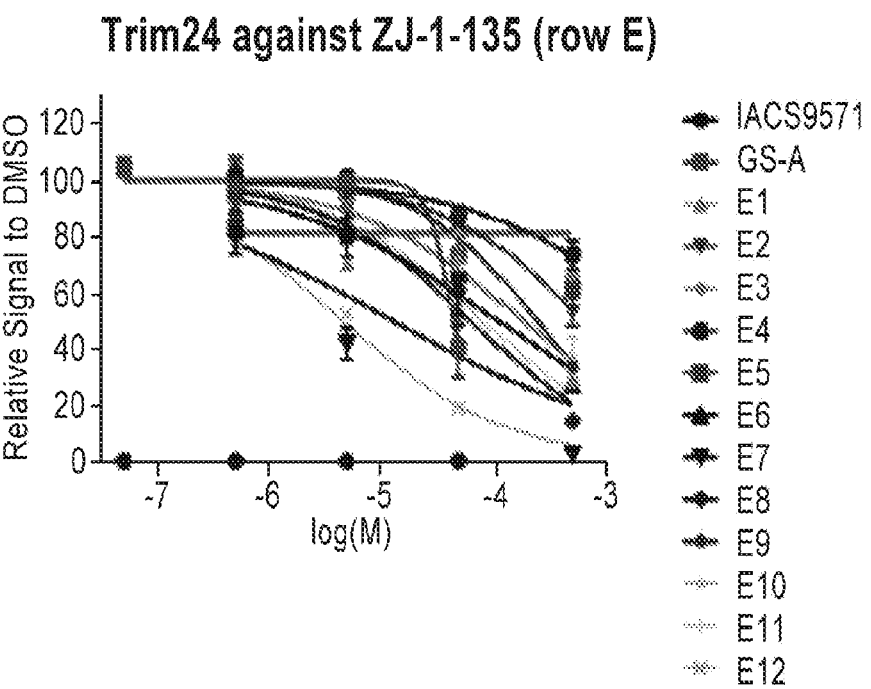
Figure 4A:
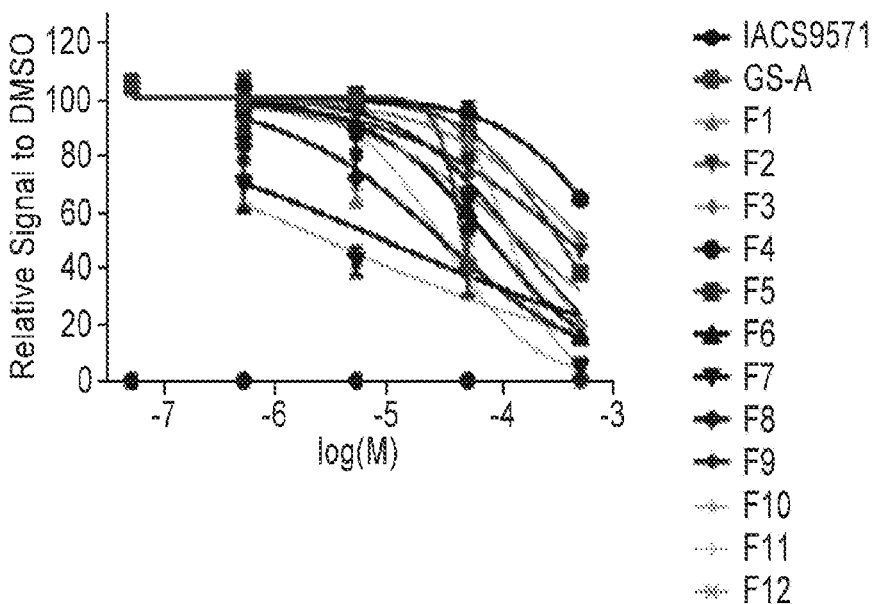
Figure 4B:
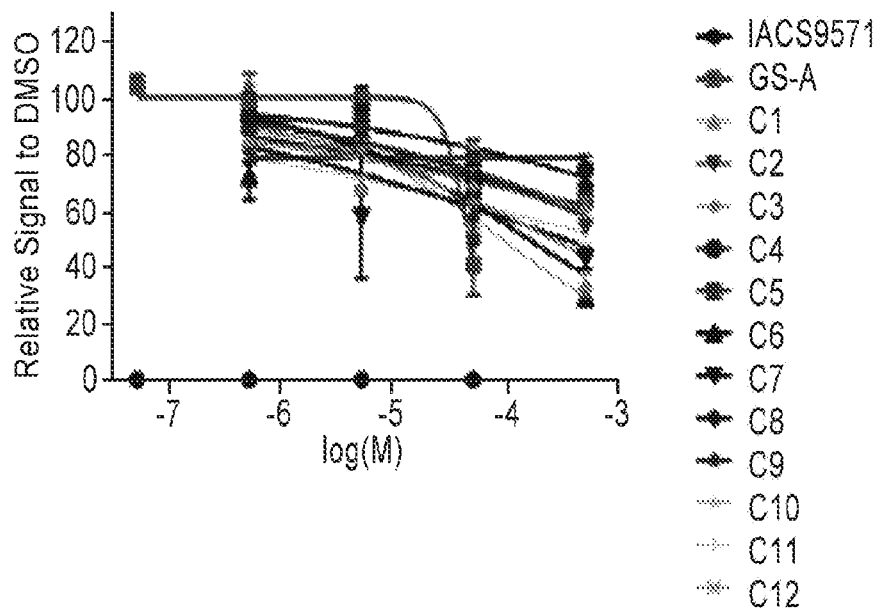
Figure 4B:
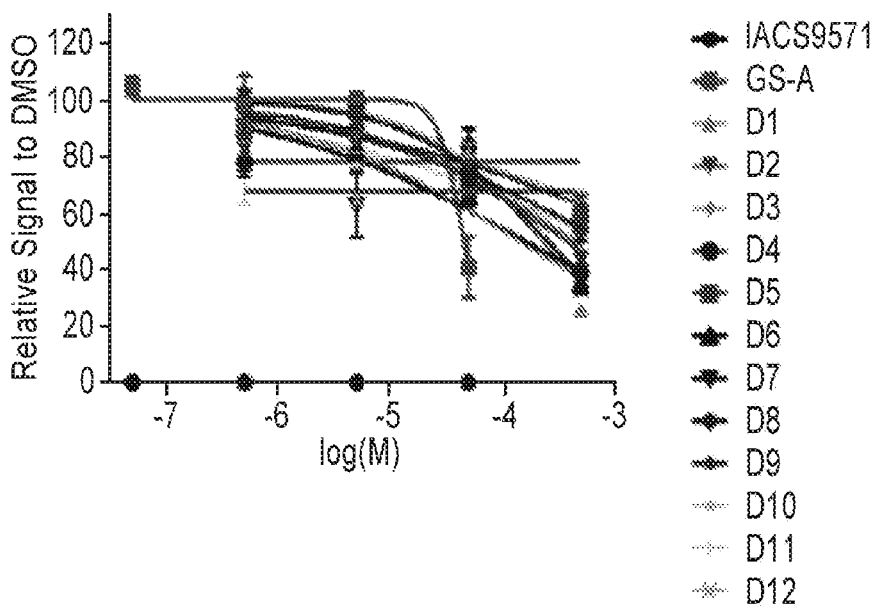
Figure 4B:
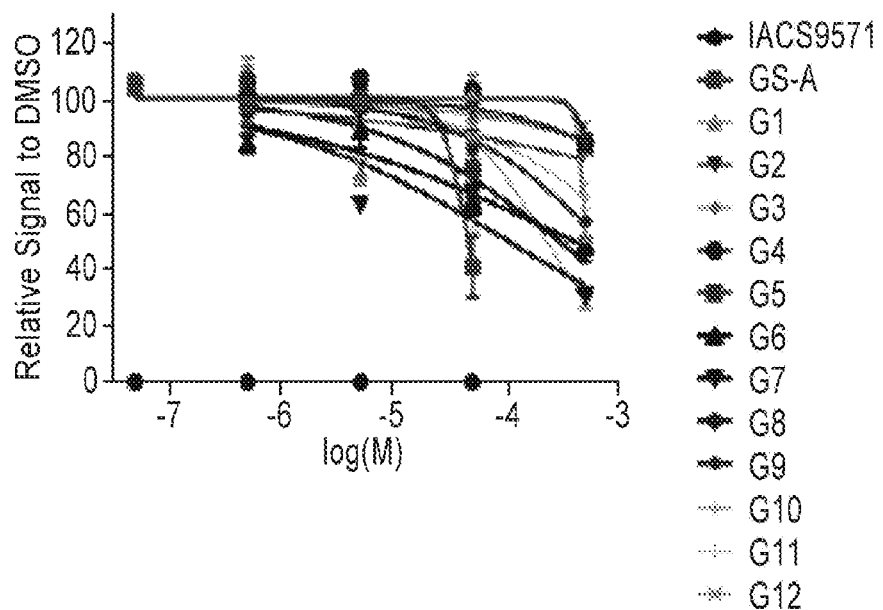
Figure 4B:
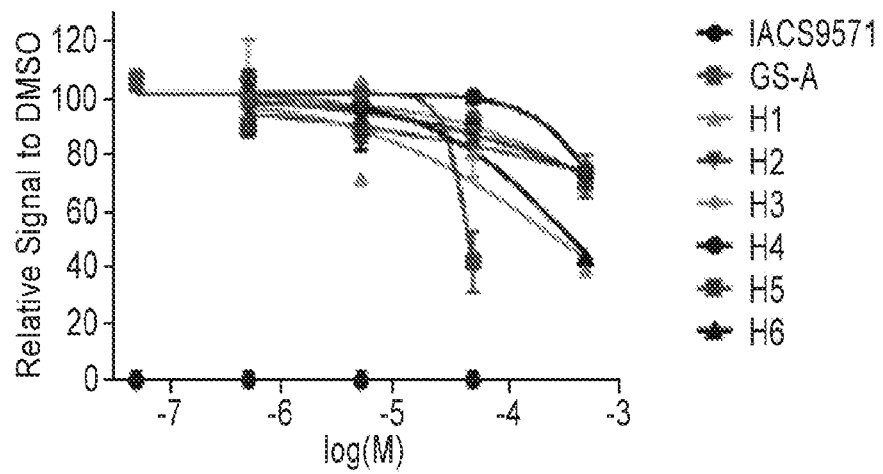
Figure 5:
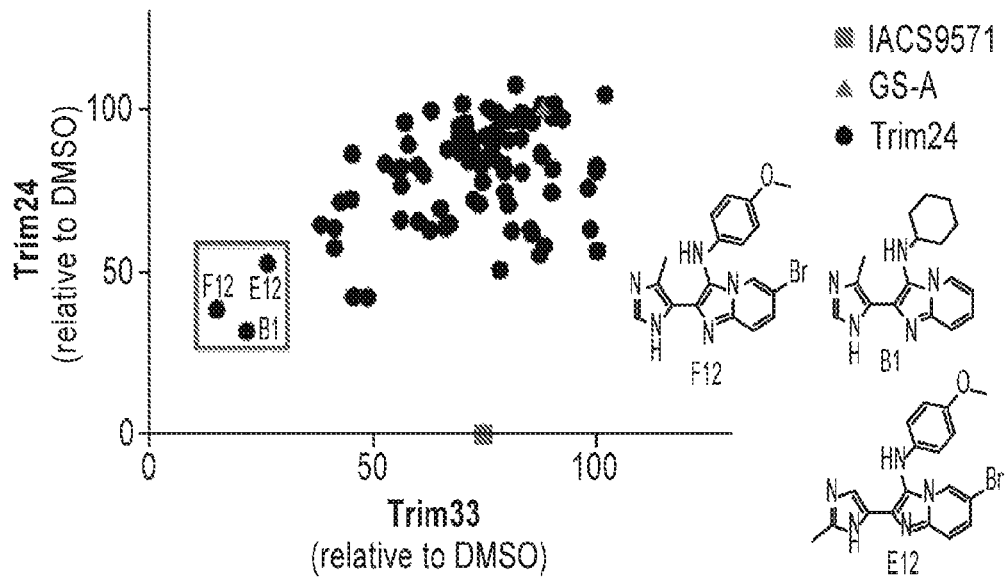
FIG. 5 is a plot displaying the TRIM24 (y-axis) and TRIM33 (x-axis) modulating activities of compounds of the present application or reference compounds at the indicated concentration. As indicated, compounds such as Compounds B1, E12, and F12 show selectivity for TRIM33 over TRIM24.
Figure 6:
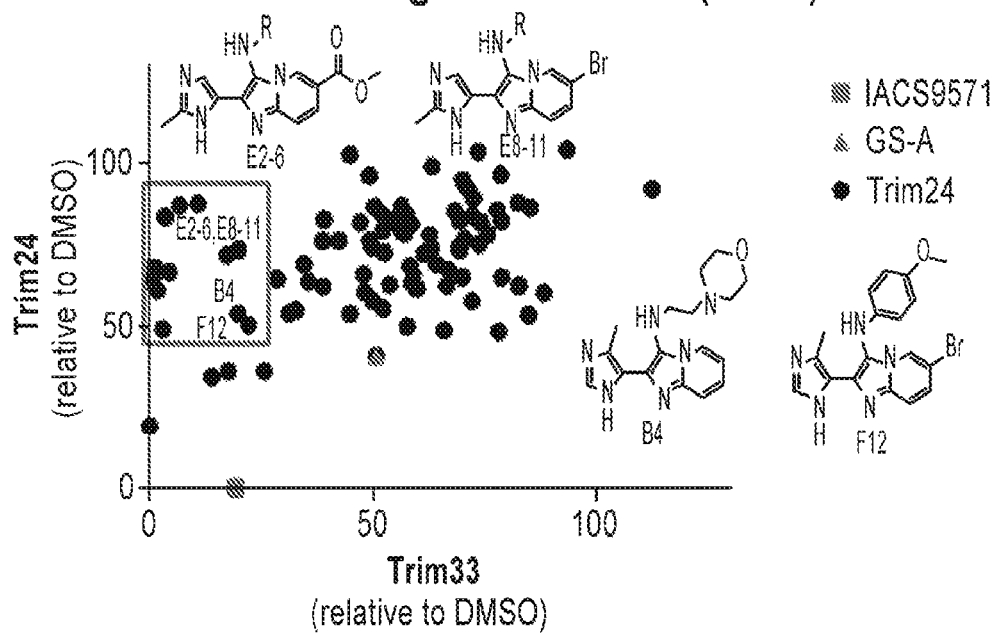
FIG. 6 is a plot displaying the TRIM24 (y-axis) and TRIM33 (x-axis) modulating activities of compounds of the present application or reference compounds at the indicated concentration. As indicated, compounds such as Compounds B4, E2-6, E8-11, and F12 show selectivity for TRIM33 over TRIM24.
Figure 7:
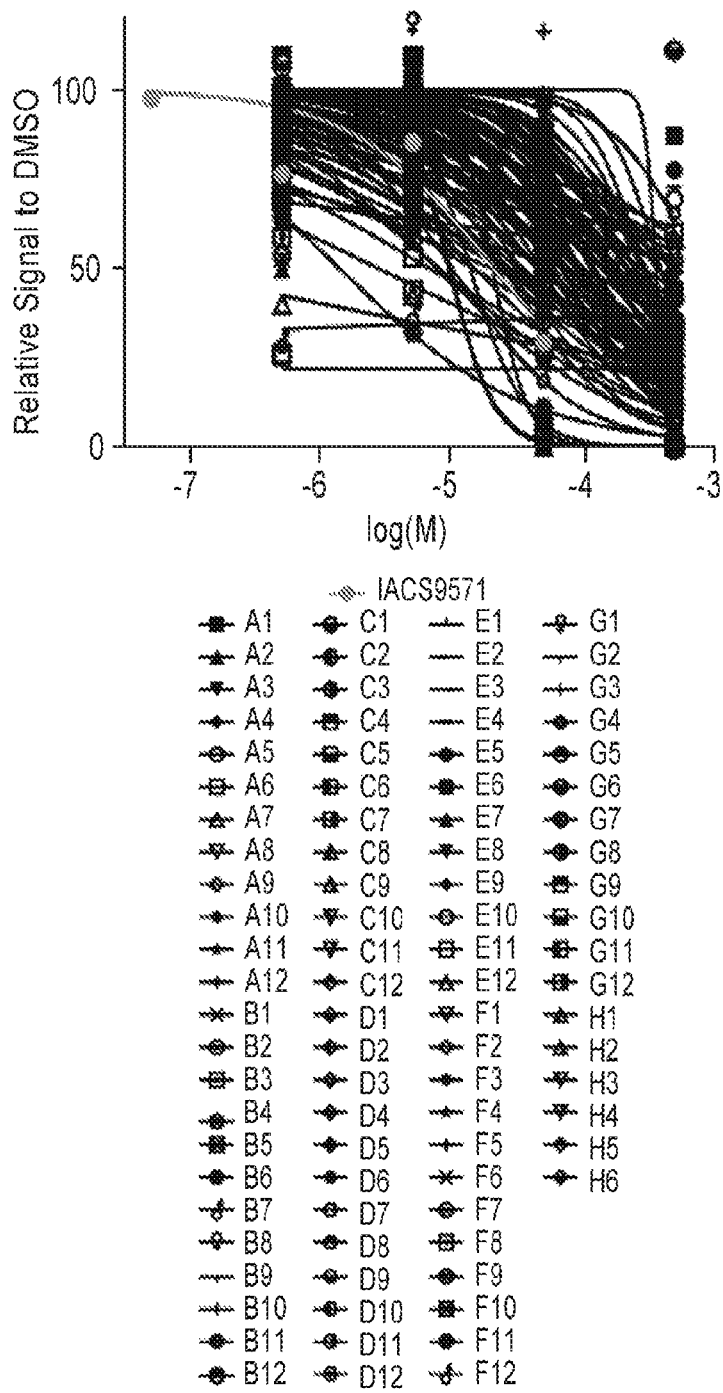
FIG. 7 is a plot showing TRIM33 modulating activity of compounds of the present application as listed in Table 2b.
Figure 8:
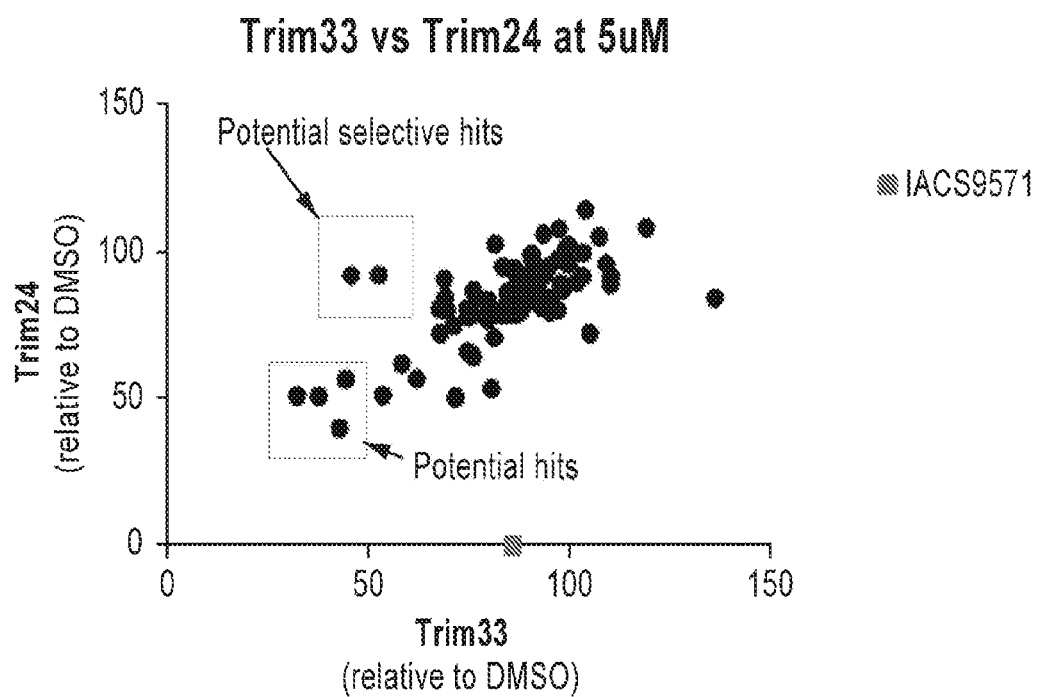
FIG. 8 is a plot displaying the TRIM24 (y-axis) and TRIM33 (x-axis) modulating activities of compounds of the present application or a reference compound at the indicated concentration.
Figure 9A:
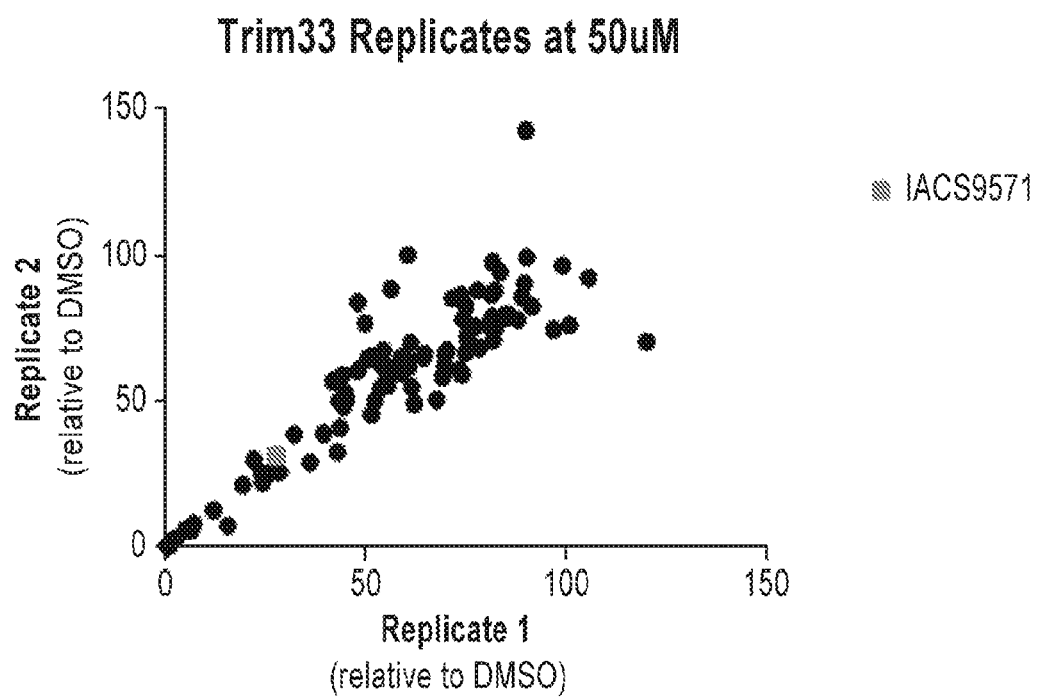
FIGS. 9A and 9B are plots displaying the TRIM24 (y-axis) and TRIM33 (x-axis) modulating activities of compounds of the present application or a reference compound at the indicated concentration.
Figure 9B:
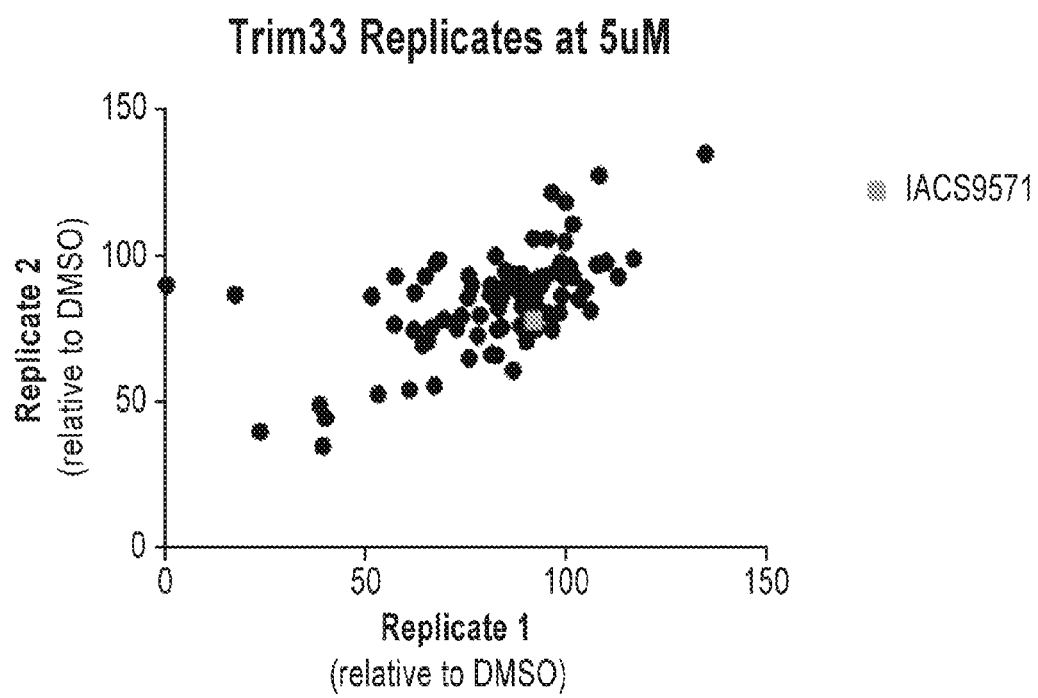
Figure 10A:
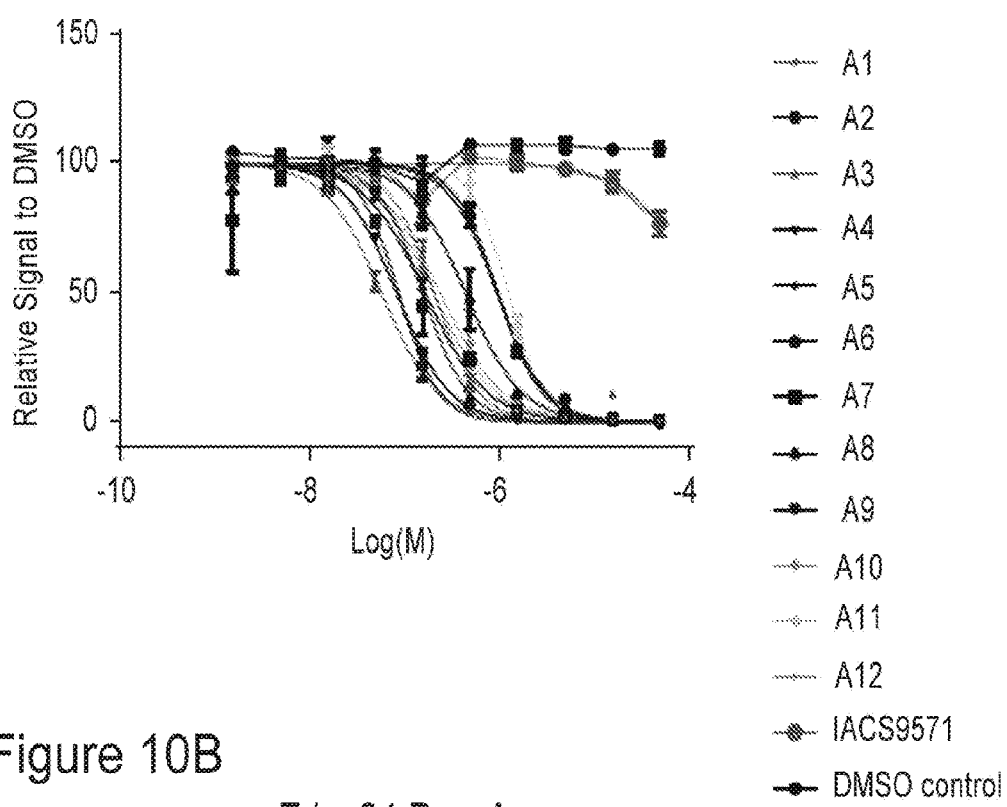
FIGS. 10A-10P are plots showing TRIM33 modulating activity of compounds of the present application.
Figure 10B:
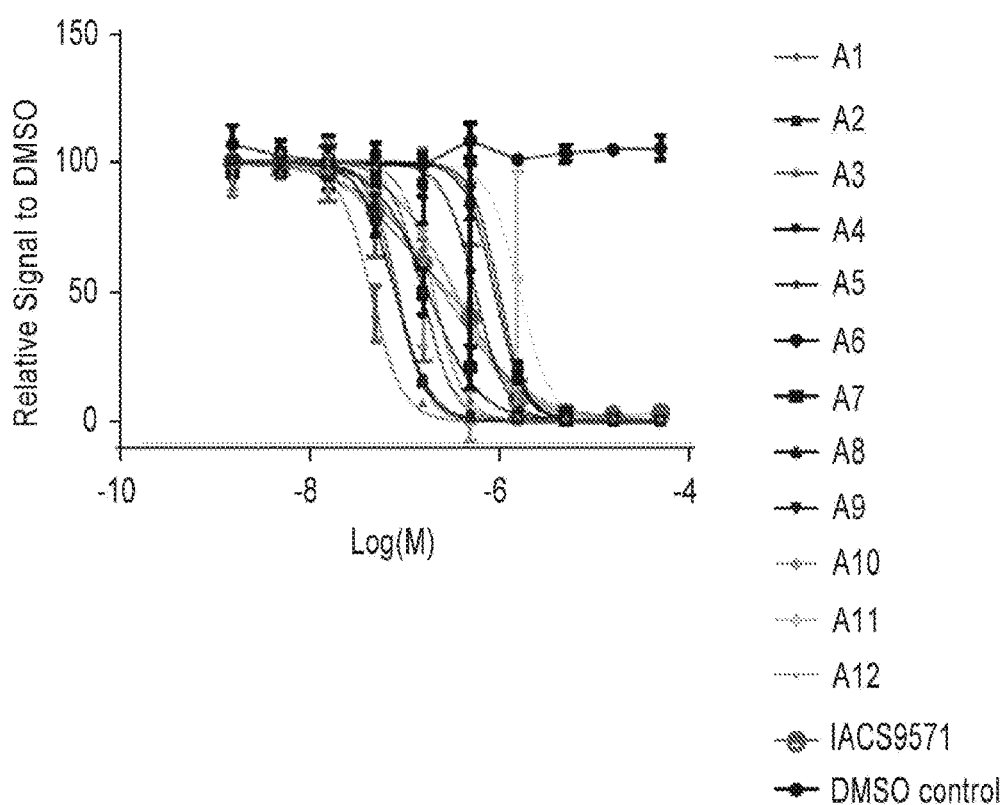
Figure 10C:
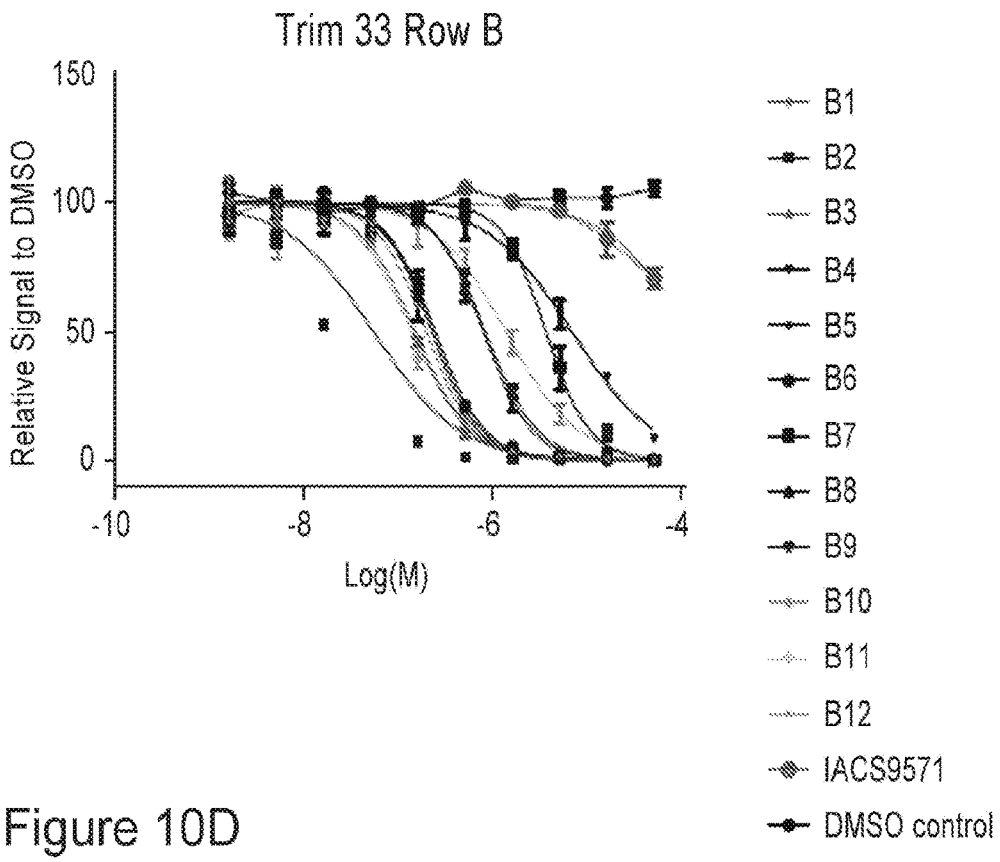
Figure 10D:
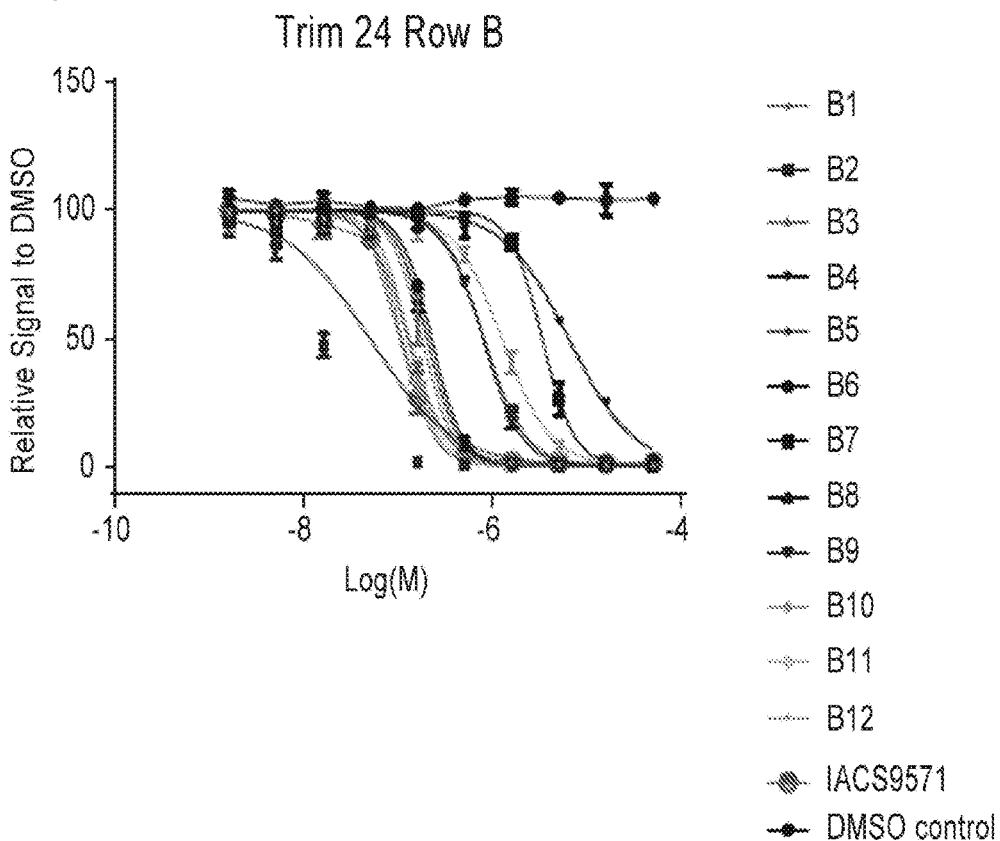
Figure 10E:
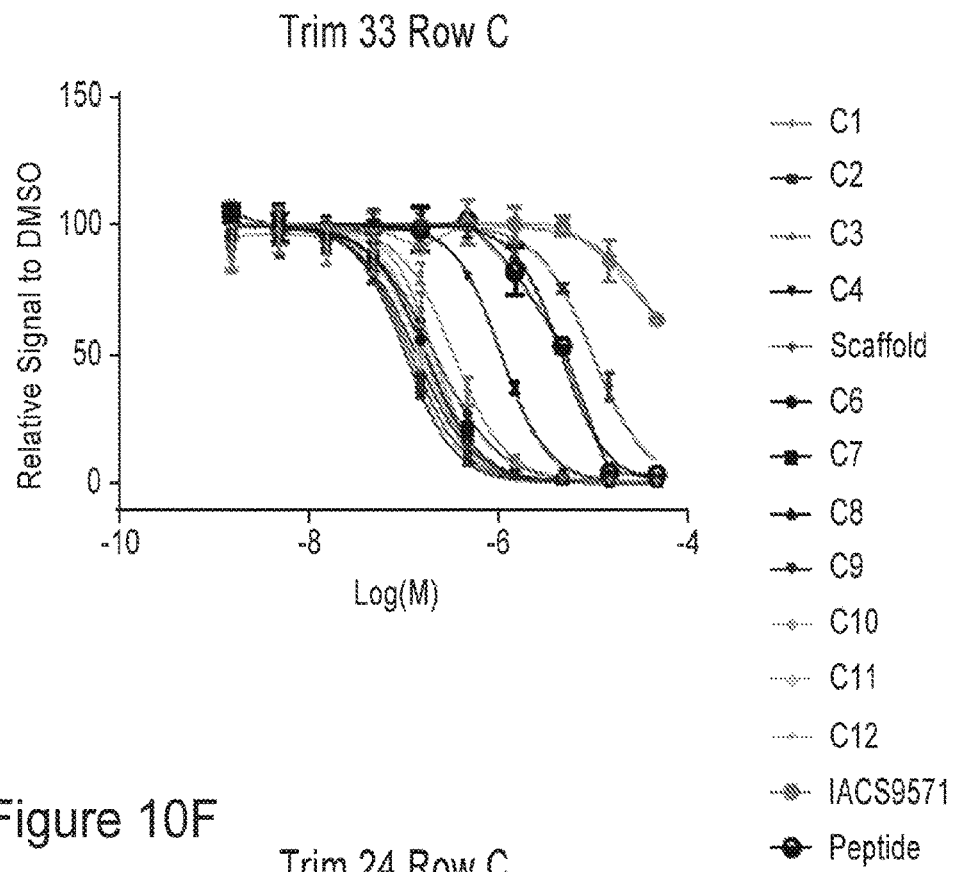
Figure 10F:
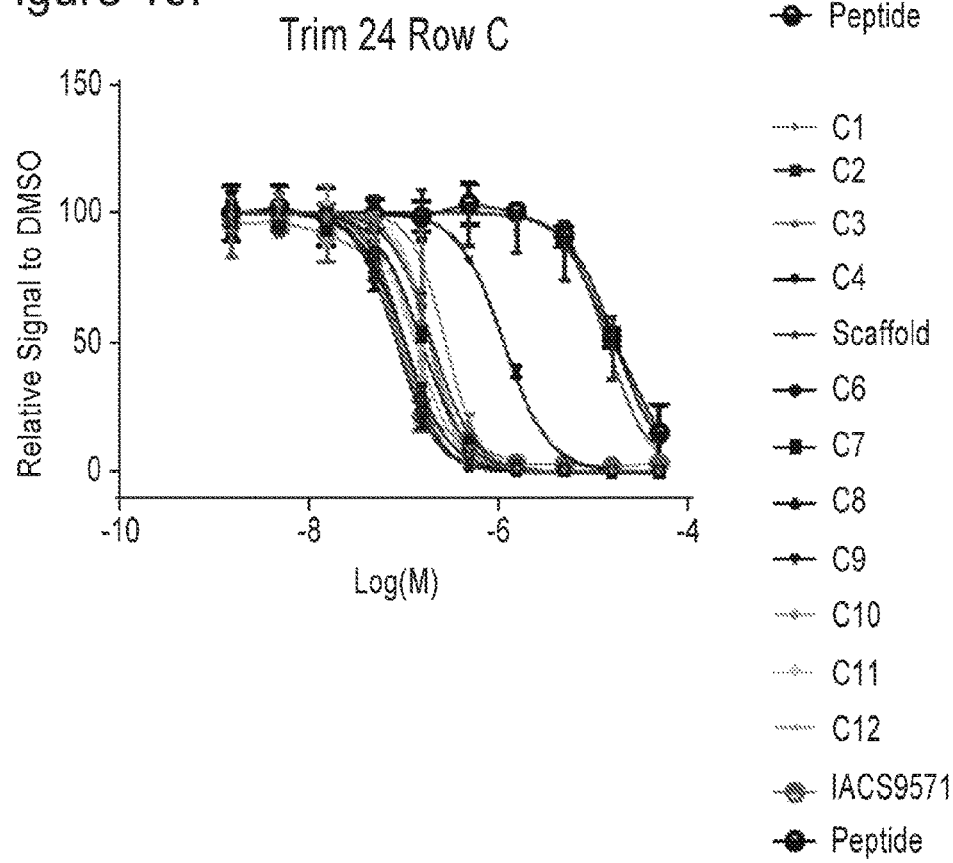
Figure 10G:
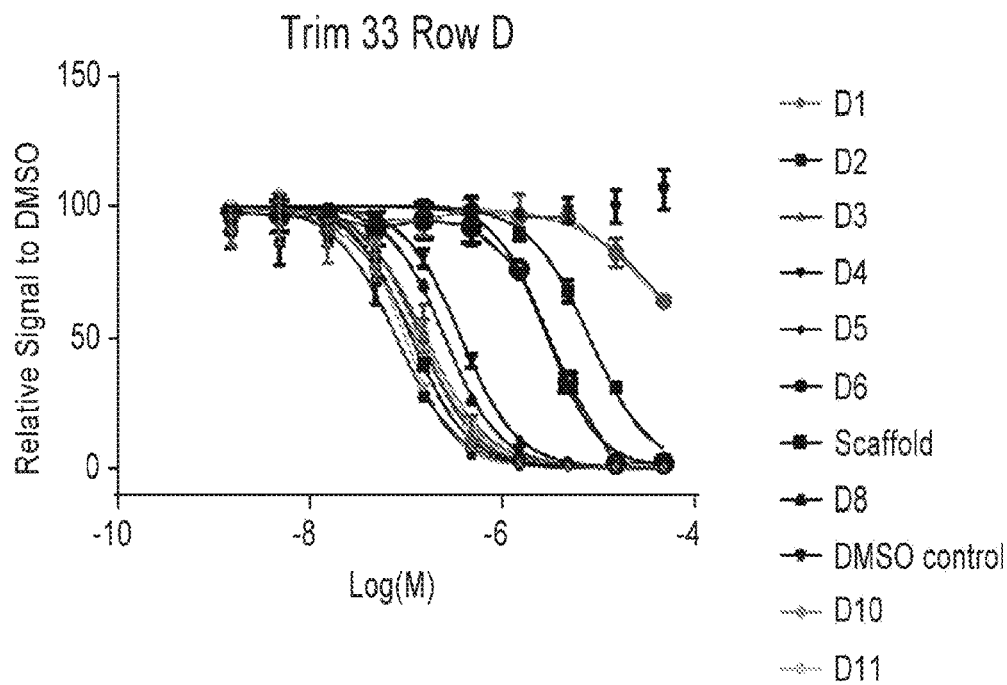
Figure 10H:
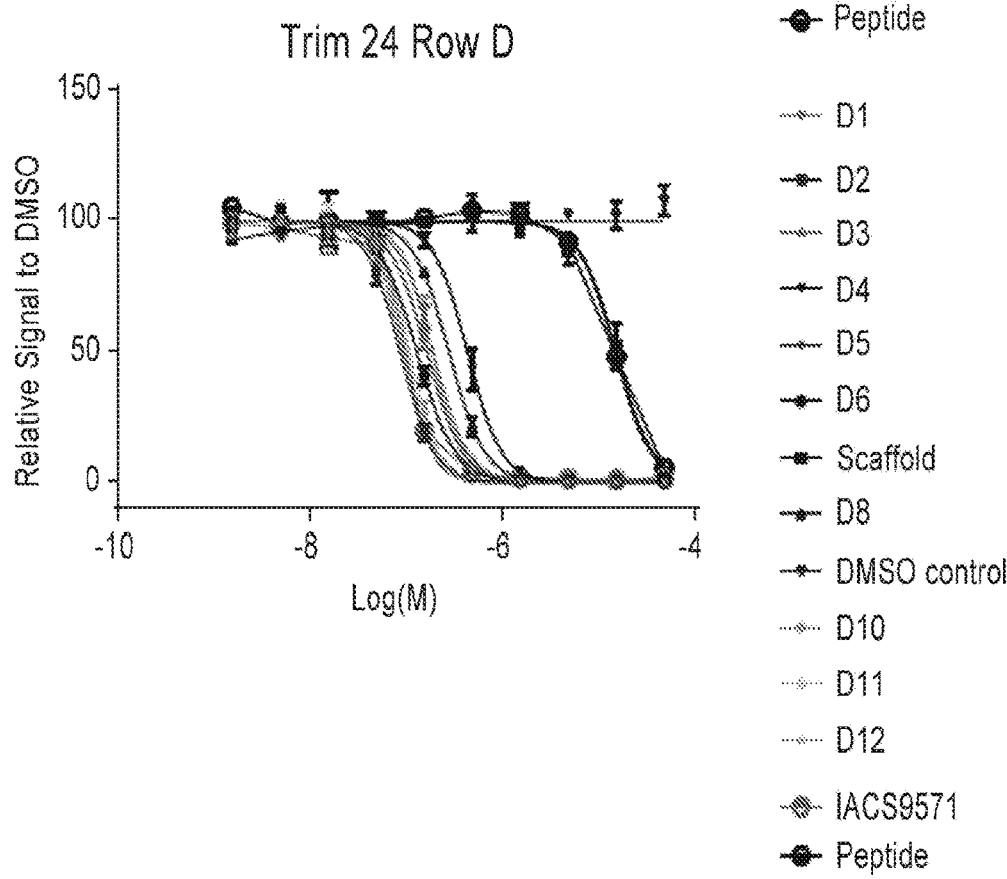
Figure 10I:
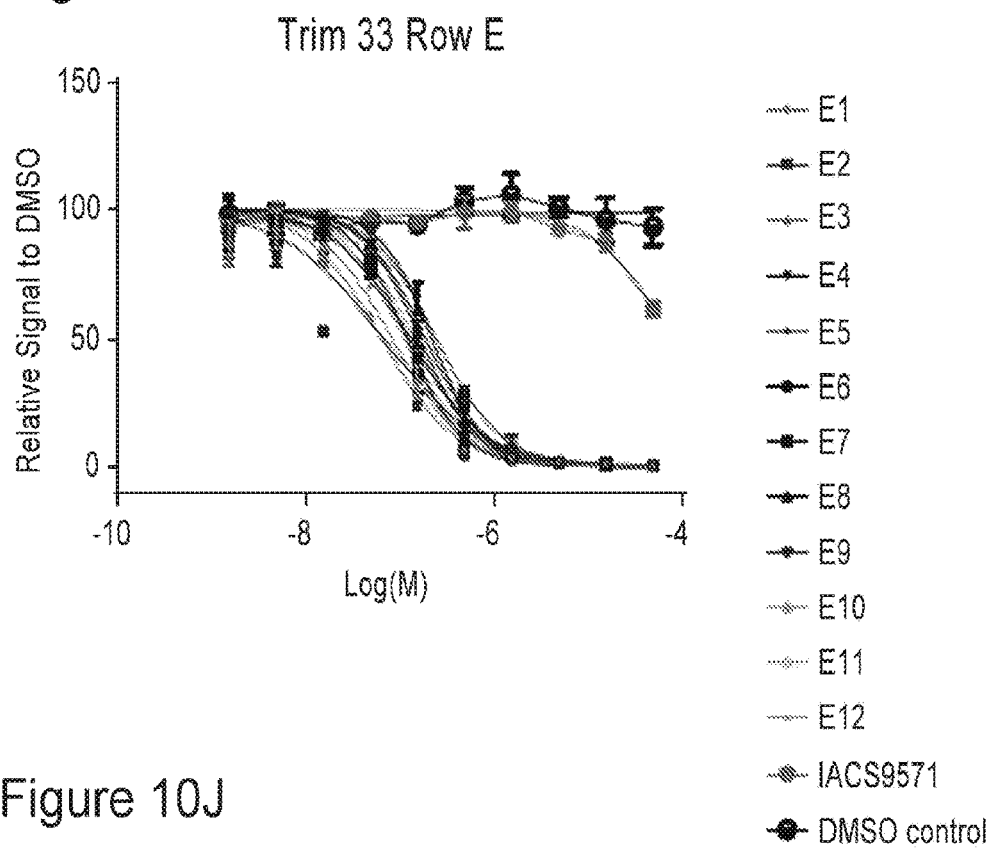
Figure 10J:
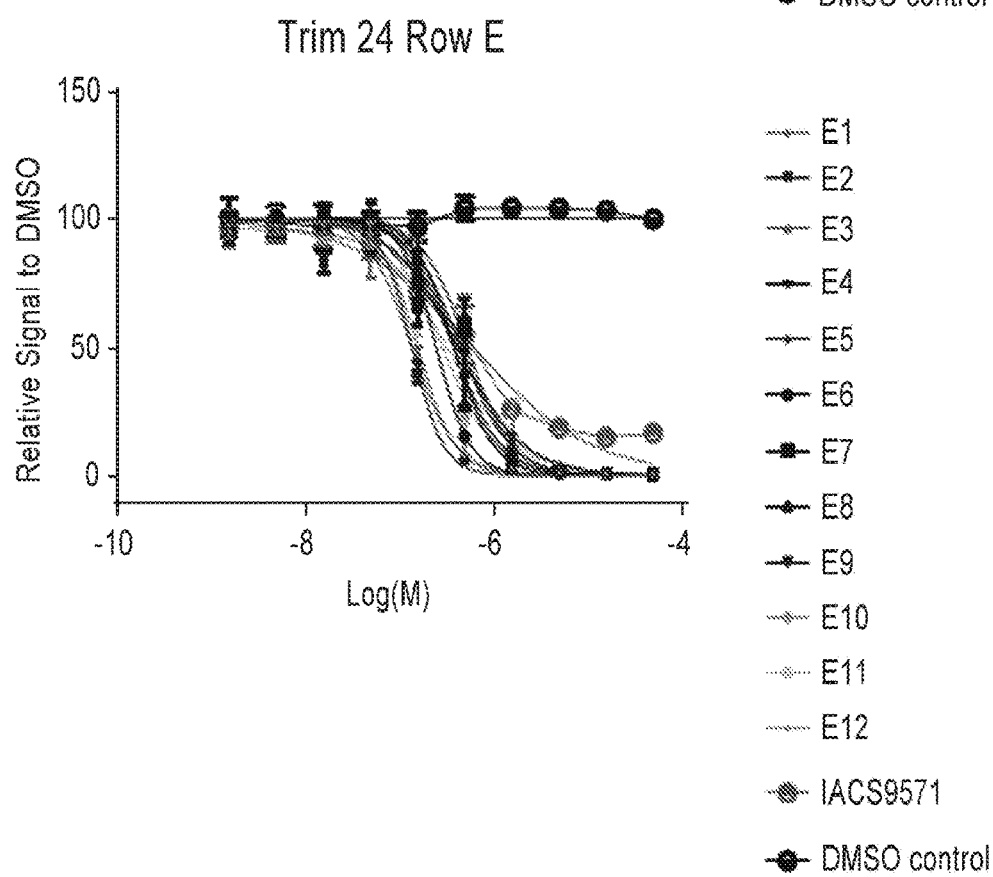
Figure 10K:
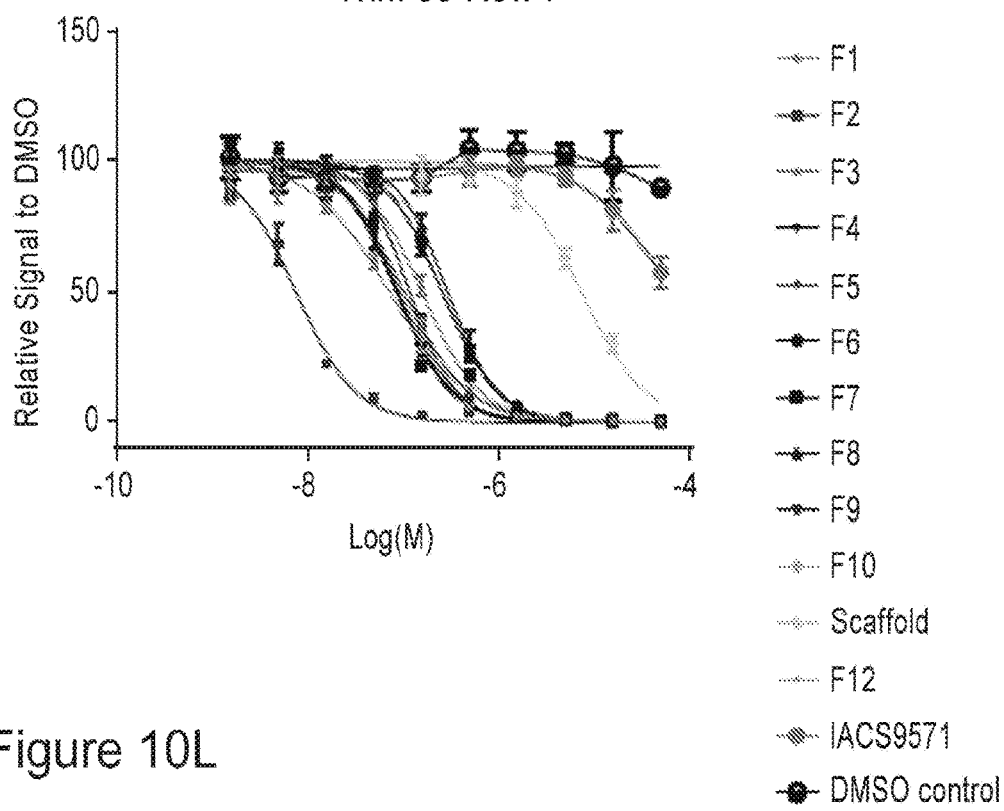
Figure 10L:
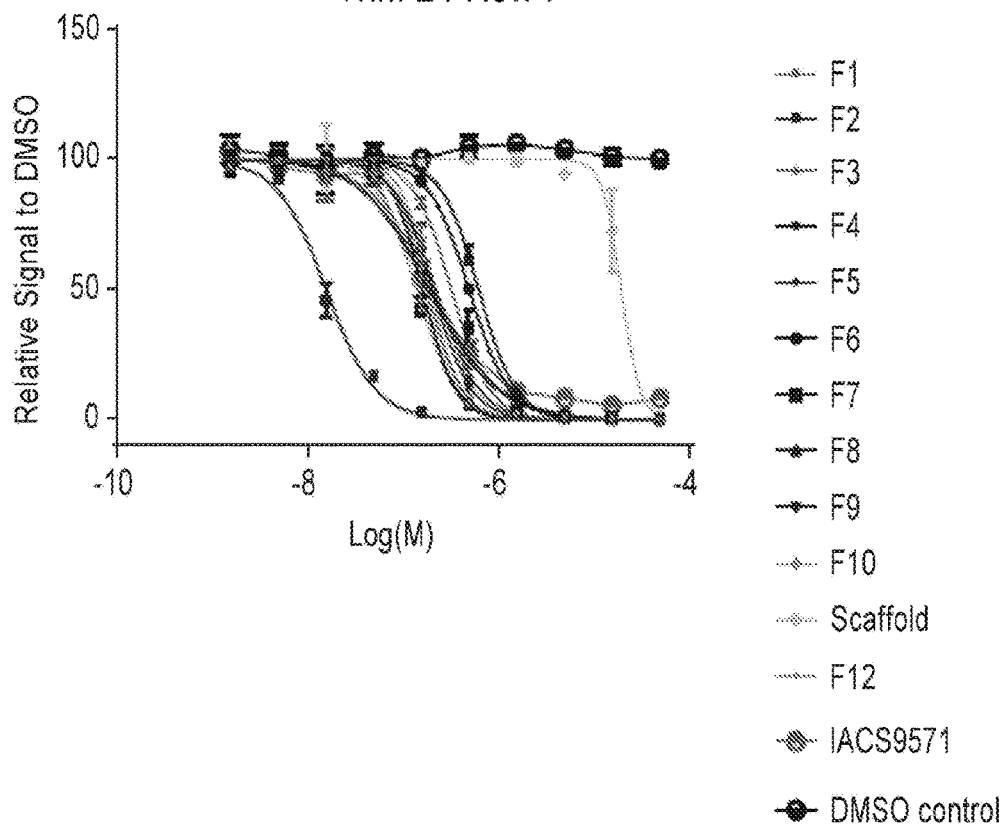
Figure 10M:
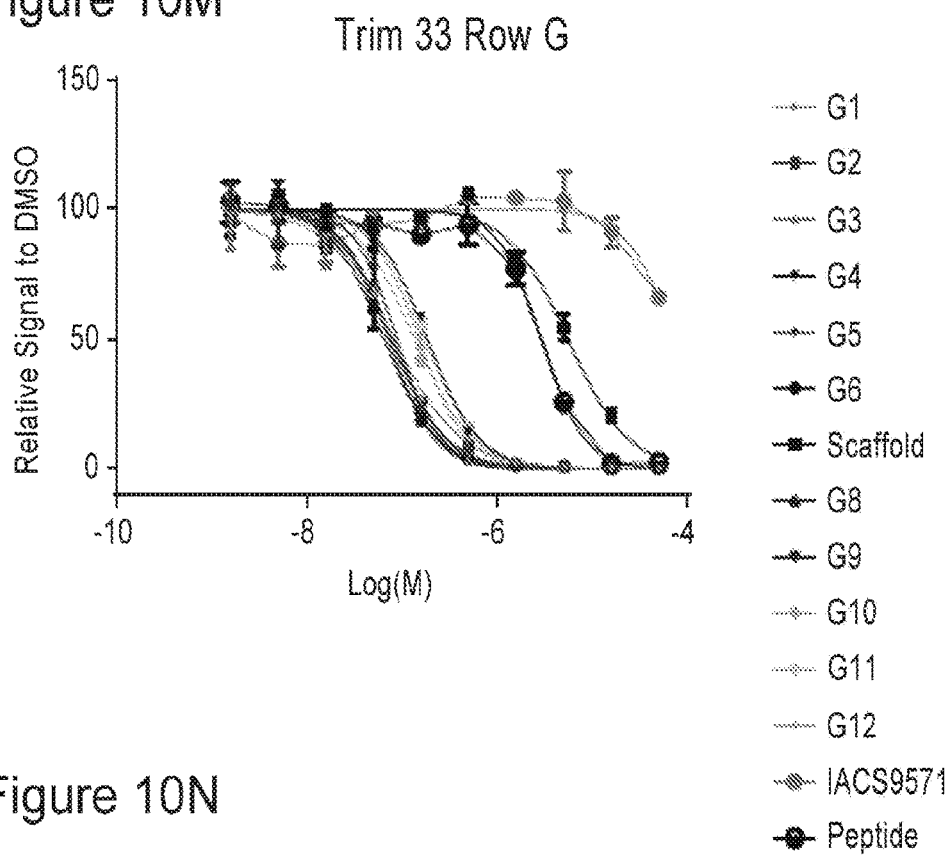
Figure 10N:
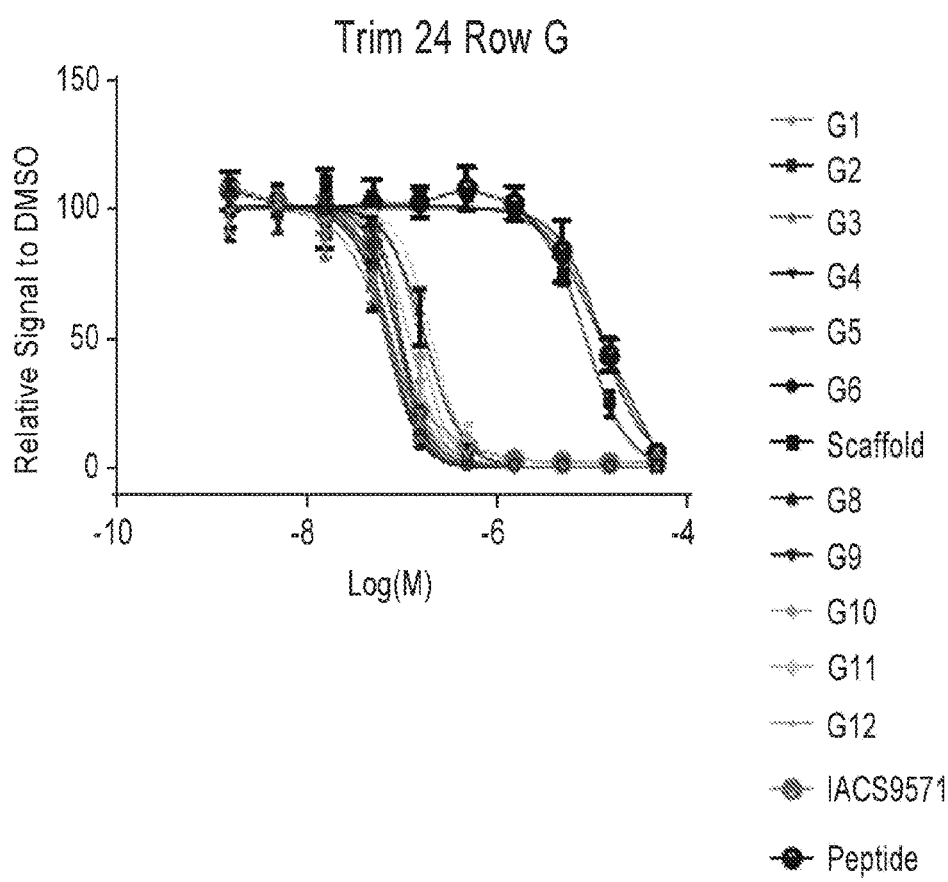
Figure 10O:
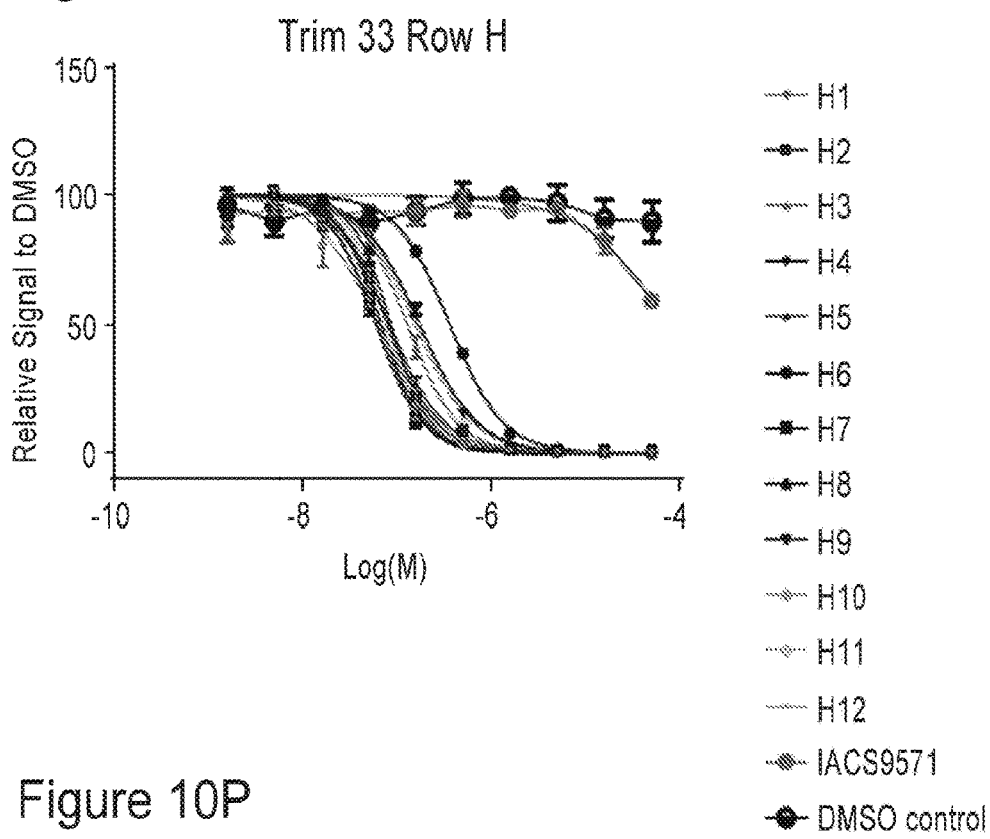
Figure 10P:
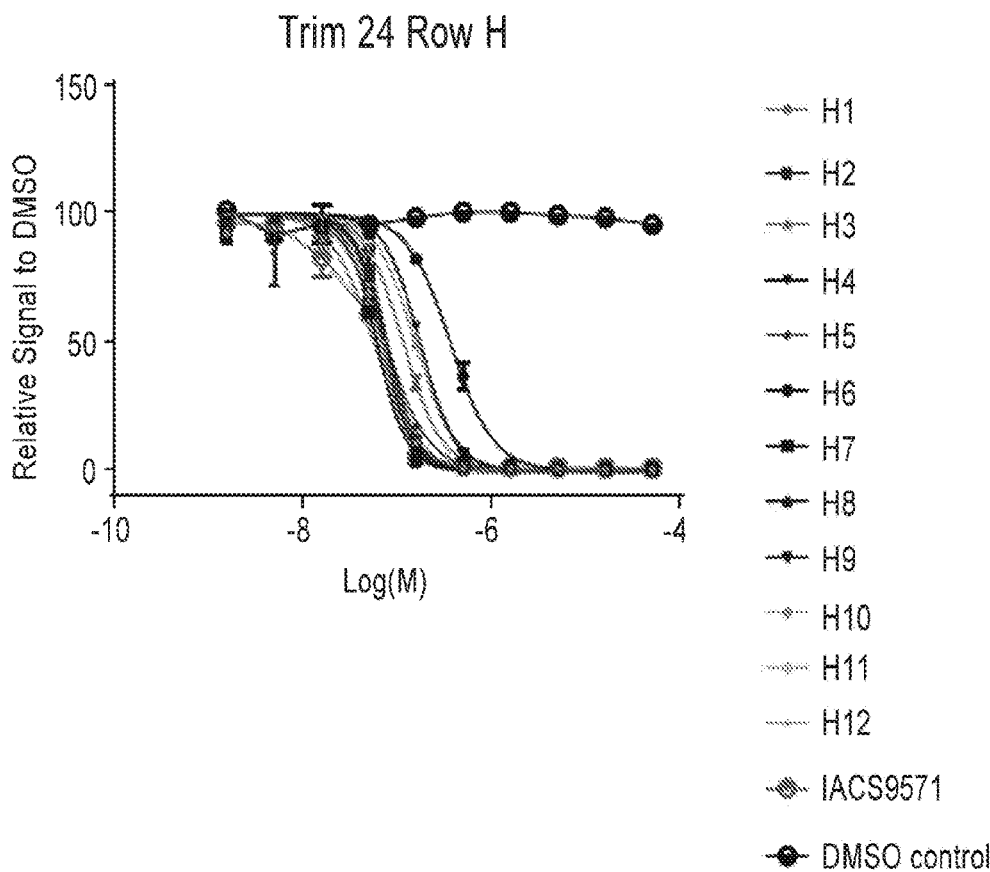

A first aspect of the application relates to a compound of Formula I:

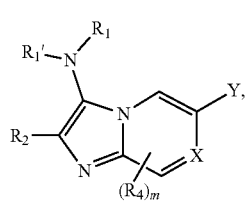

(I)

or a pharmaceutically acceptable salt or ester thereof, wherein:

X is N or $CR_3$;

$R_3$ is H, $(C_1-C_4)$ alkyl, $(C_1-C_4)$ haloalkyl, $(C_1-C_4)$ alkoxy, $(C_1-C_4)$ haloalkoxy, halogen, OH, $NH_2$, $NH(C_1-C_4)$ alkyl, $N((C_1-C_4)$ alkyl$)_2$, C(O)OH, C(O)$(C_1-C_4)$ alkyl, C(O)O$(C_1-C_4)$ alkyl, C(O)NH$(C_1-C_4)$ alkyl, NHC(O)$(C_1-C_4)$ alkyl, NHC(O)O$(C_1-C_4)$ alkyl, or NHC(O)NH$(C_1-C_4)$ alkyl;

Y is H, $(C_1-C_4)$ alkyl, $(C_1-C_4)$ haloalkyl, $(C_1-C_4)$ alkoxy, $(C_1-C_4)$ haloalkoxy, halogen, OH, $NH_2$, $NH(C_1-C_4)$ alkyl, $N((C_1-C_4)$ alkyl$)_2$, C(O)OH, C(O)$(C_1-C_4)$ alkyl, C(O)O$(C_1-C_4)$ alkyl, C(O)NH$(C_1-C_4)$ alkyl, NHC(O)$(C_1-C_4)$ alkyl, NHC(O)O$(C_1-C_4)$ alkyl, NHC(O)NH$(C_1-C_4)$ alkyl, C(O)NHNH$_2$, or C(O)NHN=$CR_7R_7'$;

$R_7$ and $R_7'$ are each independently H, $(C_1-C_4)$ alkyl, $(C_1-C_4)$ haloalkyl, or $(CHR_5)_{n2}$—$R_{7a}$, or $R_7$ and $R_7'$, together with the carbon atom to which they are attached, form $C_3-C_8$ cycloalkyl, $C_3-C_8$ cycloalkenyl, or heterocyclyl comprising one, two, or three 4- to 7-membered rings and 1-4 heteroatoms selected from N, O, and S, wherein the cycloalkyl, cycloalkenyl, or heterocyclyl is optionally substituted with one or more $R_{sb2}$;

$R_{7a}$ is OH, SH, S$(C_1-C_4)$ alkyl, $(C_1-C_4)$ alkoxy, $(C_1-C_4)$ haloalkoxy, O—$C_6-C_{10}$ aryl, $NH_2$, $NH(C_1-C_4)$ alkyl, $N((C_1-C_4)$ alkyl$)_2$, C(O)OH, C(O)$(C_1-C_4)$ alkyl, C(O)O$(C_1-C_4)$ alkyl, C(O)NH$(C_1-C_4)$ alkyl, NHC(O)$(C_1-C_4)$ alkyl, NHC(O)O$(C_1-C_4)$ alkyl, NHC(O)NH$(C_1-C_4)$ alkyl, $(C_2-C_8)$ alkenyl, $(C_2-C_8)$ alkynyl, $C_3-C_8$ cycloalkyl, $C_3-C_8$ cycloalkenyl, heterocyclyl comprising one, two, or three 4- to 7-membered rings and 1-4 heteroatoms selected from N, O, and S, $C_6-C_{10}$ aryl, or heteroaryl comprising one or two 5- or 6-membered rings and 1-4 heteroatoms selected from N, O, and S, wherein the alkenyl, alkynyl, cycloalkyl, cycloalkenyl, heterocyclyl, aryl, or heteroaryl is optionally substituted with one or more $R_{sb2}$;

n2 is 0, 1, 2, 3, 4, 5, 6, 7, 8, 9, or 10;

each $R_{sb2}$ is independently $(C_1-C_6)$ alkyl, $(C_1-C_6)$ haloalkyl, $(C_1-C_6)$ alkoxy, $(C_1-C_6)$ haloalkoxy, $(C_2-C_6)$ alkenyl, $(C_2-C_6)$ alkynyl, halogen, nitro, CN, oxo, B(OH)$_2$, OH, SH, S$(C_1-C_6)$ alkyl, $NH_2$, $NH(C_1-C_4)$ alkyl, $N((C_1-C_4)$ alkyl$)_2$, NH$(C_6-C_{10})$ aryl, $N((C_6-C_{10})$ aryl$)_2$, C(O)OH, C(O)$(C_1-C_4)$ alkyl, C(O)O$(C_1-C_4)$ alkyl, C(O)NH$(C_1-C_4)$ alkyl, NHC(O)$(C_1-C_4)$ alkyl, NHC(O)O$(C_1-C_4)$ alkyl, NHC(O)NH$(C_1-C_4)$ alkyl, S(O)$_o$$R_6$, S(O)$_2$NH$_2$, O—$C_3-C_8$ cycloalkyl, O—$C_3-C_8$ cycloalkenyl, $C_3-C_8$ cycloalkyl, $C_3-C_8$ cycloalkenyl, heterocyclyl comprising one or two 4- to 7-membered rings and 1-4 heteroatoms selected from N, O, and S, $C_6-C_{10}$ aryl, or heteroaryl comprising one or two 5- or 6-membered rings and 1-4 heteroatoms selected from N, O, and S, wherein the cycloalkyl, cycloalkenyl, heterocyclyl, aryl, or heteroaryl is optionally substituted, and wherein the $(C_1-C_6)$ alkyl or $(C_1-C_6)$ alkoxy is optionally substituted with CN, OH, $NH_2$, $NH(C_1-C_4)$ alkyl, or $N((C_1-C_4)$ alkyl$)_2$;

each $R_4$ is independently $(C_1-C_4)$ alkyl, $(C_1-C_4)$ haloalkyl, $(C_1-C_4)$ alkoxy, $(C_1-C_4)$ haloalkoxy, halogen, OH, $NH_2$, $NH(C_1-C_4)$ alkyl, $N((C_1-C_4)$ alkyl$)_2$, C(O)OH, C(O)$(C_1-C_4)$ alkyl, C(O)O$(C_1-C_4)$ alkyl, C(O)NH$(C_1-C_4)$ alkyl, NHC(O)$(C_1-C_4)$ alkyl, NHC(O)O$(C_1-C_4)$ alkyl, or NHC(O)NH$(C_1-C_4)$ alkyl;

m is 0, 1, or 2;

$R_1$ is $(C_1-C_4)$ alkyl, $(C_1-C_4)$ haloalkyl, or $(CHR_5)_{n1}$—$R_{1a}$;

$R_{1a}$ is OH, $(C_1-C_4)$ alkoxy, $(C_1-C_4)$ haloalkoxy, O—$C_6-C_{10}$ aryl, $NH_2$, $NH(C_1-C_4)$ alkyl, $N((C_1-C_4)$ alkyl$)_2$, C(O)OH, C(O)$(C_1-C_4)$ alkyl, C(O)O$(C_1-C_4)$ alkyl, C(O)NH$(C_1-C_4)$ alkyl, NHC(O)$(C_1-C_4)$ alkyl, NHC(O)O$(C_1-C_4)$ alkyl, NHC(O)NH$(C_1-C_4)$ alkyl, $C_3-C_8$ cycloalkyl, $C_3-C_8$ cycloalkenyl, heterocyclyl comprising one or two 4- to 7-membered rings and 1-4 heteroatoms selected from N, O, and S, $C_6$-$C_{10}$ aryl, or heteroaryl comprising one or two 5- or 6-membered rings and 1-4 heteroatoms selected from N, O, and S, wherein the cycloalkyl, cycloalkenyl, heterocyclyl, aryl, or heteroaryl is optionally substituted with one or more $R_{sb1}$;

each $R_5$ is independently H or $(C_1$-$C_4)$ alkyl;

n1 is 0, 1, 2, 3, 4, 5, or 6;

$R_1'$ is H or $(C_1$-$C_4)$ alkyl;

$R_2$ is heterocyclyl comprising one or two 4- to 7-membered rings and 1-4 heteroatoms selected from N, O, and S, $C_6$-$C_{10}$ aryl, or heteroaryl comprising one or two 5- or 6-membered rings and 1-4 heteroatoms selected from N, O, and S, wherein the heterocyclyl, aryl, or heteroaryl is optionally substituted with one or more $R_{sb1}$;

each $R_{sb1}$ is independently $(C_1$-$C_4)$ alkyl, $(C_1$-$C_4)$ haloalkyl, $(C_1$-$C_4)$ alkoxy, $(C_1$-$C_4)$ haloalkoxy, halogen, CN, oxo, OH, $NH_2$, $NH(C_1$-$C_4)$ alkyl, $N((C_1$-$C_4)$ alkyl$)_2$, C(O)OH, $C(O)(C_1$-$C_4)$ alkyl, $C(O)O(C_1$-$C_4)$ alkyl, $C(O)NH(C_1$-$C_4)$ alkyl, $NHC(O)(C_1$-$C_4)$ alkyl, $NHC(O)O(C_1$-$C_4)$ alkyl, $NHC(O)NH(C_1$-$C_4)$ alkyl, $S(O)_oR_6$, $C_3$-$C_8$ cycloalkyl, $C_3$-$C_8$ cycloalkenyl, heterocyclyl comprising one or two 4- to 7-membered rings and 1-4 heteroatoms selected from N, O, and S, $C_6$-$C_{10}$ aryl, or heteroaryl comprising one or two 5- or 6-membered rings and 1-4 heteroatoms selected from N, O, and S, wherein the alkyl, alkoxy, cycloalkyl, cycloalkenyl, heterocyclyl, aryl, or heteroaryl is optionally substituted;

o is 0, 1, or 2; and $R_6$ is OH, $(C_1$-$C_4)$ alkyl, or $C_6$-$C_{10}$ aryl, wherein the aryl is optionally substituted.

In some embodiments, a compound of Formula I is of Formula Ia or Ib:

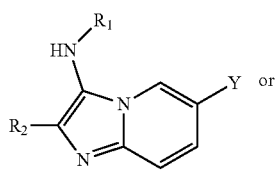

(Ia)

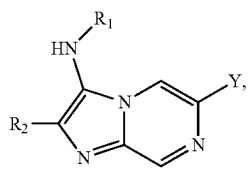

(Ib)

or a pharmaceutically acceptable salt or ester thereof, wherein Y, $R_1$, $R_{1a}$, $R_2$, $R_5$, $R_6$, $R_7$, $R_7'$, $R_{7a}$, $R_{sb1}$, $R_{sb2}$, n1, n2, and o are each as defined in Formula I.

In some embodiments, a compound of Formula I is of Formula Ic:

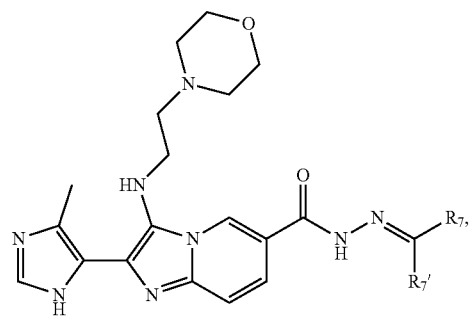

(Ic)

or a pharmaceutically acceptable salt or ester thereof, wherein $R_5$, $R_6$, $R_7$, $R_7'$, $R_{7a}$, $R_{sb2}$, n2, and o are each as defined in Formula I.

In some embodiments, where applicable for a compound of Formula I, Ia, Ib, or Ic, X is N.

In some embodiments, where applicable for a compound of Formula I, Ia, Ib, or Ic, X is $CR_3$.

In some embodiments, where applicable for a compound of Formula I, Ia, Ib, or Ic, $R_3$ is H.

In some embodiments, where applicable for a compound of Formula I, Ia, Ib, or Ic, $R_3$ is H, $(C_1$-$C_4)$ alkyl, $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1$-$C_4)$ alkoxy (e.g., methoxy, ethoxy, propoxy, i-propoxy, butoxy, i-butoxy, s-butoxy, or t-butoxy), $(C_1$-$C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), OH, $NH_2$, $NH(C_1$-$C_4)$ alkyl, $N((C_1$-$C_4)$ alkyl$)_2$, C(O)OH, $C(O)(C_1$-$C_4)$ alkyl, or $C(O)O(C_1$-$C_4)$ alkyl, wherein in each instance $(C_1$-$C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_3$ is H, $(C_1$-$C_4)$ alkyl (e.g., methyl, ethyl, propyl, i-propyl, butyl, i-butyl, s-butyl, or t-butyl), $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1$-$C_4)$ alkoxy (e.g., methoxy, ethoxy, propoxy, i-propoxy, butoxy, i-butoxy, s-butoxy, or t-butoxy), $(C_1$-$C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), OH, or $NH_2$.

In some embodiments, where applicable for a compound of Formula I, Ia, Ib, or Ic, $R_3$ is H, $(C_1$-$C_4)$ alkyl (e.g., methyl, ethyl, propyl, i-propyl, butyl, i-butyl, s-butyl, or t-butyl), $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), halogen (e.g., F, Cl, Br, or I), OH, or $NH_2$.

In some embodiments, where applicable for a compound of Formula I, Ia, Ib, or Ic, Y is H, $(C_1$-$C_4)$ alkyl, $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1$-$C_4)$ alkoxy (e.g., methoxy, ethoxy, propoxy, i-propoxy, butoxy, i-butoxy, s-butoxy, or t-butoxy), $(C_1$-$C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), OH, $NH_2$, $NH(C_1-C_4)$ alkyl, $N((C_1-C_4)$ alkyl$)_2$, C(O)OH, $C(O)(C_1-C_4)$ alkyl, or $C(O)O(C_1-C_4)$ alkyl, wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, Y is H, $(C_1-C_4)$ alkyl (e.g., methyl, ethyl, propyl, i-propyl, butyl, i-butyl, s-butyl, or t-butyl), $(C_1-C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), OH, or $NH_2$.

In some embodiments, where applicable for a compound of Formula I, Ia, Ib, or Ic, Y is H, $(C_1-C_4)$ alkyl (e.g., methyl, ethyl, propyl, i-propyl, butyl, i-butyl, s-butyl, or t-butyl), $(C_1-C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), halogen (e.g., F, Cl, Br, or I), OH, or $NH_2$.

In some embodiments, where applicable for a compound of Formula I, Ia, Ib, or Ic, Y is H, $(C_1-C_4)$ alkyl, $(C_1-C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), halogen (e.g., F, Cl, Br, or I), OH, $NH_2$, C(O)OH, or $C(O)O(C_1-C_4)$ alkyl, wherein in each instance $(C_1-C_4)$ alkyl is independently selected from methyl, ethyl, propyl, i-propyl, butyl, butyl, s-butyl, and t-butyl.

In some embodiments, where applicable for a compound of Formula I, Ia, Ib, or Ic, Y is H, $(C_1-C_4)$ alkyl, $(C_1-C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), halogen (e.g., F, Cl, Br, or I), C(O)OH, or $C(O)O(C_1-C_4)$ alkyl, wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, Y is H, $(C_1-C_4)$ alkyl, halogen (e.g., F, Cl, Br, or I), C(O)OH, or $C(O)O(C_1-C_4)$ alkyl, wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, Y is H, halogen (e.g., F, Cl, Br, or I), C(O)OH, $C(O)O(C_1-C_4)$ alkyl (e.g., methyl, ethyl, propyl, i-propyl, butyl, i-butyl, s-butyl, or t-butyl), $C(O)NHNH_2$, or $C(O)NHN=CR_7R_7'$.

In some embodiments, where applicable for a compound of Formula I, Ia, Ib, or Ic, Y is H, methyl, halogen (e.g., F, Cl, Br, or I), C(O)OH, or $C(O)OCH_3$. In some embodiments, where applicable for a compound of Formula I, Ia, Ib, or Ic, Y is H, halogen (e.g., F, Cl, Br, or I), C(O)OH, or $C(O)OCH_3$. In some embodiments, where applicable for a compound of Formula I, Ia, Ib, or Ic, Y is H, C(O)OH, or $C(O)OCH_3$.

In some embodiments, where applicable for a compound of Formula I, Ia, Ib, or Ic, Y is $C(O)NHNH_2$ or $C(O)NHN=CR_7R_7'$.

In some embodiments, where applicable for a compound of Formula I, Ia, Ib, or Ic, one of $R_7$ and $R_7'$ is H, and the other is $(C_1-C_4)$ alkyl, $(C_1-C_4)$ haloalkyl, or $(CHR_5)_{n2}$—$R_{7a}$.

In some embodiments, where applicable for a compound of Formula I, Ia, Ib, or Ic, one of $R_7$ and $R_7'$ is $(C_1-C_4)$ alkyl or $(C_1-C_4)$ haloalkyl, and the other is $(CHR_5)_{n2}$—$R_{7a}$.

In some embodiments, where applicable for a compound of Formula I, Ia, Ib, or Ic, and $R_7'$ are each independently $(CHR_5)_{n2}$—$R_{7a}$.

In some embodiments, where applicable for a compound of Formula I, Ia, Ib, or Ic, n2 is 0, 1, 2, or 3. In some embodiments, where applicable for a compound of Formula I, Ia, Ib, or Ic, n2 is 0. In some embodiments, where applicable for a compound of Formula I, Ia, Ib, or Ic, n2 is 1, 2, or 3. In some embodiments, where applicable for a compound of Formula I, Ia, Ib, or Ic, n2 is 1 or 2. In some embodiments, where applicable for a compound of Formula I, Ia, Ib, or Ic, n2 is 3, 4, 5, 6, 7, 8, 9, or 10.

In some embodiments, where applicable for a compound of Formula I, Ia, Ib, or Ic, $R_{7a}$ is OH, SH, $S(C_1-C_4)$ alkyl, $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), O—$C_6-C_{10}$ aryl (e.g., O-phenyl), $NH_2$, $NH(C_1-C_4)$ alkyl, $N((C_1-C_4)$ alkyl$)_2$, C(O)OH, $C(O)(C_1-C_4)$ alkyl, $C(O)O(C_1-C_4)$ alkyl, $C(O)NH(C_1-C_4)$ alkyl, $NHC(O)(C_1-C_4)$ alkyl, $NHC(O)O(C_1-C_4)$ alkyl, or $NHC(O)NH(C_1-C_4)$ alkyl, wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{7a}$ is OH, SH, $S(C_1-C_4)$ alkyl, $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), O—$C_6-C_{10}$ aryl (e.g., O-phenyl), $C(O)(C_1-C_4)$ alkyl, $C(O)O(C_1-C_4)$ alkyl, $C_3-C_8$ cycloalkyl (e.g., cyclopropyl, cyclobutyl, cyclopentyl, cyclohexyl, cyclopentyl, or cyclooctyl), $C_3-C_8$ cycloalkenyl (e.g., cyclopropenyl, cyclobutenyl, cyclopentenyl, cyclohexenyl, cycloheptenyl, or cyclooctenyl), heterocyclyl comprising one or two 4- to 7-membered rings and 1-4 heteroatoms selected from N, O, and S, $C_6-C_{10}$ aryl (e.g., phenyl), or heteroaryl comprising one or two 5- or 6-membered rings and 1-4 heteroatoms selected from N, O, and S, wherein the cycloalkyl, cycloalkenyl, heterocyclyl, aryl, or heteroaryl is optionally substituted with one or more $R_{sb2}$, and wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{7a}$ is $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), $C(O)(C_1-C_4)$ alkyl, $C(O)O(C_1-C_4)$ alkyl, $C_3-C_8$ cycloalkyl (e.g., cyclopropyl, cyclobutyl, cyclopentyl, cyclohexyl, cyclopentyl, or cyclooctyl), heterocyclyl comprising one or two 4- to 7-membered rings and 1-4 heteroatoms selected from N, O, and S, $C_6-C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb2}$, and wherein in each instance ($C_1$-$C_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{7a}$ is ($C_1$-$C_4$) alkoxy (e.g., methoxy, ethoxy, propoxy, i-propoxy, butoxy, i-butoxy, s-butoxy, or t-butoxy), O—$C_6$-$C_{10}$ aryl (e.g., O-phenyl), C(O)O($C_1$-$C_4$) alkyl, $C_3$-$C_8$ cycloalkyl (e.g., cyclopropyl, cyclobutyl, cyclopentyl, cyclohexyl, cyclopentyl, or cyclooctyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb2}$, 1 and wherein in each instance ($C_1$-$C_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{7a}$ is $C_3$-$C_8$ cycloalkyl (e.g., cyclopropyl, cyclobutyl, cyclopentyl, cyclohexyl, cyclopentyl, or cyclooctyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb2}$.

In some embodiments, where applicable for a compound of Formula I, Ia, Ib, or Ic, $R_{7a}$ is $C_3$-$C_8$ cycloalkyl (e.g., cyclopropyl, cyclobutyl, cyclopentyl, cyclohexyl, cyclopentyl, or cyclooctyl), heterocyclyl comprising one 4- to 7-membered ring and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb2}$.

In some embodiments, where applicable for a compound of Formula I, Ia, Ib, or Ic, $R_{7a}$ is ($C_2$-$C_8$) alkenyl, including straight-chain or branched alkenyl. In some embodiments, where applicable for a compound of Formula I, Ia, Ib, or Ic, $R_{7a}$ is ($C_2$-$C_8$) alkenyl, including ethenyl, propenyl, i-propenyl, butenyl, i-butenyl, s-butenyl, pentenyl, hexenyl, heptenyl, and octenyl, each of which can be straight-chain or branched.

In some embodiments, where applicable for a compound of Formula I, Ia, Ib, or Ic, $R_{7a}$ is ($C_2$-$C_8$) alkynyl, including straight-chain or branched alkynyl. In some embodiments, where applicable for a compound of Formula I, Ia, Ib, or Ic, $R_{7a}$ is ($C_2$-$C_8$) alkynyl, including ethynyl, propynyl, i-propynyl, butynyl, i-butynyl, s-butynyl, pentynyl, hexynyl, heptynyl, and octynyl, each of which can be straight-chain or branched.

In some embodiments, where applicable for a compound of Formula I, Ia, Ib, or Ic, $R_7$ and $R_7'$, together with the carbon atom to which they are attached, form $C_3$-$C_8$ cycloalkyl, $C_3$-$C_8$ cycloalkenyl, or heterocyclyl comprising one, two, or three 4- to 7-membered rings and 1-4 heteroatoms selected from N, O, and S, wherein the cycloalkyl, cycloalkenyl, or heterocyclyl is optionally substituted with one or more $R_{sb2}$.

In some embodiments, where applicable for a compound of Formula I, Ia, Ib, or Ic, $R_7$ and $R_7'$ each independently correspond to the groups shown in FIGS. 11A-11D without the oxygen atom in the C=O moiety, i.e., the carbon atom in the C=O moiety forms a double bond with the nitrogen atom indicated below.

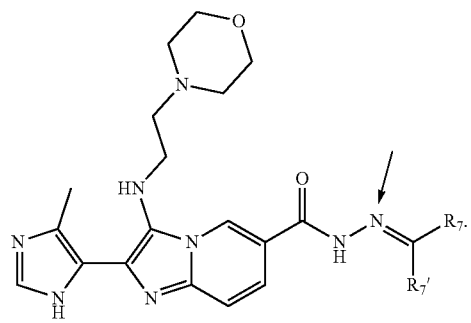

In some embodiments, where applicable for a compound of Formula I, Ia, Ib, or Ic, at least one $R_{sb2}$ is ($C_1$-$C_6$) alkyl (e.g., methyl, ethyl, propyl, i-propyl, butyl, i-butyl, s-butyl, t-butyl, pentyl, or hexyl), ($C_1$-$C_6$) haloalkyl (e.g., methyl, ethyl, propyl, i-propyl, butyl, i-butyl, s-butyl, t-butyl, pentyl, or hexyl, each of which is substituted with one or more halogen (e.g., F, Cl, Br, or I)), ($C_1$-$C_6$) alkoxy (e.g., methoxy, ethoxy, propoxy, i-propoxy, butoxy, i-butoxy, s-butoxy, t-butoxy, pentoxy, or hexanoxy), ($C_1$-$C_6$) haloalkoxy (e.g., methoxy, ethoxy, propoxy, i-propoxy, butoxy, i-butoxy, s-butoxy, t-butoxy, pentoxy, or hexanoxy, each of which is substituted with one or more halogen (e.g., F, Cl, Br, or I)), halogen (e.g., F, Cl, Br, or I), nitro, CN, oxo, B(OH)$_2$, OH, SH, S($C_1$-$C_6$) alkyl (wherein the alkyl is methyl, ethyl, propyl, i-propyl, butyl, i-butyl, s-butyl, t-butyl, pentyl, or hexyl), S(O)$_2$NH$_2$, NH$_2$, NH($C_1$-$C_4$) alkyl, N(($C_1$-$C_4$) alkyl)$_2$, NH($C_6$-$C_{10}$) aryl, N(($C_6$-$C_{10}$) aryl)$_2$, C(O)OH, C(O)($C_1$-$C_4$) alkyl, or C(O)O($C_1$-$C_4$) alkyl, wherein in each instance ($C_1$-$C_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one $R_{sb2}$ is ($C_1$-$C_6$) alkyl (e.g., methyl, ethyl, propyl, i-propyl, butyl, i-butyl, s-butyl, t-butyl, pentyl, or hexyl), ($C_1$-$C_6$) haloalkyl (e.g., methyl, ethyl, propyl, i-propyl, butyl, i-butyl, s-butyl, t-butyl, pentyl, or hexyl, each of which is substituted with one or more halogen (e.g., F, Cl, Br, or I)), ($C_1$-$C_6$) alkoxy (e.g., methoxy, ethoxy, propoxy, i-propoxy, butoxy, i-butoxy, s-butoxy, t-butoxy, pentoxy, or hexanoxy), ($C_1$-$C_6$) haloalkoxy (e.g., methoxy, ethoxy, propoxy, i-propoxy, butoxy, i-butoxy, s-butoxy, t-butoxy, pentoxy, or hexanoxy, each of which is substituted with one or more halogen (e.g., F, Cl, Br, or I)), halogen (e.g., F, Cl, Br, or I), nitro, CN, oxo, B(OH)$_2$, OH, SH, S($C_1$-$C_6$) alkyl (wherein the alkyl is methyl, ethyl, propyl, i-propyl, butyl, i-butyl, s-butyl, t-butyl, pentyl, or hexyl), S(O)$_2$NH$_2$, C(O)OH, C(O)($C_1$-$C_4$) alkyl, or C(O)O ($C_1$-$C_4$) alkyl, wherein in each instance ($C_1$-$C_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one $R_{sb2}$ is ($C_1$-$C_6$) alkyl (e.g., methyl, ethyl, propyl, i-propyl, butyl, i-butyl, s-butyl, t-butyl, pentyl, or hexyl), ($C_1$-$C_6$) haloalkyl (e.g., methyl, ethyl, propyl, i-propyl, butyl, i-butyl, s-butyl, t-butyl, pentyl, or hexyl, each of which is substituted with one or more halogen (e.g., F, Cl, Br, or I)), ($C_1$-$C_6$) alkoxy (e.g., methoxy, ethoxy, propoxy, i-propoxy, butoxy, i-butoxy, s-butoxy, t-butoxy, pentoxy, or hexanoxy), ($C_1$-$C_6$) haloalkoxy (e.g., methoxy, ethoxy, propoxy, i-propoxy, butoxy, i-butoxy, s-butoxy, t-butoxy, pentoxy, or hexanoxy, each of which is substituted with one or more halogen (e.g., F, Cl, Br, or I)), halogen (e.g., F, Cl, Br, or I), nitro, CN, oxo, $B(OH)_2$, OH, SH, $S(C_1$-$C_6)$ alkyl (wherein the alkyl is methyl, ethyl, propyl, i-propyl, butyl, i-butyl, s-butyl, t-butyl, pentyl, or hexyl), $S(O)_2NH_2$, $C(O)(C_1$-$C_4)$ alkyl, $C(O)O(C_1$-$C_4)$ alkyl, or $S(O)_oR_6$, wherein in each instance $(C_1$-$C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one $R_{sb2}$ is $(C_1$-$C_6)$ alkyl (e.g., methyl, ethyl, propyl, i-propyl, butyl, i-butyl, s-butyl, t-butyl, pentyl, or hexyl), $(C_1$-$C_6)$ haloalkyl (e.g., methyl, ethyl, propyl, i-propyl, butyl, i-butyl, s-butyl, t-butyl, pentyl, or hexyl, each of which is substituted with one or more halogen (e.g., F, Cl, Br, or I)), $(C_1$-$C_6)$ alkoxy (e.g., methoxy, ethoxy, propoxy, i-propoxy, butoxy, i-butoxy, s-butoxy, t-butoxy, pentoxy, or hexanoxy), $(C_1$-$C_6)$ haloalkoxy (e.g., methoxy, ethoxy, propoxy, i-propoxy, butoxy, i-butoxy, s-butoxy, t-butoxy, pentoxy, or hexanoxy, each of which is substituted with one or more halogen (e.g., F, Cl, Br, or I)).

In some embodiments, where applicable for a compound of Formula I, Ia, Ib, or Ic, at least one $R_{sb2}$ is nitro, CN, oxo, $B(OH)_2$, OH, SH, $S(C_1$-$C_6)$ alkyl (e.g., methyl, ethyl, propyl, i-propyl, butyl, i-butyl, s-butyl, t-butyl, pentyl, or hexyl), $C(O)(C_1$-$C_4)$ alkyl, $C(O)O(C_1$-$C_4)$ alkyl, or $S(O)_oR_6$, wherein in each instance $(C_1$-$C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one $R_{sb2}$ is O—$C_3$-$C_8$ cycloalkyl (wherein the cycloalkyl is cyclopropyl, cyclobutyl, cyclopentyl, cyclohexyl, cyclopentyl, or cyclooctyl), $C_3$-$C_8$ cycloalkyl (e.g., cyclopropyl, cyclobutyl, cyclopentyl, cyclohexyl, cyclopentyl, or cyclooctyl), O—$C_3$-$C_8$ cycloalkenyl (wherein the cycloalkenyl is cyclopropenyl, cyclobutenyl, cyclopentenyl, cyclohexenyl, cycloheptenyl, or cyclooctenyl), $C_3$-$C_8$ cycloalkenyl (e.g., cyclopropenyl, cyclobutenyl, cyclopentenyl, cyclohexenyl, cycloheptenyl, or cyclooctenyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, each of which is optionally substituted with one or more substituents independently selected from $(C_1$-$C_4)$ alkyl, $(C_1$-$C_4)$ alkoxy (e.g., methoxy, ethoxy, propoxy, i-propoxy, butoxy, i-butoxy, s-butoxy, or t-butoxy), halogen (e.g., F, Cl, Br, or I), oxo, $S(O)_2NH_2$, C(O)OH, $C(O)(C_1$-$C_4)$ alkyl, and $C(O)O(C_1$-$C_4)$ alkyl, wherein in each instance $(C_1$-$C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one $R_{sb2}$ is $(C_2$-$C_6)$ alkenyl, including straight-chain or branched alkenyl. In some embodiments, where applicable for a compound of Formula I, Ia, Ib, or Ic, $R_{sb2}$ is $(C_2$-$C_6)$ alkenyl, including ethenyl, propenyl, i-propenyl, butenyl, i-butenyl, s-butenyl, pentenyl, and hexenyl, each of which can be straight-chain or branched.

In some embodiments, where applicable for a compound of Formula I, Ia, Ib, or Ic, $R_{sb2}$ is $(C_2$-$C_6)$ alkynyl, including straight-chain or branched alkynyl. In some embodiments, where applicable for a compound of Formula I, Ia, Ib, or Ic, $R_{sb2}$ is $(C_2$-$C_2)$ alkynyl, including ethynyl, propynyl, i-propynyl, butynyl, i-butynyl, s-butynyl, pentynyl, and hexynyl, each of which can be straight-chain or branched.

In some embodiments, where applicable for a compound of Formula I, Ia, Ib, or Ic, m is 0. In some embodiments, where applicable for a compound of Formula I, Ia, Ib, or Ic, m is 1 or 2. In some embodiments, where applicable for a compound of Formula I, Ia, Ib, or Ic, m is 1.

In some embodiments, where applicable for a compound of Formula I, Ia, Ib, or Ic, each $R_4$ is independently $(C_1$-$C_4)$ alkyl, $(C_1$-$C_4)$ haloalkyl (e.g., methyl, ethyl, propyl, propyl, butyl, i-butyl, s-butyl, or t-butyl, each of which is substituted with one or more halogen (e.g., F, Cl, Br, or I)), $(C_1$-$C_4)$ alkoxy (e.g., methoxy, ethoxy, propoxy, i-propoxy, butoxy, i-butoxy, s-butoxy, or t-butoxy), $(C_1$-$C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), OH, $NH_2$, $NH(C_1$-$C_4)$ alkyl, $N((C_1$-$C_4)$ alkyl$)_2$, C(O)OH, $C(O)(C_1$-$C_4)$ alkyl, or $C(O)O(C_1$-$C_4)$ alkyl, wherein in each instance $(C_1$-$C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, each $R_4$ is independently $(C_1$-$C_4)$ alkyl (e.g., methyl, ethyl, propyl, i-propyl, butyl, i-butyl, s-butyl, or t-butyl), $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1$-$C_4)$ alkoxy (e.g., methoxy, ethoxy, propoxy, i-propoxy, butoxy, i-butoxy, s-butoxy, or t-butoxy), $(C_1$-$C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), OH, or $NH_2$.

In some embodiments, where applicable for a compound of Formula I, Ia, Ib, or Ic, each $R_4$ is independently $(C_1$-$C_4)$ alkyl (e.g., methyl, ethyl, propyl, i-propyl, butyl, i-butyl, s-butyl, or t-butyl), $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), halogen (e.g., F, Cl, Br, or I), OH, or $NH_2$.

In some embodiments, where applicable for a compound of Formula I, Ia, Ib, or Ic, $R_1$ is $(C_1$-$C_4)$ alkyl (e.g., methyl, ethyl, propyl, i-propyl, butyl, i-butyl, s-butyl, or t-butyl) or $(C_1$-$C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)). In some embodiments, where applicable for a compound of Formula I, Ia, Ib, or Ic, $R_1$ is $(C_1$-$C_4)$ alkyl (e.g., methyl, ethyl, propyl, i-propyl, butyl, i-butyl, s-butyl, or t-butyl). In some embodiments, where applicable for a compound of Formula I, Ia, Ib, or Ic, $R_1$ is t-butyl.

In some embodiments, where applicable for a compound of Formula I, Ia, Ib, or Ic, $R_1$ is $(C_1$-$C_4)$ alkyl (e.g., methyl, ethyl, propyl, i-propyl, butyl, i-butyl, s-butyl, or t-butyl) or $(CHR_5)_n$—$R_{1a}$. In some embodiments, where applicable for a compound of Formula I, Ia, Ib, or Ic, $R_1$ is t-butyl) or $(CHR_5)_n$—$R_{1a}$.

In some embodiments, where applicable for a compound of Formula I, Ia, Ib, or Ic, n1 is 0, 1, 2, or 3. In some embodiments, where applicable for a compound of Formula I, Ia, Ib, or Ic, n1 is 0. In some embodiments, where applicable for a compound of Formula I, Ia, Ib, or Ic, n1 is 1, 2, or 3. In some embodiments, where applicable for a compound of Formula I, Ia, Ib, or Ic, n1 is 1 or 2.

In some embodiments, where applicable for a compound of Formula I, Ia, Ib, or Ic, each $R_5$ is H. In some embodiments, where applicable for a compound of Formula I, Ia, Ib, or Ic, at least one $R_5$ is $(C_1-C_4)$ alkyl (e.g., methyl, ethyl, propyl, i-propyl, butyl, i-butyl, s-butyl, or t-butyl).

In some embodiments, where applicable for a compound of Formula I, Ia, Ib, or Ic, $R_{1a}$ is OH, $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), O—$C_6$-$C_{10}$ aryl (e.g., O-phenyl), $NH_2$, $NH(C_1-C_4)$ alkyl, $N((C_1-C_4)$ alkyl$)_2$, C(O)OH, $C(O)(C_1-C_4)$ alkyl, $C(O)O(C_1-C_4)$ alkyl, $C(O)NH(C_1-C_4)$ alkyl, $NHC(O)(C_1-C_4)$ alkyl, $NHC(O)O(C_1-C_4)$ alkyl, or $NHC(O)NH(C_1-C_4)$ alkyl, wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{1a}$ is OH, $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), O—$C_6$-$C_{10}$ aryl (e.g., O-phenyl), $C(O)(C_1-C_4)$ alkyl, $C(O)O(C_1-C_4)$ alkyl, $C_3$-$C_8$ cycloalkyl (e.g., cyclopropyl, cyclobutyl, cyclopentyl, cyclohexyl, cyclopentyl, or cyclooctyl), $C_3$-$C_8$ cycloalkenyl (e.g., cyclopropenyl, cyclobutenyl, cyclopentenyl, cyclohexenyl, cycloheptenyl, or cyclooctenyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, cycloalkenyl, heterocyclyl, aryl, or heteroaryl is optionally substituted with one or more $R_{sb1}$, and wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{1a}$ is $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), $C(O)(C_1-C_4)$ alkyl, C(O)O $(C_1-C_4)$ alkyl, $C_3$-$C_8$ cycloalkyl (e.g., cyclopropyl, cyclobutyl, cyclopentyl, cyclohexyl, cyclopentyl, or cyclooctyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb1}$, and wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{1a}$ is $(C_1-C_4)$ alkoxy (e.g., methoxy, ethoxy, propoxy, i-propoxy, butoxy, i-butoxy, s-butoxy, or t-butoxy), O—$C_6$-$C_{10}$ aryl (e.g., O-phenyl), $C(O)O(C_1-C_4)$ alkyl, $C_3$-$C_8$ cycloalkyl (e.g., cyclopropyl, cyclobutyl, cyclopentyl, cyclohexyl, cyclopentyl, or cyclooctyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb1}$, and wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, $R_{1a}$ is $C_3$-$C_8$ cycloalkyl (e.g., cyclopropyl, cyclobutyl, cyclopentyl, cyclohexyl, cyclopentyl, or cyclooctyl), heterocyclyl comprising one or two 4- to 7-membered rings and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb1}$.

In some embodiments, where applicable for a compound of Formula I, Ia, Ib, or Ic, $R_{1a}$ is $C_3$-$C_8$ cycloalkyl (e.g., cyclopropyl, cyclobutyl, cyclopentyl, cyclohexyl, cyclopentyl, or cyclooctyl), heterocyclyl comprising one 4- to 7-membered ring and 1-4 heteroatoms selected from N, O, and S, $C_6$-$C_{10}$ aryl (e.g., phenyl), or heteroaryl comprising one or two 5- or 6-membered rings and 1-4 heteroatoms selected from N, O, and S, wherein the cycloalkyl, heterocyclyl, aryl, or heteroaryl is optionally substituted with one or more $R_{sb1}$.

In some embodiments, where applicable for a compound of Formula I, Ia, Ib, or Ic, is H. In some embodiments, where applicable for a compound of Formula I, Ia, Ib, or Ic, $R_1'$ is $(C_1-C_4)$ alkyl (e.g., methyl, ethyl, propyl, i-propyl, butyl, i-butyl, s-butyl, or t-butyl).

In some embodiments, where applicable for a compound of Formula I, Ia, Ib, or Ic, $R_2$ is heterocyclyl comprising one or two 4- to 7-membered rings and 1-4 heteroatoms selected from N, O, and S, or heteroaryl comprising one or two 5- or 6-membered rings and 1-4 heteroatoms selected from N, O, and S, wherein the heterocyclyl or heteroaryl is optionally substituted with one or more $R_{sb1}$.

In some embodiments, where applicable for a compound of Formula I, Ia, Ib, or Ic, $R_2$ is $C_6$-$C_{10}$ aryl (e.g., phenyl) or heteroaryl comprising one or two 5- or 6-membered rings and 1-4 heteroatoms selected from N, O, and S, wherein the aryl or heteroaryl is optionally substituted with one or more $R_{sb1}$.

In some embodiments, where applicable for a compound of Formula I, Ia, Ib, or Ic, $R_2$ is heteroaryl comprising one or two 5- or 6-membered rings and 1-4 heteroatoms selected from N, O, and S, and is optionally substituted with one or more $R_{sb1}$.

In some embodiments, where applicable for a compound of Formula I, Ia, Ib, or Ic, at least one $R_{sb1}$ is $(C_1-C_4)$ alkyl, $(C_1-C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1-C_4)$ alkoxy (e.g., methoxy, ethoxy, propoxy, i-propoxy, butoxy, i-butoxy, s-butoxy, or t-butoxy), $(C_1-C_4)$ haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), CN, oxo, OH, $NH_2$, $NH(C_1-C_4)$ alkyl, $N((C_1-C_4)$ alkyl$)_2$, C(O)OH, $C(O)(C_1-C_4)$ alkyl, or $C(O)O(C_1-C_4)$ alkyl, wherein in each instance $(C_1-C_4)$ alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one $R_{sb1}$ is $(C_1-C_4)$ alkyl, $(C_1-C_4)$ haloalkyl (e.g., methyl, ethyl, propyl, i-propyl, butyl, i-butyl, s-butyl, or t-butyl, each of which is substituted with one or more halogen (e.g., F, Cl, Br, or I)), $(C_1-C_4)$ alkoxy (e.g., methoxy, ethoxy, propoxy, i-propoxy, butoxy, i-butoxy, s-butoxy, or t-butoxy), (C$_1$-C$_4$) haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), CN, oxo, OH, C(O)OH, C(O)(C$_1$-C$_4$) alkyl, or C(O)O(C$_1$-C$_4$) alkyl, wherein in each instance (C$_1$-C$_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one R$_{sb1}$ is (C$_1$-C$_4$) alkyl, (C$_1$-C$_4$) haloalkyl (e.g., methyl, ethyl, propyl, i-propyl, butyl, i-butyl, s-butyl, or t-butyl, each of which is substituted with one or more halogen (e.g., F, Cl, Br, or I)), (C$_1$-C$_4$) alkoxy (e.g., methoxy, ethoxy, propoxy, i-propoxy, butoxy, i-butoxy, s-butoxy, or t-butoxy), (C$_1$-C$_4$) haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)), halogen (e.g., F, Cl, Br, or I), CN, oxo, C(O)(C$_1$-C$_4$) alkyl, C(O)O(C$_1$-C$_4$) alkyl, or S(O)$_o$R$_6$, wherein in each instance (C$_1$-C$_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one R$_{sb1}$ is (C$_1$-C$_4$) alkyl (e.g., methyl, ethyl, propyl, i-propyl, butyl, i-butyl, s-butyl, or t-butyl), (C$_1$-C$_4$) haloalkyl (e.g., methyl, ethyl, propyl, i-propyl, butyl, i-butyl, s-butyl, or t-butyl, each of which is substituted with one or more halogen (e.g., F, Cl, Br, or I)), (C$_1$-C$_4$) alkoxy (e.g., methoxy, ethoxy, propoxy, i-propoxy, butoxy, i-butoxy, s-butoxy, or t-butoxy), or (C$_1$-C$_4$) haloalkoxy (e.g., methoxy, ethoxy, propoxy, i-propoxy, butoxy, i-butoxy, s-butoxy, or t-butoxy, each of which is substituted with one or more halogen (e.g., F, Cl, Br, or I)).

In some embodiments, where applicable for a compound of Formula I, Ia, Ib, or Ic, at least one R$_{sb1}$ is CN, oxo, C(O)(C$_1$-C$_4$) alkyl, C(O)O(C$_1$-C$_4$) alkyl, or S(O)$_o$R$_6$, wherein in each instance (C$_1$-C$_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, at least one R$_{sb1}$ is C$_3$-C$_8$ cycloalkyl (e.g., cyclopropyl, cyclobutyl, cyclopentyl, cyclohexyl, cyclopentyl, or cyclooctyl), C$_3$-C$_8$ cycloalkenyl (e.g., cyclopropenyl, cyclobutenyl, cyclopentenyl, cyclohexenyl, cycloheptenyl, or cyclooctenyl), heterocyclyl comprising one or two 4- to 7-membered rings and 1-4 heteroatoms selected from N, O, and S, C$_6$-C$_{10}$ aryl (e.g., phenyl), or heteroaryl comprising one or two 5- or 6-membered rings and 1-4 heteroatoms selected from N, O, and S, each of which is optionally substituted with one or more substituents independently selected from (C$_1$-C$_4$) alkyl, (C$_1$-C$_4$) alkoxy (e.g., methoxy, ethoxy, propoxy, i-propoxy, butoxy, i-butoxy, s-butoxy, or t-butoxy), halogen (e.g., F, Cl, Br, or I), oxo, C(O)OH, C(O)(C$_1$-C$_4$) alkyl, and C(O)O(C$_1$-C$_4$) alkyl, wherein in each instance (C$_1$-C$_4$) alkyl is independently selected from methyl, ethyl, propyl, i-propyl, butyl, i-butyl, s-butyl, and t-butyl.

In some embodiments, where applicable for a compound of Formula I, Ia, Ib, or Ic, o is 0. In some embodiments, where applicable for a compound of Formula I, Ia, Ib, or Ic, o is 1 or 2. In some embodiments, where applicable for a compound of Formula I, Ia, Ib, or Ic, o is 1. In some embodiments, where applicable for a compound of Formula I, Ia, Ib, or Ic, o is 2.

In some embodiments, where applicable for a compound of Formula I, Ia, Ib, or Ic, R$_6$ is (C$_1$-C$_4$) alkyl (e.g., methyl, ethyl, propyl, i-propyl, butyl, i-butyl, s-butyl, or t-butyl).

In some embodiments, where applicable for a compound of Formula I, Ia, Ib, or Ic, R$_6$ is C$_6$-C$_{10}$ aryl (e.g., phenyl), which is optionally substituted with one or more substituents independently selected from (C$_1$-C$_4$) alkyl (e.g., methyl, ethyl, propyl, i-propyl, butyl, i-butyl, s-butyl, or t-butyl), (C$_1$-C$_4$) alkoxy (e.g., methoxy, ethoxy, propoxy, i-propoxy, butoxy, i-butoxy, s-butoxy, or t-butoxy), halogen (e.g., F, Cl, Br, or I), and oxo.

Any of the groups described herein for any of X, Y, R$_1$, R$_1$', R$_{1a}$, R$_2$, R$_3$, R$_4$, R$_5$, R$_6$, R$_7$, R$_7$', R$_{7a}$, R$_{sb1}$, R$_{sb2}$, n1, n2, and o can be combined with any of the groups described herein for one or more of the remainder of X, Y, R$_1$, R$_1$', R$_{1a}$, R$_2$, R$_3$, R$_4$, R$_5$, R$_6$, R$_7$, R$_7$', R$_{7a}$, R$_{sb1}$, R$_{sb2}$, n1, n2, and o.

In some embodiments, a compound of Formula I does not have the following structures:

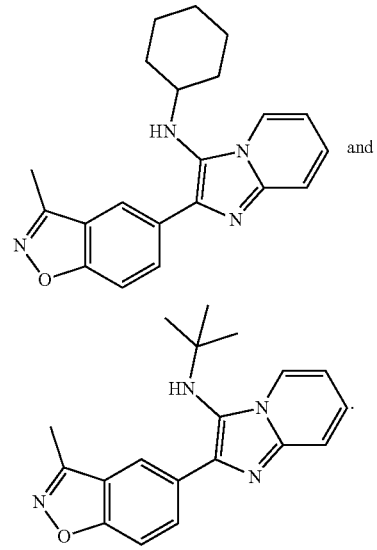

and

Non-limiting illustrative compounds of the application are listed in Table 1.

TABLE 1

| Cmpd No. | Structure |
|---|---|
| 1 (A5) | |
| 2 (A6) | 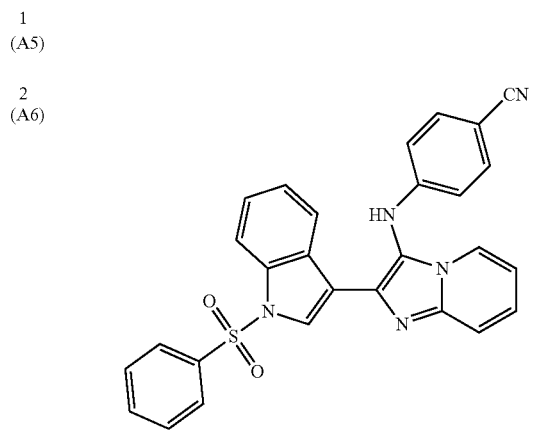 |

TABLE 1-continued

| Cmpd No. | Structure |
|---|---|
| 3 (A9) | |
| 4 (B1) | |
| 5 (B4) | |
| 6 (B4') | |
| 7 (B6) | |
| 8 (B8) | 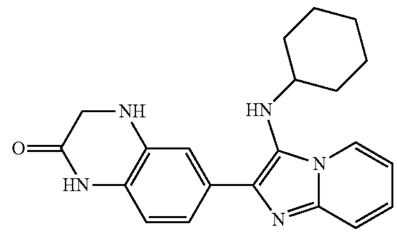 [SMILES: O=C1CNc2cc(-c3nc4ccccn4c3NC3CCCCC3)ccc2N1] |
| 9 (B9) | 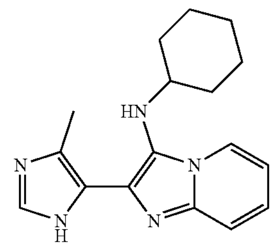 [SMILES: Cc1nc[nH]c1-c1nc2ccccn2c1NC1CCCCC1] |
| 10 (B9') | 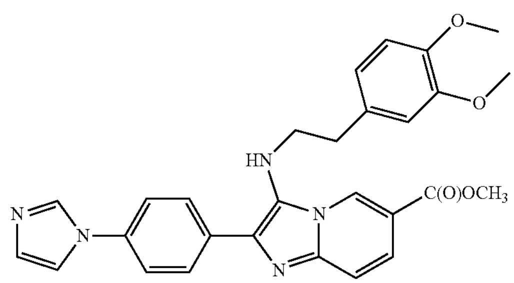 |
| 11 (C7) | 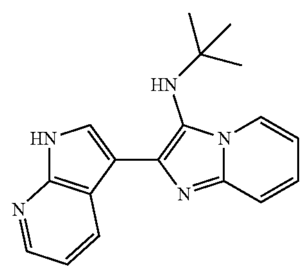 [SMILES: CC(C)(C)Nc1c(-c2c[nH]c3ncccc23)nc2ccccn12] |
| 12 (C8) | 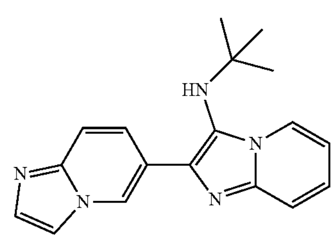 [SMILES: CC(C)(C)Nc1c(-c2ccc3nccn3c2)nc2ccccn12] |
| 13 (C9) | 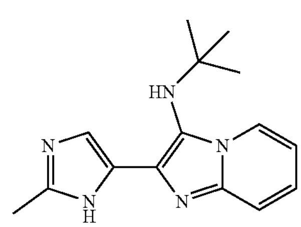 [SMILES: Cc1ncc(-c2nc3ccccn3c2NC(C)(C)C)[nH]1] |

TABLE 1-continued

| Cmpd No. | Structure |
|---|---|
| 14 (C11) | 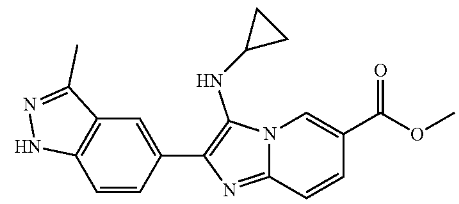 [SMILES: COC(=O)c1ccc2nc(-c3ccc4[nH]nc(C)c4c3)c(NC3CC3)n2c1] |
| 15 (C12) | 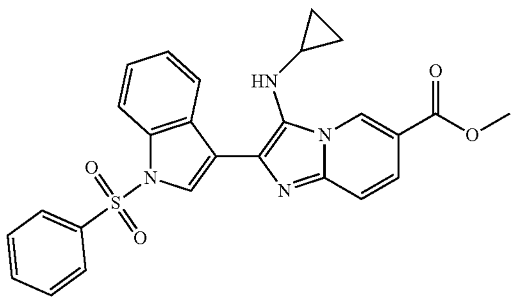 [SMILES: COC(=O)c1ccc2nc(-c3cn(S(=O)(=O)c4ccccc4)c4ccccc34)c(NC3CC3)n2c1] |
| 16 (E6) | 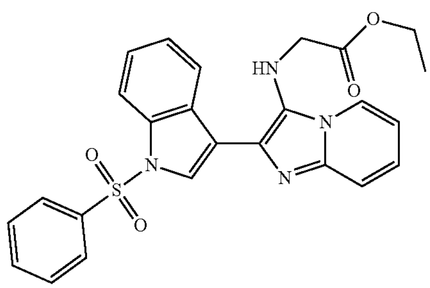 [SMILES: CCOC(=O)CNc1c(-c2cn(S(=O)(=O)c3ccccc3)c3ccccc23)nc2ccccn12] |
| 17 (E11) | 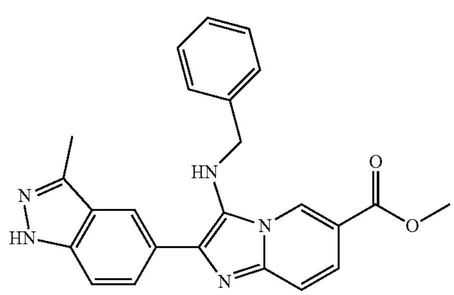 [SMILES: COC(=O)c1ccc2nc(-c3ccc4[nH]nc(C)c4c3)c(NCc3ccccc3)n2c1] |
| 18 (E12) | 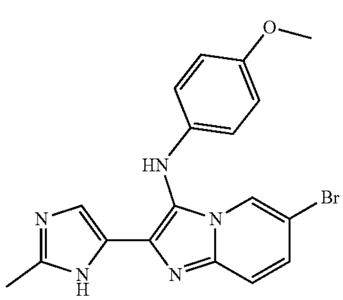 [SMILES: COc1ccc(Nc2c(-c3cnc(C)[nH]3)nc3ccc(Br)cn23)cc1] |
| 19 (E12') | |
| 20 (F8) | |
| 21 (F9) | |
| 22 (F12) | |
| 23 (F12') | |

TABLE 1-continued
| Cmpd No. | Structure |
|---|---|
| 24 | 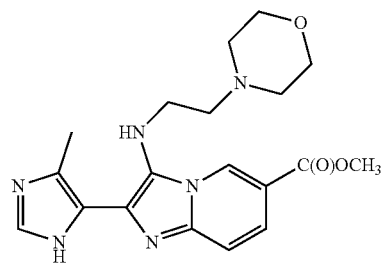 |
| 25 | 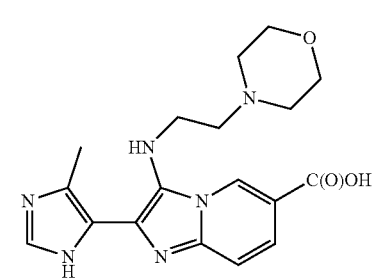 |
| 26 | 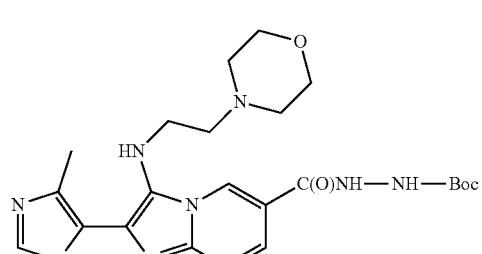 |
| 27 | 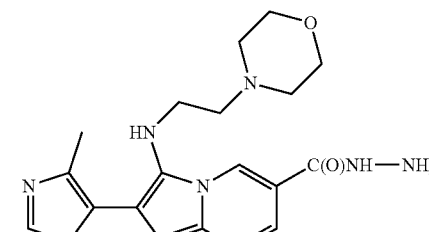 |
| 28 | 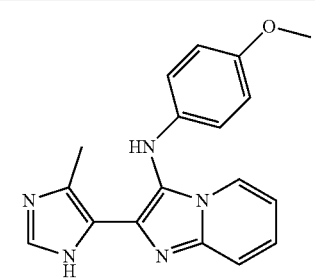 [SMILES: COc1ccc(Nc2c(-c3[nH]cnc3C)nc3ccccn23)cc1] |
| 29 | 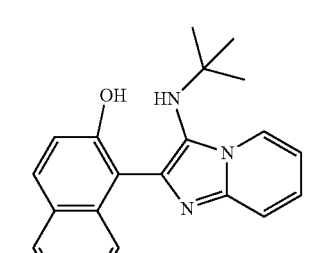 |
| 30 | 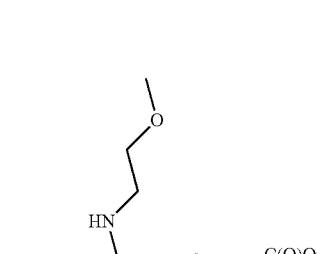 |
| 31 | 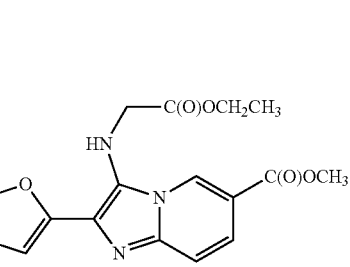 |
Non-limiting illustrative compounds of the application are also listed in Tables 2a-2d.

TABLE 2a

|   | 1 | 2 | 3 | 4 | 5 | 6 |
|---|---|---|---|---|---|---|
| A | A1 + B1 + I1 | A1 + B1 + I2 | A1 + B1 + I3 | A1 + B1 + I4 | A1 + B1 + I5 | A1 + B1 + I6 |
| B | A1 + B2 + I1 | A1 + B2 + I2 | A1 + B2 + I3 | A1 + B2 + I4 | A1 + B2 + I5 | A1 + B2 + I6 |
| C | A1 + B3 + I1 | A1 + B3 + I2 | A1 + B3 + I3 | A1 + B3 + I4 | A1 + B3 + I5 | A1 + B3 + I6 |
| D | A1 + B4 + I1 | A1 + B4 + I2 | A1 + B4 + I3 | A1 + B4 + I4 | A1 + B4 + I5 | A1 + B4 + I6 |
| E | A3 + B1 + I1 | A3 + B1 + I2 | A3 + B1 + I3 | A3 + B1 + I4 | A3 + B1 + I5 | A3 + B1 + I6 |
| F | A3 + B2 + I1 | A3 + B2 + I2 | A3 + B2 + I3 | A3 + B2 + I4 | A3 + B2 + I5 | A3 + B2 + I6 |
| G | A3 + B3 + I1 | A3 + B3 + I2 | A3 + B3 + I3 | A3 + B3 + I4 | A3 + B3 + I5 | A3 + B3 + I6 |
| H | A3 + B4 + I1 | A3 + B4 + I2 | A3 + B4 + I3 | A3 + B4 + I4 | A3 + B4 + I5 | A3 + B4 + I6 |

|   | 7 | 8 | 9 | 10 | 11 | 12 |
|---|---|---|---|---|---|---|
| A | A2 + B1 + I1 | A2 + B1 + I2 | A2 + B1 + I3 | A2 + B1 + I4 | A2 + B1 + I5 | A2 + B1 + I6 |
| B | A2 + B2 + I1 | A2 + B2 + I2 | A2 + B2 + I3 | A2 + B2 + I4 | A2 + B2 + I5 | A2 + B2 + I6 |
| C | A2 + B3 + I1 | A2 + B3 + I2 | A2 + B3 + I3 | A2 + B3 + I4 | A2 + B3 + I5 | A2 + B3 + I6 |
| D | A2 + B4 + I1 | A2 + B4 + I2 | A2 + B4 + I3 | A2 + B4 + I4 | A2 + B4 + I5 | A2 + B4 + I6 |
| E | A4 + B1 + I1 | A4 + B1 + I2 | A4 + B1 + I3 | A4 + B1 + I4 | A4 + B1 + I5 | A4 + B1 + I6 |

TABLE 2a-continued
| | | | | | | |
|---|---|---|---|---|---|---|
| F | A4 + B2 + I1 | A4 + B2 + I2 | A4 + B2 + I3 | A4 + B2 + I4 | A4 + B2 + I5 | A4 + B2 + I6 |
| G | A4 + B3 + I1 | A4 + B3 + I2 | A4 + B3 + I3 | A4 + B3 + I4 | A4 + B3 + I5 | A4 + B3 + I6 |
TABLE 2b
A1
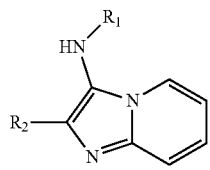
A2
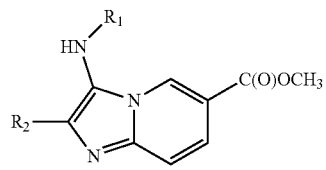
R1
I1
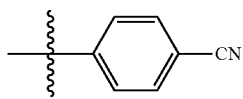
I2
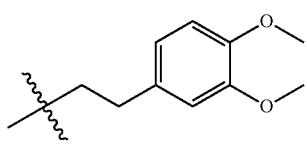 [SMILES: *CCc1ccc(OC)c(OC)c1]
I3
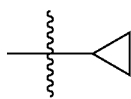 [SMILES: *C1CC1]
I4
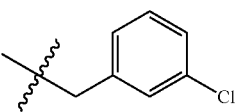 [SMILES: *Cc1cccc(Cl)c1]
I5
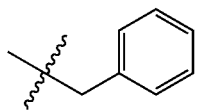 [SMILES: *Cc1ccccc1]
I6
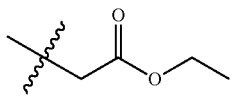 [SMILES: *CC(=O)OCC]
I7
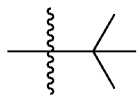 [SMILES: *C(C)(C)C]
I8
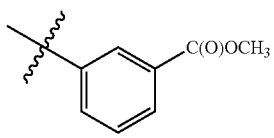
R2
B1
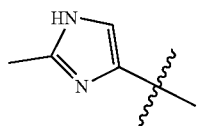 [SMILES: *c1c[nH]c(C)n1]
B2
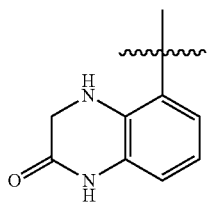 [SMILES: *c1cccc2c1NCC(=O)N2]
B3
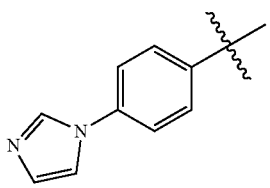 [SMILES: *c1ccc(-n2ccnc2)cc1]
B4
B5
B6

TABLE 2b-continued

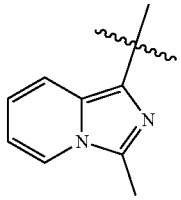 [SMILES: *c1nc(C)n2ccccc12]

|   | 1 | 2 | 3 | 4 | 5 | 6 |
|---|---|---|---|---|---|---|
| A | A1 + B1 + I1 | A1 + B2 + I1 | A1 + B3 + I1 | A1 + B4 + I1 | A1 + B5 + I1 | A1 + B6 + I1 |
| B | A1 + B1 + I2 | A1 + B2 + I2 | A1 + B3 + I2 | A1 + B4 + I2 | A1 + B5 + I2 | A1 + B6 + I2 |
| C | A1 + B1 + I3 | A1 + B2 + I3 | A1 + B3 + I3 | A1 + B4 + I3 | A1 + B5 + I3 | A1 + B6 + I3 |
| D | A1 + B1 + I4 | A1 + B2 + I4 | A1 + B3 + I4 | A1 + B4 + I4 | A1 + B5 + I4 | A1 + B6 + I4 |
| E | A1 + B1 + I5 | A1 + B2 + I5 | A1 + B3 + I5 | A1 + B4 + I5 | A1 + B5 + I5 | A1 + B6 + I5 |
| F | A1 + B1 + I6 | A1 + B2 + I6 | A1 + B3 + I6 | A1 + B4 + I6 | A1 + B5 + I6 | A1 + B6 + I6 |
| G | A1 + B1 + I7 | A1 + B2 + I7 | A1 + B3 + I7 | A1 + B4 + I7 | A1 + B5 + I7 | A1 + B6 + I7 |
| H | A1 + B1 + I8 | A1 + B2 + I8 | A1 + B3 + I8 | A1 + B4 + I8 | A1 + B5 + I8 | A1 + B6 + I8 |

|   | 7 | 8 | 9 | 10 | 11 | 12 |
|---|---|---|---|---|---|---|
| A | A2 + B1 + I1 | A2 + B2 + I1 | A2 + B3 + I1 | A2 + B4 + I1 | A2 + B5 + I1 | A2 + B6 + I1 |
| B | A2 + B1 + I2 | A2 + B2 + I2 | A2 + B3 + I2 | A2 + B4 + I2 | A2 + B5 + I2 | A2 + B6 + I2 |
| C | A2 + B1 + I3 | A2 + B2 + I3 | A2 + B3 + I3 | A2 + B4 + I3 | A2 + B5 + I3 | A2 + B6 + I3 |
| D | A2 + B1 + I4 | A2 + B2 + I4 | A2 + B3 + I4 | A2 + B4 + I4 | A2 + B5 + I4 | A2 + B6 + I4 |
| E | A2 + B1 + I5 | A2 + B2 + I5 | A2 + B3 + I5 | A2 + B4 + I5 | A2 + B5 + I5 | A2 + B6 + I5 |
| F | A2 + B1 + I6 | A2 + B2 + I6 | A2 + B3 + I6 | A2 + B4 + I6 | A2 + B5 + I6 | A2 + B6 + I6 |
| G | A2 + B1 + I7 | A2 + B2 + I7 | A2 + B3 + I7 | A2 + B4 + I7 | A2 + B5 + I7 | A2 + B6 + I7 |
| H | A2 + B1 + I8 | A2 + B2 + I8 | A2 + B3 + I8 | A2 + B4 + I8 | A2 + B5 + I8 | A2 + B6 + I8 |

TABLE 2c

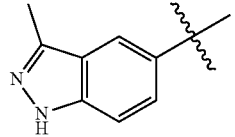 [SMILES: *c1ccc2[nH]nc(C)c2c1]
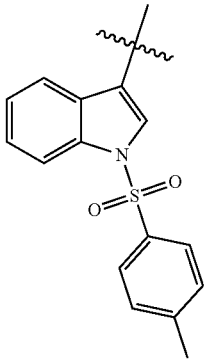 [SMILES: *c1cn(S(=O)(=O)c2ccc(C)cc2)c2ccccc12]

A1     A2     A3

R1

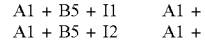

B1     B2

R2

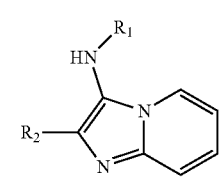
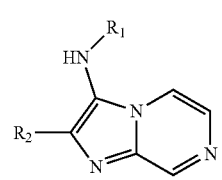
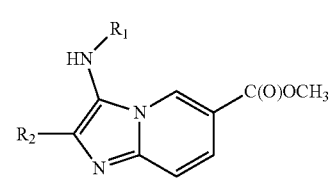
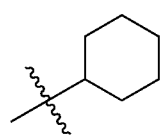 [SMILES: *C1CCCCC1]

C1     C2     C3     C4

TABLE 2c-continued

|  | C5 | C6 | C7 | C8 |
|---|---|---|---|---|
|  | 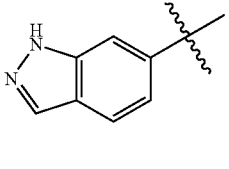 | 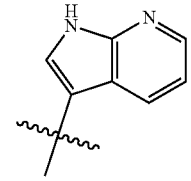 [SMILES: *c1c[nH]c2ncccc12] | 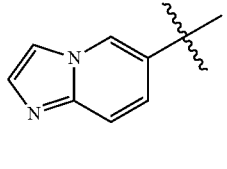 [SMILES: *c1ccc2nccn2c1] | 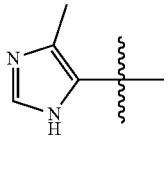 [SMILES: *c1[nH]cnc1C] |

|  | C9 | C10 |
|---|---|---|
|  | 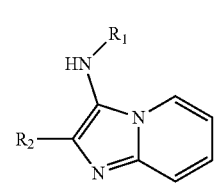 | 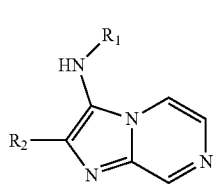 |

|   | 1 | 2 | 3 | 4 | 5 | 6 |
|---|---|---|---|---|---|---|
| A |   |   |   |   |   |   |
| B |   | A1 + B1 + C1 | A1 + B1 + C2 | A1 + B1 + C3 | A1 + B1 + C4 | A1 + B1 + C5 |
| C |   | A1 + B2 + C1 | A1 + B2 + C2 | A1 + B2 + C3 | A1 + B2 + C4 | A1 + B2 + C5 |
| D |   | A2 + B1 + C1 | A2 + B1 + C2 | A2 + B1 + C3 | A2 + B1 + C4 | A2 + B1 + C5 |
| E |   | A2 + B2 + C1 | A2 + B2 + C2 | A2 + B2 + C3 | A2 + B2 + C4 | A2 + B2 + C5 |
| F |   | A3 + B1 + C1 | A3 + B1 + C2 | A3 + B1 + C3 | A3 + B1 + C4 | A3 + B1 + C5 |
| G |   | A3 + B2 + C1 | A3 + B2 + C2 | A3 + B2 + C3 | A3 + B2 + C4 | A3 + B2 + C5 |
| H |   |   |   |   |   |   |

|   | 7 | 8 | 9 | 10 | 11 | 12 |
|---|---|---|---|---|---|---|
| A |   |   |   |   |   |   |
| B | A1 + B1 + C6 | A1 + B1 + C7 | A1 + B1 + C8 | A1 + B1 + C9 | A1 + B1 + C10 |   |
| C | A1 + B2 + C6 | A1 + B2 + C7 | A1 + B2 + C8 | A1 + B2 + C9 | A1 + B2 + C10 |   |
| D | A2 + B1 + C6 | A2 + B1 + C7 | A2 + B1 + C8 | A2 + B1 + C9 | A2 + B1 + C10 |   |
| E | A2 + B2 + C6 | A2 + B2 + C7 | A2 + B2 + C8 | A2 + B2 + C9 | A2 + B2 + C10 |   |
| F | A3 + B1 + C6 | A3 + B1 + C7 | A3 + B1 + C8 | A3 + B1 + C9 | A3 + B1 + C10 |   |
| G | A3 + B2 + C6 | A3 + B2 + C7 | A3 + B2 + C8 | A3 + B2 + C9 | A3 + B2 + C10 |   |
| H |   |   |   |   |   |   |

TABLE 2d

| A1 | A2 | A3 |
|---|---|---|
| 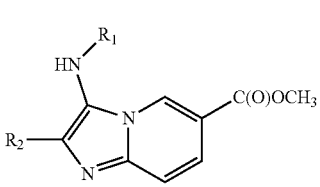 | 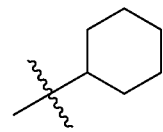 [SMILES: *C1CCCCC1] | 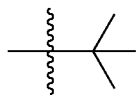 |

R1

| B1 | B2 |
|---|---|
| 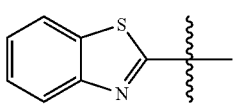 [SMILES: *c1nc2ccccc2s1] | 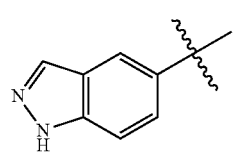 [SMILES: *c1ccc2[nH]ncc2c1] |

R2

| C1 | C2 |
|---|---|

TABLE 2d-continued

C3 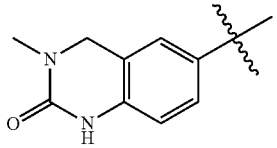 [SMILES: *c1ccc2c(c1)CN(C)C(=O)N2] C4 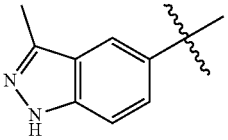 [SMILES: *c1ccc2[nH]nc(C)c2c1]

C5 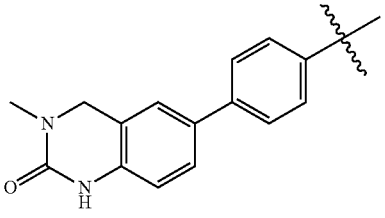 [SMILES: *c1ccc(-c2ccc3c(c2)CN(C)C(=O)N3)cc1] C6 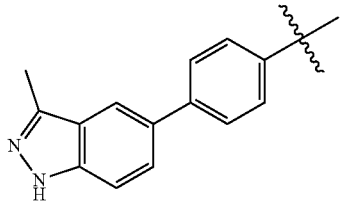 [SMILES: *c1ccc(-c2ccc3[nH]nc(C)c3c2)cc1]

C7 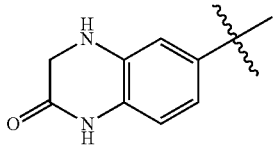 [SMILES: *c1ccc2c(c1)NCC(=O)N2] C8 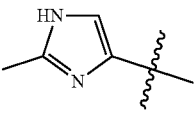 [SMILES: *c1c[nH]c(C)n1]

C9 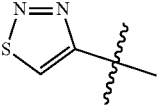 [SMILES: *c1csnn1] C10 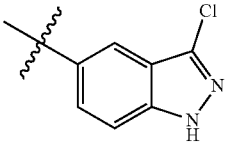 [SMILES: *c1ccc2[nH]nc(Cl)c2c1]

|   | 1 | 2 | 3 | 4 | 5 | 6 |
|---|---|---|---|---|---|---|
| A |   |   |   |   |   |   |
| B |   | A1 + B1 + C1 | A1 + B1 + C2 | A1 + B1 + C3 | A1 + B1 + C4 | A1 + B1 + C5 |
| C |   | A1 + B2 + C1 | A1 + B2 + C2 | A1 + B2 + C3 | A1 + B2 + C4 | A1 + B2 + C5 |
| D |   | A2 + B1 + C1 | A2 + B1 + C2 | A2 + B1 + C3 | A2 + B1 + C4 | A2 + B1 + C5 |
| E |   | A2 + B2 + C1 | A2 + B2 + C2 | A2 + B2 + C3 | A2 + B2 + C4 | A2 + B2 + C5 |
| F |   | A3 + B1 + C1 | A3 + B1 + C2 | A3 + B1 + C3 | A3 + B1 + C4 | A3 + B1 + C5 |
| G |   | A3 + B2 + C1 | A3 + B2 + C2 | A3 + B2 + C3 | A3 + B2 + C4 | A3 + B2 + C5 |
| H |   |   |   |   |   |   |

|   | 7 | 8 | 9 | 10 | 11 | 12 |
|---|---|---|---|---|---|---|
| A |   |   |   |   |   |   |
| B | A1 + B1 + C6 | A1 + B1 + C7 | A1 + B1 + C8 | A1 + B1 + C9 | A1 + B1 + C10 |   |
| C | A1 + B2 + C6 | A1 + B2 + C7 | A1 + B2 + C8 | A1 + B2 + C9 | A1 + B2 + C10 |   |
| D | A2 + B1 + C6 | A2 + B1 + C7 | A2 + B1 + C8 | A2 + B1 + C9 | A2 + B1 + C10 |   |
| E | A2 + B2 + C6 | A2 + B2 + C7 | A2 + B2 + C8 | A2 + B2 + C9 | A2 + B2 + C10 |   |
| F | A3 + B1 + C6 | A3 + B1 + C7 | A3 + B1 + C8 | A3 + B1 + C9 | A3 + B1 + C10 |   |
| G | A3 + B2 + C6 | A3 + B2 + C7 | A3 + B2 + C8 | A3 + B2 + C9 | A3 + B2 + C10 |   |
| H |   |   |   |   |   |   |

TABLE 2e
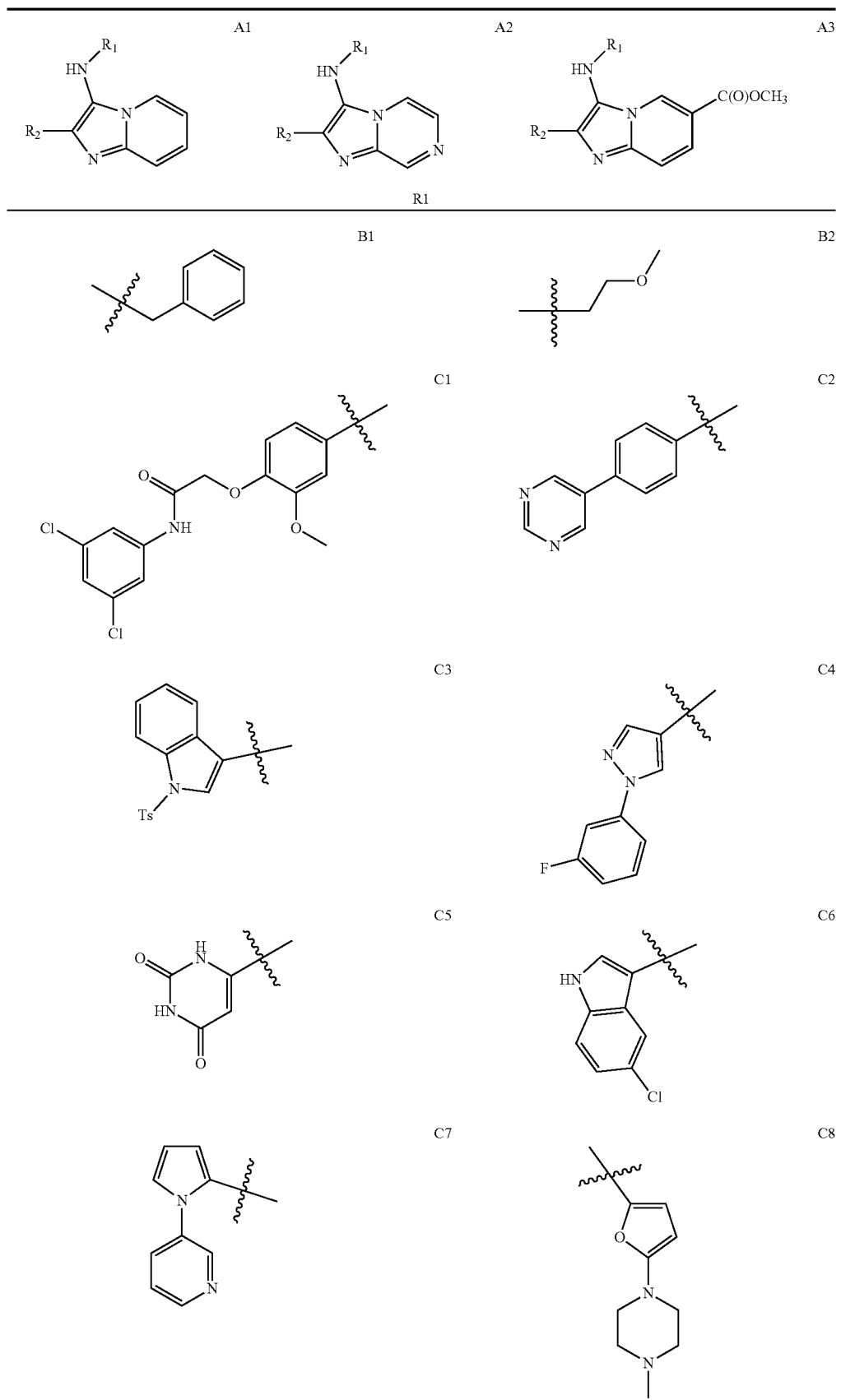

TABLE 2e-continued

| | C9 | | | C10 | |
|---|---|---|---|---|---|
| | 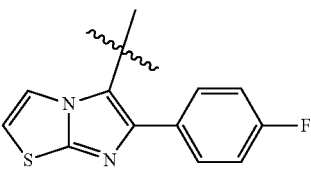 [SMILES: *c1c(-c2ccc(F)cc2)nc2sccn12] | | | 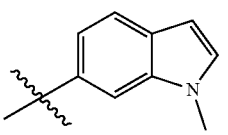 [SMILES: *c1ccc2ccn(C)c2c1] | |
| | 1 | 2 | 3 | 4 | 5 | 6 |
| A | | | | | | |
| B | | A1 + B1 + C1 | A1 + B1 + C2 | A1 + B1 + C3 | A1 + B1 + C4 | A1 + B1 + C5 |
| C | | A1 + B2 + C1 | A1 + B2 + C2 | A1 + B2 + C3 | A1 + B2 + C4 | A1 + B2 + C5 |
| D | | A2 + B1 + C1 | A2 + B1 + C2 | A2 + B1 + C3 | A2 + B1 + C4 | A2 + B1 + C5 |
| E | | A2 + B2 + C1 | A2 + B2 + C2 | A2 + B2 + C3 | A2 + B2 + C4 | A2 + B2 + C5 |
| F | | A3 + B1 + C1 | A3 + B1 + C2 | A3 + B1 + C3 | A3 + B1 + C4 | A3 + B1 + C5 |
| G | | A3 + B2 + C1 | A3 + B2 + C2 | A3 + B2 + C3 | A3 + B2 + C4 | A3 + B2 + C5 |
| H | | | | | | |

| | 7 | 8 | 9 | 10 | 11 | 12 |
|---|---|---|---|---|---|---|
| A | | | | | | |
| B | A1 + B1 + C6 | A1 + B1 + C7 | A1 + B1 + C8 | A1 + B1 + C9 | A1 + B1 + C10 | |
| C | A1 + B2 + C6 | A1 + B2 + C7 | A1 + B2 + C8 | A1 + B2 + C9 | A1 + B2 + C10 | |
| D | A2 + B1 + C6 | A2 + B1 + C7 | A2 + B1 + C8 | A2 + B1 + C9 | A2 + B1 + C10 | |
| E | A2 + B2 + C6 | A2 + B2 + C7 | A2 + B2 + C8 | A2 + B2 + C9 | A2 + B2 + C10 | |
| F | A3 + B1 + C6 | A3 + B1 + C7 | A3 + B1 + C8 | A3 + B1 + C9 | A3 + B1 + C10 | |
| G | A3 + B2 + C6 | A3 + B2 + C7 | A3 + B2 + C8 | A3 + B2 + C9 | A3 + B2 + C10 | |
| H | | | | | | |

The "Warhead" as indicated in FIGS. 11A-11D is a compound of the following structure:

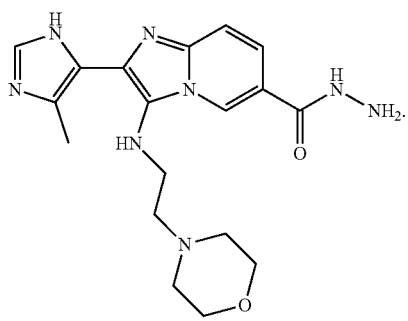 [SMILES: Cc1nc[nH]c1-c1nc2ccc(C(=O)NN)cn2c1NCCN1CCOCC1]

The Warhead compound can react with the aldehyde or ketone groups listed in FIGS. 11A-11D according to the reaction below to form a compound of the present application.

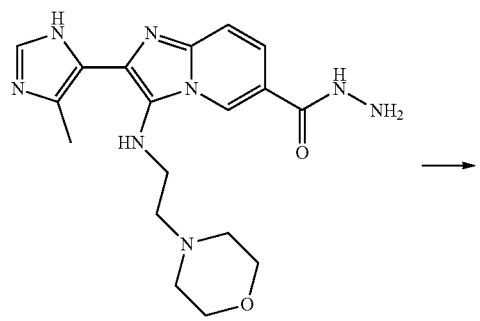

→

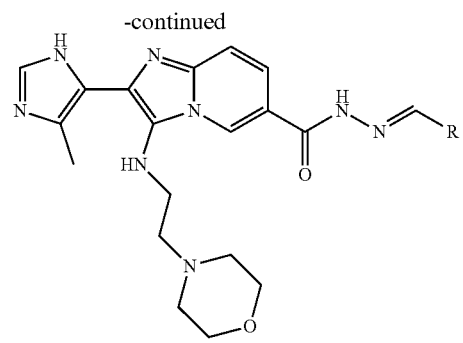

A compound of the present application is capable of modulating the activity of TRIM33. In some embodiments, a compound of the present application is capable of inhibiting the activity of TRIM33. In some embodiments, a compound of the present application is capable of decreasing the activity of TRIM33.

In some embodiments, the inhibition of TRIM33 by a compound of the present application is measured by $IC_{50}$.

In some embodiments, the inhibition of TRIM33 by a compound of the present application is measured by $EC_{50}$.

Potency of the inhibitor can be determined by $EC_{50}$ value. A compound with a lower $EC_{50}$ value, as determined under substantially similar conditions, is a more potent inhibitor relative to a compound with a higher $EC_{50}$ value.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value.

The $IC_{50}$ or $EC_{50}$ of the compound of the present application can be determined by various methods known in the art. For example, the $IC_{50}$ or $EC_{50}$ of the compound of the present application can be measured by an AlphaScreen assay, as described herein (see FIG. 1).

In some embodiments, a compound of the application exhibits greater inhibition of TRIM33 as compared to other homologous proteins. In some embodiments, a compound of the application exhibits greater inhibition of TRIM33 as compared to other Tripartite motif family proteins. In some embodiments, a compound of the application exhibits greater inhibition of TRIM33 as compared to TRIM24. In some embodiments, a compound of the application exhibits 20%, 30%, 50%, 70%, 90%, 100%, 200%, or 500% greater inhibition of TRIM33 as compared to other homologous proteins, such as Tripartite motif family proteins.

In some embodiments, a compound of the application exhibits greater inhibition of TRIM33 as compared to one or more known TRIM33 inhibitors. For example, the compounds can be at least about 2-fold, about 3-fold, about 5-fold, about 10-fold, about 25-fold, about 50-fold or about 100-fold more potent (e.g., as measured by $IC_{50}$).

Definitions

Listed below are definitions of various terms used to describe this application. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkoxy" refers to an —O-alkyl radical.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which at least one ring atom is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the application, any of the heteroaryls and substituted heteroaryls described herein, can be any aromatic group. Aromatic groups can be substituted or unsubstituted.

The term "heterocyclyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocyclyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_6$ alkyl is as previously defined.

The term "dialkylamino" refers to a group having the structure —N($C_1$-$C_{12}$ alkyl)$_2$, e.g., —N($C_1$-$C_6$ alkyl)$_2$, where $C_1$-$C_6$ alkyl is as previously defined.

The terms "hal," "halo," and "halogen," as used herein, refer to an atom selected from fluorine, chlorine, bromine, and iodine.

The term "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl linker (—CH$_2$—), ethyl linker (—CH$_2$CH$_2$— or —CH(CH$_3$)—), propyl linker (—CH$_2$CH$_2$CH$_2$—, —CH(CH$_3$)CH$_2$—, or —C(CH$_3$)$_2$—), butyl linker (—CH$_2$CH$_2$CH$_2$CH$_2$—, —CH(CH$_3$)CH$_2$CH$_2$—, —CH$_2$CH(CH$_3$)CH$_2$—, —C(CH$_3$)$_2$CH$_2$—, or —CH(CH$_3$)CH(CH$_3$)—), pentyl linker (—CH$_2$CH$_2$CH$_2$CH$_2$CH$_2$—, —CH(CH$_3$)CH$_2$CH$_2$CH$_2$—, —CH$_2$CH(CH$_3$)CH$_2$CH$_2$—, —C(CH$_3$)$_2$CH$_2$CH$_2$—, or —CH$_2$C(CH$_3$)$_2$CH$_2$—), and hexyl linker (—CH$_2$CH$_2$CH$_2$CH$_2$CH$_2$CH$_2$—).

As described herein, a compound of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen in a given structure with the radical of a specified substituent. Unless otherwise indicated, an optionally substituted group may have a substituent at each substitutable position of the group, and when more than one position in any given structure may be substituted with more than one substituent selected from a specified group, and the substituent may be either the same or different at every position.

It is understood that the aryls, heteroaryls, alkyls, and the like can be substituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C3-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{10}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating", and "treatment" refer to a method of alleviating or abating a disease and/or its attendant symptoms.

As used herein, "preventing" or "prevent" describes reducing or eliminating the onset of the symptoms or complications of the disease, condition, or disorder.

As used herein the term "GS-A" refers to a compound having the chemical structure:

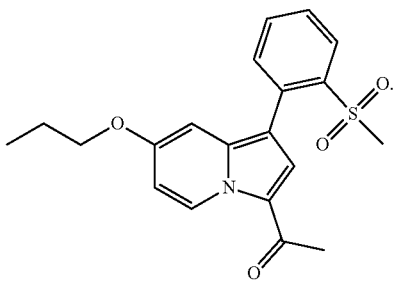 [SMILES: CCCOc1ccn2c(C(C)=O)cc(-c3ccccc3S(C)(=O)=O)c2c1]

As used herein the term "IACS9571" refers to a compound having the chemical structure:

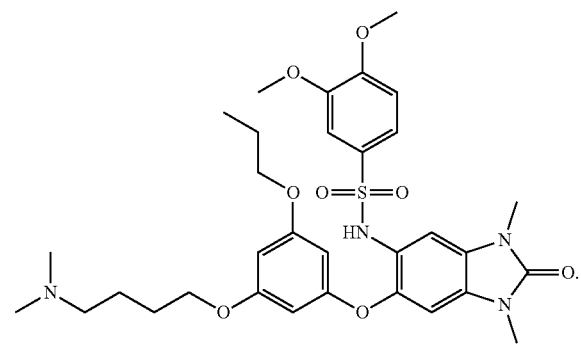 [SMILES: CCCOc1cc(OCCCCN(C)C)cc(Oc2cc3c(cc2NS(=O)(=O)c2ccc(OC)c(OC)c2)n(C)c(=O)n3C)c1]

As used herein the term "UMB148" or "ACV-2-257" refers to a compound having the chemical structure:

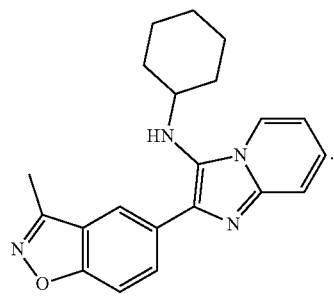 [SMILES: Cc1noc2ccc(-c3nc4ccccn4c3NC3CCCCC3)cc12]

As used herein the term "UMB34" or "ACV-2-258" refers to a compound having the chemical structure:

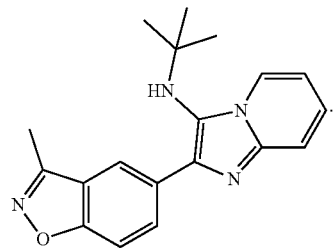 [SMILES: Cc1noc2ccc(-c3nc4ccccn4c3NC(C)(C)C)cc12]

As used herein the term "UMB148 warhead" refers to a compound having the chemical structure:

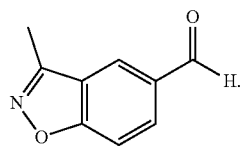

The terms "disease(s)", "disorder(s)", and "condition(s)" are used interchangeably, unless the context clearly dictates otherwise.

The term "therapeutically effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews*, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a compound of the application, or an enantiomer, diastereomer, stereoisomer, or pharmaceutically acceptable salt thereof, and a pharmaceutically acceptable carrier.

In another aspect, the application provides a kit comprising a compound capable of inhibiting protein kinase activity of at least one protein kinase selected from one or more compounds disclosed herein, or a pharmaceutically acceptable salt, hydrate, solvate, prodrug, stereoisomer, or tautomer thereof, optionally in combination with a second agent and instructions for use in treating cancer. In one embodiment, the compound in the kit inhibits more than one protein kinase In another aspect, the application provides a method of synthesizing a compound disclosed herein.

The synthesis of the compounds of the application can be found herein and in the Examples below.

Other embodiments are a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^{3}H$, $^{2}H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base.

Alternatively, the salt forms of the compounds of the application can be prepared using salts of the starting materials or intermediates.

The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkyl-carbanochloridate, para-nitrophenyl carbonate, or the like).

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_{14}$) occurs more than one time in any constituent or formula for a compound, its definition at each occurrence is independent of its definition at every other occurrence. Thus, for example, if a group is shown to be substituted with one or more $R_{14}$ moieties, then $R_{14}$ at each occurrence is selected independently from the definition of $R_{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew.*

*Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of Synthesizing the Compounds

A compound of the present application may be made by a variety of methods, including standard chemistry. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof. Suitable synthetic routes are depicted in the schemes below.

A compound of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of a compound of the present application.

A compound disclosed herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of a compound disclosed herein.

Those skilled in the art will recognize if a stereocenter exists in a compound disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

A compound of the present application can be prepared in a number of ways well known to those skilled in the art of organic synthesis. By way of example, a compound of the present application can be synthesized using the methods described below, together with synthetic methods known in the art of synthetic organic chemistry, or variations thereon as appreciated by those skilled in the art. Preferred methods include but are not limited to those methods described below. A compound of the present application can be synthesized by following the steps outlined in General Scheme A. Starting materials are either commercially available or made by known procedures in the reported literature or as illustrated.

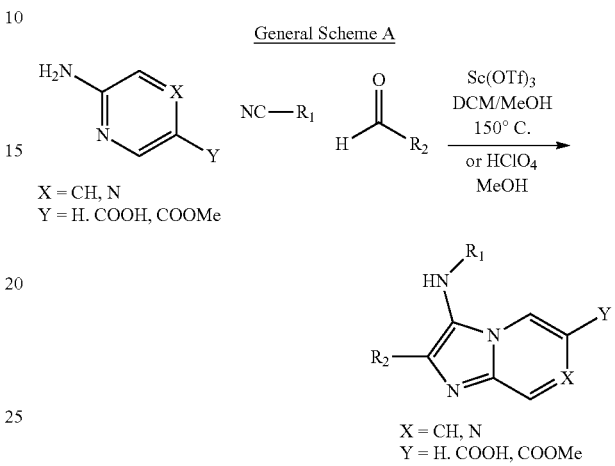

General Scheme A

The general way of preparing a compound of Formula I is exemplified in General Scheme A. A compound of Formula I may be prepared through Groebke-Blackburn-Bienayme Multicomponent Reaction.

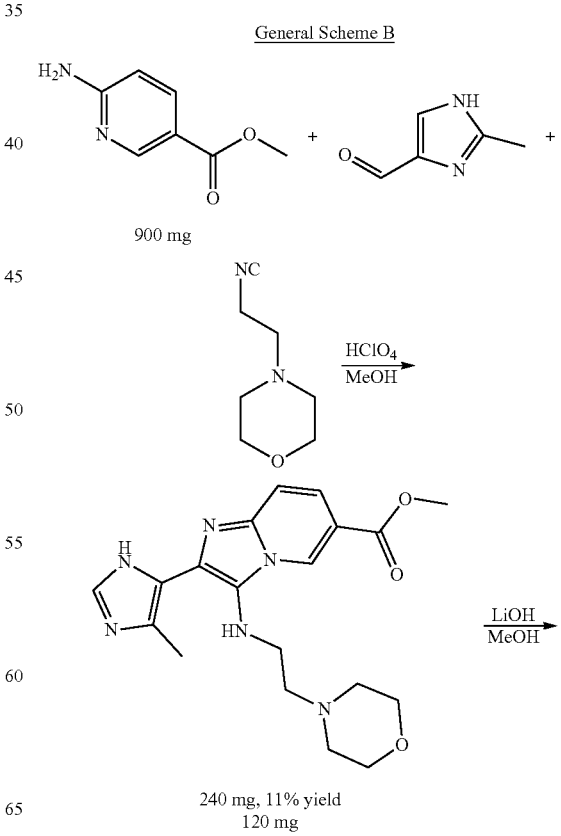

General Scheme B

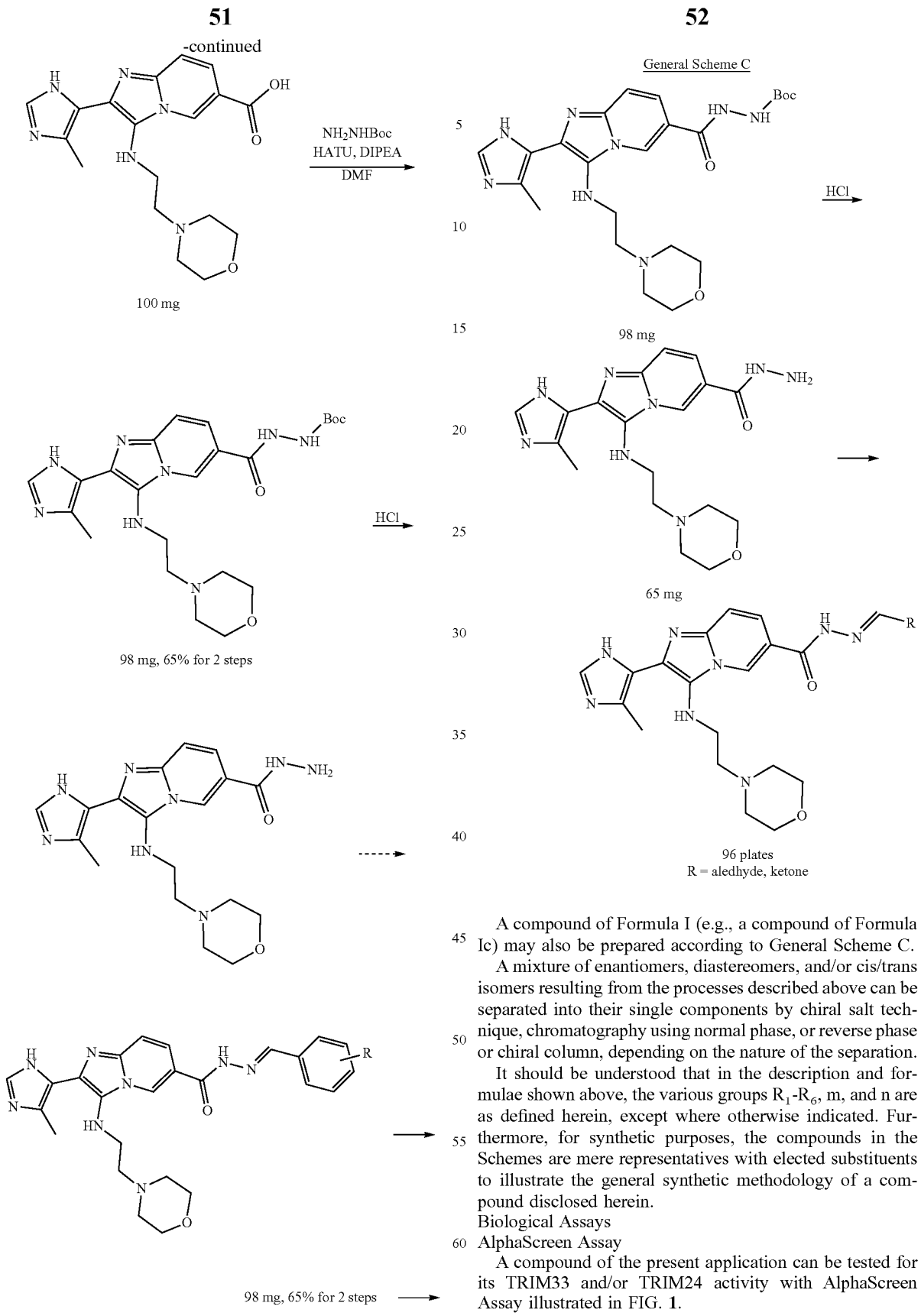

A compound of Formula I (e.g., a compound of Formula Ic) may also be prepared according to General Scheme B.

A compound of Formula I (e.g., a compound of Formula Ic) may also be prepared according to General Scheme C.

A mixture of enantiomers, diastereomers, and/or cis/trans isomers resulting from the processes described above can be separated into their single components by chiral salt technique, chromatography using normal phase, or reverse phase or chiral column, depending on the nature of the separation.

It should be understood that in the description and formulae shown above, the various groups $R_1$-$R_6$, m, and n are as defined herein, except where otherwise indicated. Furthermore, for synthetic purposes, the compounds in the Schemes are mere representatives with elected substituents to illustrate the general synthetic methodology of a compound disclosed herein.

Biological Assays

AlphaScreen Assay

A compound of the present application can be tested for its TRIM33 and/or TRIM24 activity with AlphaScreen Assay illustrated in FIG. 1.

Methods of the Application

Another aspect of the present application relates to a method of inhibiting TRIM33, comprising administering to a subject in need thereof an effective amount of a compound of the present application (e.g., a compound of Formula I), or a pharmaceutically acceptable salt or ester thereof.

Another aspect of the present application relates to a method of treating or preventing a disease or disorder (e.g., cancer) in which TRIM33 plays a role, comprising administering to a subject in need thereof an effective amount of a compound of the present application (e.g., a compound of Formula I), or a pharmaceutically acceptable salt or ester thereof.

In certain embodiments, the disease is cancer or a proliferative disease.

In further embodiments, the cancer is a cancer of B cell origin. In further embodiments, the cancer is a lineage dependent cancer. In further embodiments, the cancer is a lineage dependent cancer where TRIM33 plays a role in the initiation and/or development of the cancer.

Another aspect of the application provides a method of treating or preventing a cancer of B cell origin in a subject, wherein the subject is identified as being in need of TRIM33 inhibition for the treatment of cancer, comprising administering to the subject an effective amount of a compound of the present application (e.g., a compound of Formula I), or a pharmaceutically acceptable salt or ester thereof.

In certain embodiments, the application provides a method of treating any of the disorders described herein, wherein the subject is a human. In certain embodiments, the application provides a method of preventing any of the disorders described herein, wherein the subject is a human.

Another aspect of the present application relates to a compound of the present application (e.g., a compound of Formula I), or a pharmaceutically acceptable salt or ester thereof, for inhibiting TRIM33, or treating or preventing a disease or disorder (e.g., cancer) in which TRIM33 plays a role, a cancer of B cell origin, or a lineage dependent disease or disorder in which TRIM33 plays a role.

Another aspect of the present application relates to a compound of the present application (e.g., a compound of Formula I), or a pharmaceutically acceptable salt or ester thereof, for use in the manufacture of a medicament in the inhibition of TRIM33, or the treatment or prevention of a disease or disorder (e.g., cancer) in which TRIM33 plays a role, a cancer of B cell origin, or a lineage dependent disease or disorder in which TRIM33 plays a role.

Another aspect of the present application relates to use of a compound of the present application (e.g., a compound of Formula I), or a pharmaceutically acceptable salt or ester thereof, in inhibiting TRIM33, or treating or preventing a disease or disorder (e.g., cancer) in which TRIM33 plays a role, a cancer of B cell origin, or a lineage dependent disease or disorder in which TRIM33 plays a role.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more a compound of the application in the manufacture of a medicament for the treatment of cancer, including without limitation the various types of cancer disclosed herein.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Pharmaceutical Compositions

In another aspect, the application provides a pharmaceutical composition comprising a compound disclosed herein, or a pharmaceutically acceptable ester, salt, or prodrug thereof, together with a pharmaceutically acceptable carrier.

A compound of the application can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present application in free form or in a pharmaceutically acceptable salt form in association. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing a compound of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present application, disorders are treated or prevented in a subject, such as a human or other animal, by administering to the subject a therapeutically effective amount of a compound of the application, in such amounts and for such time as is necessary to achieve the desired result. The term "therapeutically effective amount" of a compound of the application, as used herein, means a sufficient amount of the compound so as to decrease the symptoms of a disorder in a subject. As is well understood in the medical arts a therapeutically effective amount of a compound of this application will be at a reasonable benefit/risk ratio applicable to any medical treatment.

In general, a compound of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g., a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present application.

In another aspect, the application provides a kit comprising a compound capable of inhibiting kinase activity selected from one or more compounds of disclosed herein, or a pharmaceutically acceptable salt, hydrate, solvate, prodrug, stereoisomer, or tautomer thereof, and instructions for use in treating cancer.

In another aspect, the application provides a kit comprising a compound capable of inhibiting TRIM33 activity selected from a compound disclosed herein, or a pharmaceutically acceptable salt, hydrate, solvate, prodrug, stereoisomer, or tautomer thereof.

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

EXAMPLES

Example 1: Synthesis of methyl 2-(4-methyl-1H-imidazol-5-yl)-3-((2-morpholinoethyl)amino)imidazo[1,2-a]pyridine-6-carboxylate (Compound 24)

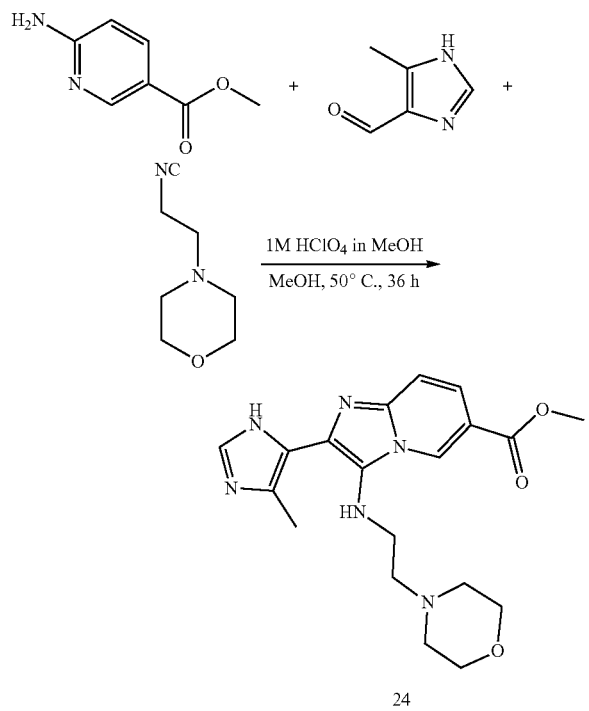

To a solution of methyl 6-aminonicotinate (0.9 g, 6.0 mmol) in MeOH (15 ml) were added 5-methyl-1H-imidazole-4-carbaldehyde (1.0 g, 9.0 mmol) and 4-(2-isocyanoethyl)morpholine (1.26 g, 9.0 mmol). 1M HClO$_4$ in MeOH (0.6 ml) was added dropwise and the mixture was heated at 50° C. for 36 hrs. The reaction was cooled down and diluted with dichloromethane (100 ml) and extracted successively with water (50 mL), a saturated solution of NaHCO$_3$ (25 ml), and brine (50 ml). The organic phase was dried over NaSO$_4$, concentrated under reduced pressure, and then the residue was purified by ISCO (DCM/MeOH=90/10) to afford the pure product as yellow solid (240 mg, 10%).

Example 2: Synthesis of 2-(4-methyl-1H-imidazol-5-yl)-3-((2-morpholinoethyl)amino)imidazo[1,2-a]pyridine-6-carboxylic acid (Compound 25)

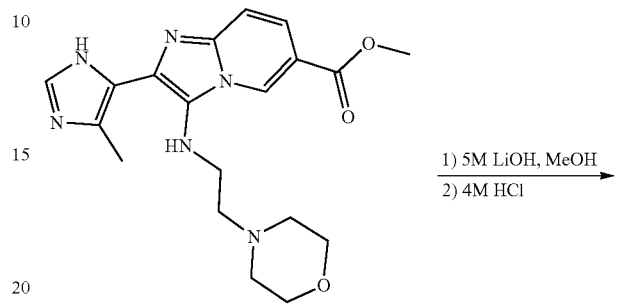

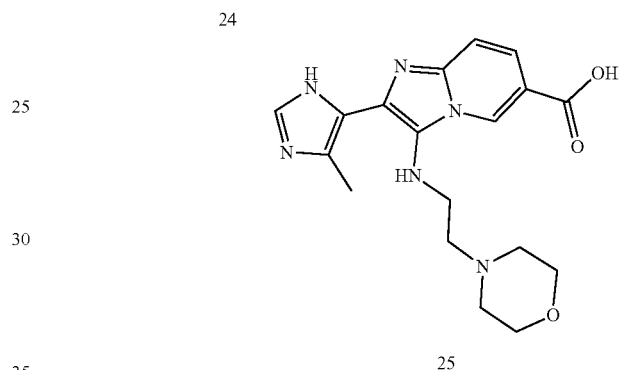

To a solution of methyl 2(4-methyl-1H-imidazol-5-yl)-34 (2-morpholinoethyl)amino) imidazo[1,2-a]pyridine-6-carboxylate (120 mg) in MeOH (15 ml) was added 5 M LiOH in water (0.2 ml) dropwise and the mixture was kept stirring for 24 hr. When the reaction was completed as monitored by LCMS, 4N HCl (0.3 ml) was added into the solution to PH~6. The reaction mixture was concentrated under reduced pressure to remove MeOH to afford dark oil crude product (100 mg).

Example 3: Synthesis of tert-butyl 2-(2-(4-methyl-1H-imidazol-5-yl)-3-((2-morpholinoethyl)amino)imidazo[1,2-a]pyridine-6-carbonyl)hydrazine-1-carboxylate (Compound 26)

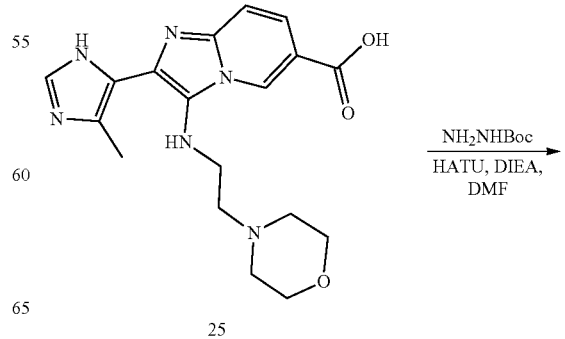

-continued

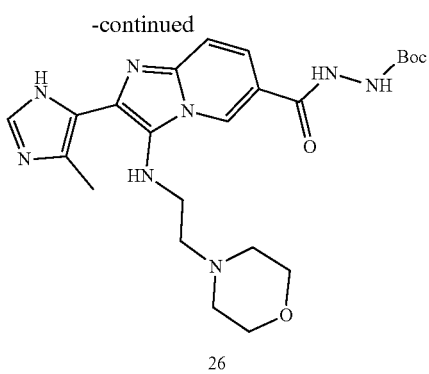

26

To a solution of 2(4-methyl-1H-imidazol-5-yl)-3-(2-morpholinoethyl)amino) imidazo[1,2-a]pyridine-6-carboxylic acid (100 mg, 0.3 mmol) and HATU (235 mg, 0.6 mmol) in DMF (0.5 ml) was added DIPEA (387 mg, 3 mmol) dropwise. Tert-butyl hydrazinecarboxylate (82 mg, 0.62 mmol) was added and the reaction was kept stirring for 24 hr. When the reaction was completed as monitored by LCMS, the reaction was diluted with dichloromethane (100 ml) and extracted successively with water(50 mL), a saturated solution of NaHCO$_3$ (25 ml), and brine (50 ml). The organic phase was dried over NaSO$_4$, concentrated under reduced pressure, and then the residue was purified by ISCO (DCM/MeOH=90/10) to afford the pure product as yellow solid (98 mg).

Example 4: Synthesis of 2-(4-methyl-1H-imidazol-5-yl)-3-((2-morpholinoethyl)amino)imidazo[1,2-a]pyridine-6-carbohydrazide (Compound 27)

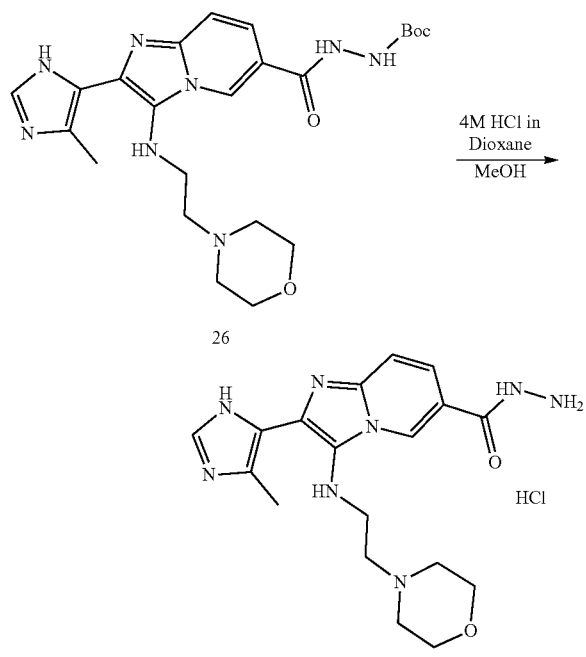

To a solution of tert-butyl 2-(2-(4-methyl-1H-imidazol-5-yl)-3-(2-morpholinoethyl)amino)imidazo[1,2-a]pyridine-6-carbonyl)hydrazine-1-carboxylate (98 mg) in MeOH (7 ml) was added 4 M HCl in Dioxane (0.3 ml) dropwise and the mixture was kept stirring for 24 hr. When the reaction was completed as monitored by LCMS, the reaction was concentrated under reduced pressure to remove MeOH to afford yellow solid crude product (80 mg).

Example 5: Synthesis of 2-(4-methyl-1H-imidazol-5-yl)-N-(2-morpholinoethyl)imidazo[1,2-a]pyridin-3-amine (Compound 5)

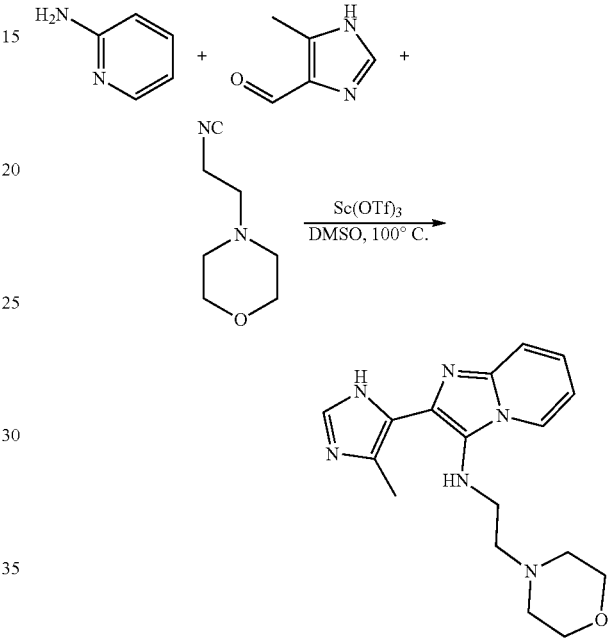

5

To a solution of pyridin-2-amine (23.5 mg, 0.25 mmol) in DMSO (0.7 ml) were added 5-methyl-1H-imidazole-4-carbaldehyde (41.3 mg, 0.37 mmol) and 4-(2-isocyanoethyl)morpholine (40.3 g, 0.29 mmol). Sc(OTf)$_3$ (12 mg, 0.02 mmol) was added and the mixture was heated at 100° C. for 12 hrs. The reaction was cooled down and diluted with dichloromethane (20 ml) and extracted successively with water (10 mL), a saturated solution of NaHCO$_3$ (5 ml), and brine (20 ml). The organic phase was dried over NaSO$_4$, concentrated under reduced pressure, and then the residue was purified by ISCO (DCM/MeOH=90/10) to afford the pure product as yellow solid (12 mg).

Example 6: Synthesis of N-(4-methoxyphenyl)-2-(4-methyl-1H-imidazol-5-yl)imidazo[1,2-a]pyridin-3-amine (Compound 28)

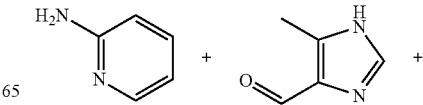

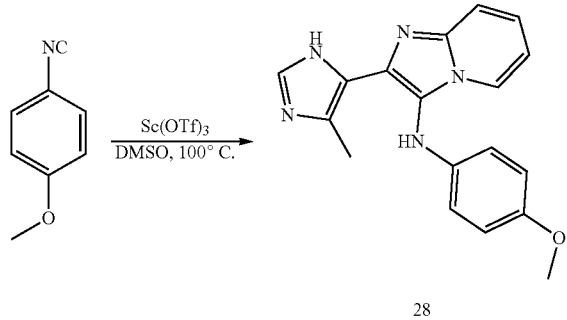

To a solution of pyridin-2-amine (23.5 mg, 0.25 mmol) in DMSO (0.7 ml) were added 5-methyl-1H-imidazole-4-carbaldehyde (41.3 mg, 0.37 mmol) and 1-isocyano-4-methoxybenzene (38.3 mg, 0.29 mmol). Sc(OTf)$_3$ (12 mg, 0.02 mol) was added and the mixture was heated at 100° C. for 12 hrs. The reaction was cooled down and diluted with dichloromethane (20 ml) and extracted successively with water(10 mL), a saturated solution of NaHCO$_3$ (5 ml), and brine (20 ml). The organic phase was dried over NaSO$_4$, concentrated under reduced pressure, and then the residue was purified by ISCO (PE/EA=10/90) to afford the pure product as yellow solid (10 mg).

Example 7: Synthesis of 6-bromo-N-(4-methoxyphenyl)-2-(2-methyl-1H-imidazol-5-yl)imidazo[1,2-a]pyridin-3-amine (Compound 18)

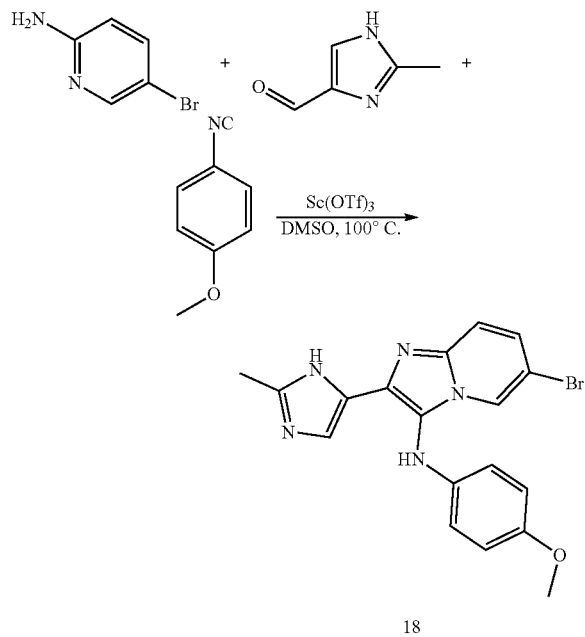

To a solution of 5-bromopyridin-2-amine (43.2 mg, 0.25 mmol) in DMSO (0.7 ml) were added 2-methyl-1H-imidazole-4-carbaldehyde (41.3 mg, 0.37 mmol) and 1-isocyano-4-methoxybenzene (38.3 mg, 0.29 mmol). Sc(OTf)$_3$ (12 mg, 0.02 mol) was added and the mixture was heated at 100° C. for 12 hrs. The reaction was cooled down and diluted with dichloromethane (20 ml) and extracted successively with water (10 mL), a saturated solution of NaHCO$_3$ (5 ml), and brine (20 ml). The organic phase was dried over NaSO$_4$, concentrated under reduced pressure, and then the residue was purified by ISCO (PE/EA=10/90) to afford the pure product as yellow solid (6 mg).

Example 8: Assay for Assessing the Activity of the Compounds of the Present Application An in vitro AlphaScreen® binding assay was developed to detect an interaction between a recombinant PHD-bromodomain module of TRIM33 (50 nm) with a synthetic, biotinylated H3 peptide (20 residues) (H3K9me3K18ac) (100 nm) in 384-well plate format (see FIG. 1). Additionally, a second AlphaScreen® binding assay for TRIM24 as counter-screening assay for selectivity of TRIM33 over TRIM24 was developed. A focused compound libraries for TRIM33 inhibitor development was designed and synthesized using the design principle that is to connect the bromodomain binding motif/fragment to proper chemical scaffold via multi-component reactions, such as Groebke-Blackburn-Bienaymé (GBB) coupling reaction, to establish chemically bias library.

With multiple libraries synthesized (~400 compounds) as described above, compounds were screened against TRIM33 and TRIM24 by AlphaScreen to establish structure activity relationship (SAR). Three bromodomain binding motifs displayed selectivity for TRIM33 over TRIM24 in each library, and were chosen to create a third TRIM33-selective library through multicomponent reactions (90 compounds).

The TRIM33-selective compounds were characterized by biophysical measurement and crystallography to establish binding mode. These compounds are tested in cell culture models to define the spectrum of B-cell neoplasms that are dependent on the chromatin reader functionality of TRIM33, using human cancer cell lines and primary patient-derived samples. Small-molecule inhibitors of the PHD-Bromodomain functionality of TRIM33 is investigated for development as novel therapeutics.

TRIM33 and/or TRIM24 modulating activities of representative compounds of the present application are shown in FIGS. 2A, 2B, 3A, 3B, 4A, 4B, 5, 6, 7, 8, 9A, 9B, and 10A-10P, 12A-12D, 13B, 13C, 14B, 14C, 15A-15L, and 16B, 16C, and the tables below.

TABLE 3

TRIM33 modulating activity of the compounds shown in Table 2a

|   | 1 | 2 | 3 | 4 | 5 | 6 | 7 | 8 | 9 | 10 | 11 | 12 |
|---|---|---|---|---|---|---|---|---|---|----|----|----|
| A | 5.901 | 1.356 | 17.22 | 27.77 | 26.78 | 0.00319 | ~415.4 | 269.1 | 285.8 | 130.9 | 207.3 | 153.4 |
| B | 1.069 | 1.365 | 16.3 | 3.576 | 16.41 | 1.165 | 116.2 | 44.21 | 203.6 | 70.95 | 120.7 | 14.69 |
| C | 13.79 | 24.87 | 139.1 | 365.9 | 87.39 | 26.04 | 168.9 | 29.69 | 190.5 | 259.2 | 46.11 | 38.31 |
| D | 8.718 | 21.74 | 47.5 | 69.57 | 46.31 | 9.597 | 80.02 | 23.67 | 137.8 | 151.3 | 65.97 | 38.47 |
| E | 18.94 | 7.172 | 56.94 | 71.36 | 649.8 | 8.574 | 3.597 | 3.457 | 7.884 | 449.6 | 11.34 | NC |

TABLE 3-continued

TRIM33 modulating activity of the compounds shown in Table 2a

|   | 1 | 2 | 3 | 4 | 5 | 6 | 7 | 8 | 9 | 10 | 11 | 12 |
|---|---|---|---|---|---|---|---|---|---|---|---|---|
| F | 18.13 | 12.63 | 44.01 | 79.2 | 112.8 | 19.35 | 1.026 | NC | 37.01 | 26.18 | 10.07 | 0.01372 |
| G | 42.55 | 15.73 | 357.2 | 302.6 | 125.2 | 22.21 | 121.2 | 20.43 | 155.9 | 214.1 | 48.13 | 70.29 |
| H | 32.61 | 12.2 | 77.02 | 95.59 | 65.08 | 48.59 | BLANK | BLANK | BLANK | BLANK | BLANK | BLANK |
| IACS9571 | 10.57 | | | | | | | | | | | |
| GS-A | 50.87 | | | | | | | | | | | |

TABLE 4

TRIM24 modulating activity of the compounds shown in Table 2a

|   | 1 | 2 | 3 | 4 | 5 | 6 | 7 | 8 | 9 | 10 | 11 | 12 |
|---|---|---|---|---|---|---|---|---|---|---|---|---|
| A | 96.51 | 44.44 | 140.6 | 242.4 | 266.9 | 1.714 | 186.4 | | 91830 | 1893 | 54.84 | ~384.9 |
| B | 9.028 | 31.66 | 35.4 | 47.71 | 42.78 | 6.23 | 90.13 | 56430 | 23460 | 118.7 | 98.42 | 7.322 |
| C | 249 | 1515 | 5797 | 17720 | 2077 | 153.1 | 320.1 | | 5454 | 2191 | 817.9 | 88.26 |
| D | 141.6 | 371.6 | 444.7 | 250.2 | | 159.4 | | 835.4 | 2847 | 4984 | 819.4 | 226 |
| E | 179.6 | 622.4 | | 2874 | | 111.1 | 13.01 | 63.53 | 243.1 | 193.8 | 81.73 | 4.604 |
| F | 143 | 376.9 | 511 | 935.1 | 319.4 | 77.25 | 8.485 | 28.88 | 133.9 | 117.2 | 29.26 | 2.594 |
| G | ~502.2 | 5981 | 28080 | ~700.5 | 60830 | 375.2 | 100 | 283.5 | 706 | 1376 | 296.4 | 223.9 |
| H | 254.9 | 5651 | 2883 | 1039 | 33520 | 354.7 | BLANK | BLANK | BLANK | BLANK | BLANK | BLANK |
| IACS9571 | interupted | | | | | | | | | | | |
| GS-A | 45.31 | | | | | | | | | | | |

TABLE 5

Ratio of TRIM24 IC50 over TRIM33 IC50 of the compounds shown in Table 2a

|   | 1 | 2 | 3 | 4 | 5 | 6 | 7 | 8 | 9 | 10 | 11 | 12 |
|---|---|---|---|---|---|---|---|---|---|---|---|---|
| A | 16.35 | 32.77 | 8.16 | 8.73 | 9.97 | 537.64 | | | 321.31 | 14.46 | 0.26 | |
| B | 8.45 | 23.19 | 2.17 | 13.34 | 2.61 | 5.35 | 0.78 | 1276.41 | 115.23 | 1.67 | 0.82 | 0.50 |
| C | 18.06 | 60.92 | 41.68 | 48.43 | 23.77 | 5.88 | 1.90 | | 28.63 | 8.45 | 17.74 | 2.30 |
| D | 16.24 | 17.09 | 9.36 | 3.60 | | 16.61 | | 35.29 | 20.66 | 32.94 | 12.42 | 5.87 |
| E | 9.48 | 86.78 | | 40.27 | | 12.96 | 3.62 | 18.38 | 30.83 | 0.43 | 7.21 | |
| F | 7.89 | 29.84 | 11.61 | 11.81 | 2.83 | 3.99 | 8.27 | | 3.62 | 4.48 | 2.91 | 189.07 |
| G | | 380.23 | 78.61 | | 485.86 | 16.89 | 0.83 | 13.88 | 4.53 | 6.43 | 6.16 | 3.19 |
| H | 7.82 | 463.20 | 37.43 | 10.87 | 515.06 | 7.30 | BLANK | BLANK | BLANK | BLANK | BLANK | BLANK |

TABLE 6

Figure 11A:
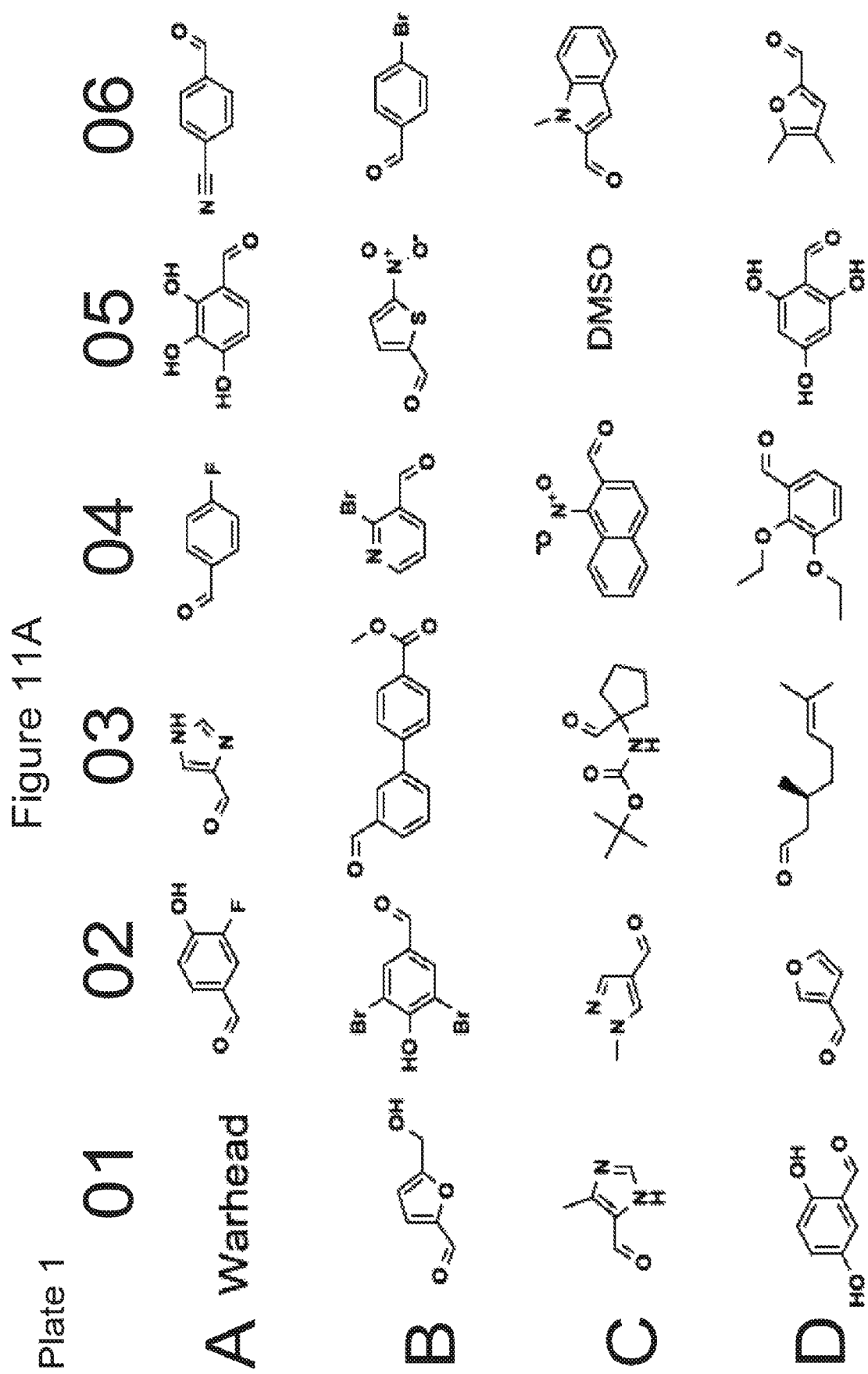
FIGS. 11A-11D list various groups which correspond to $R_7/R_7'$ in the formulae described in the present application.
Figure 11A:
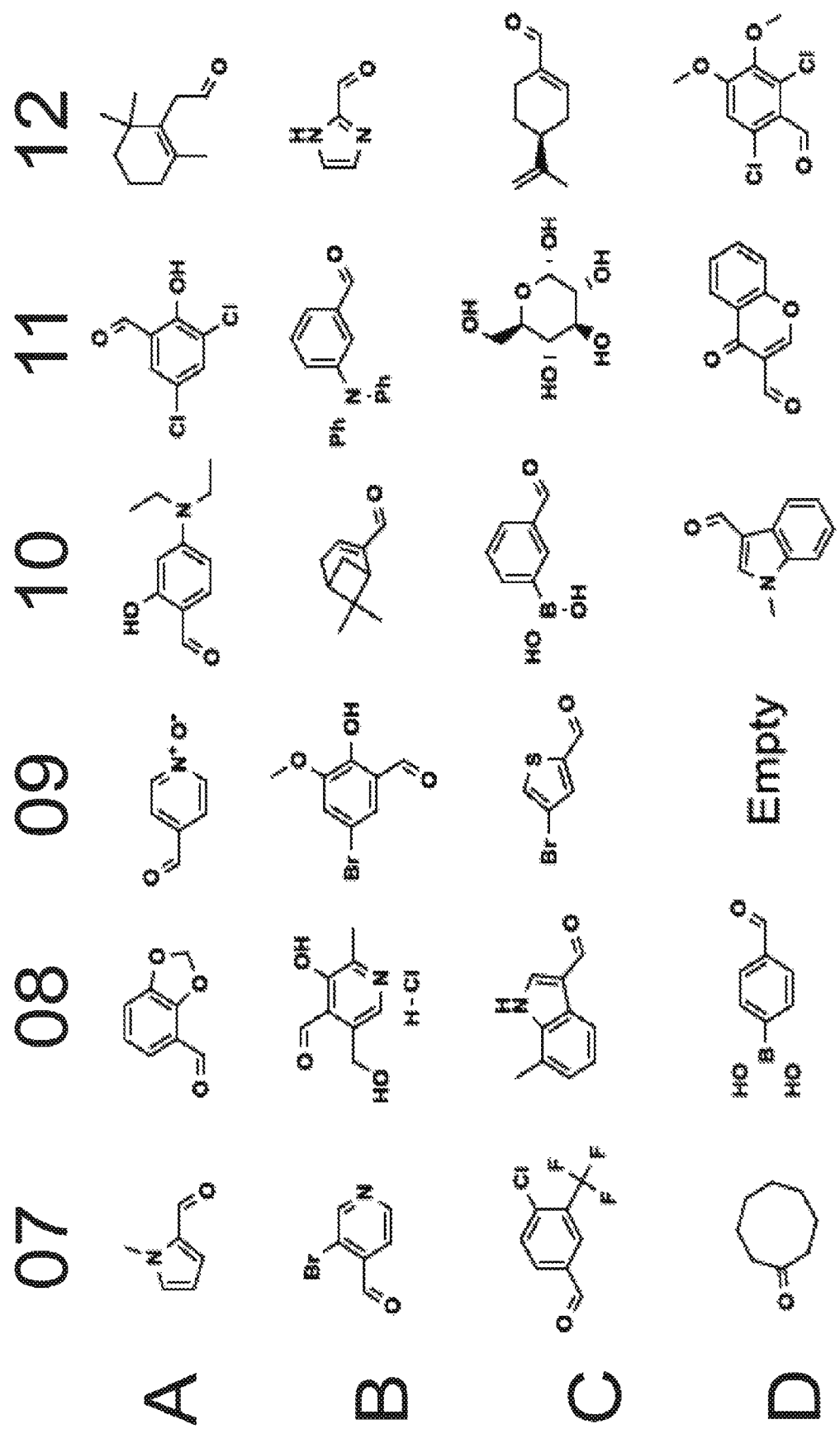
Figure 11A:
Figure 11A:
Figure 11A:
Figure 11A:
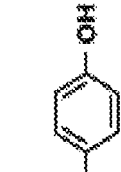
Figure 11A:
Figure 11A:
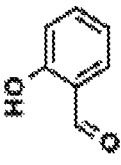
Figure 11A:
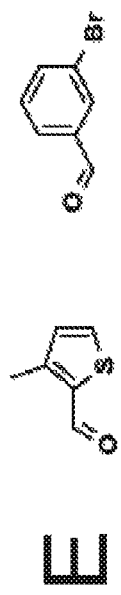
Figure 11A:
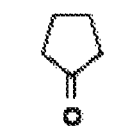
Figure 11A:
Figure 11A:
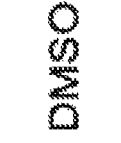
Figure 11A:
Figure 11A:
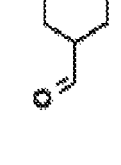
Figure 11A:
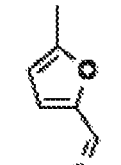
Figure 11A:
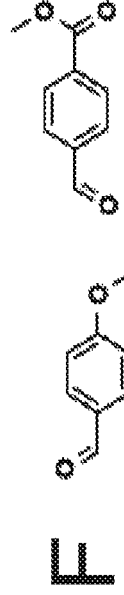
Figure 11A:
Figure 11A:
Figure 11A:
Figure 11A:
Figure 11A:
Figure 11A:
Figure 11A:
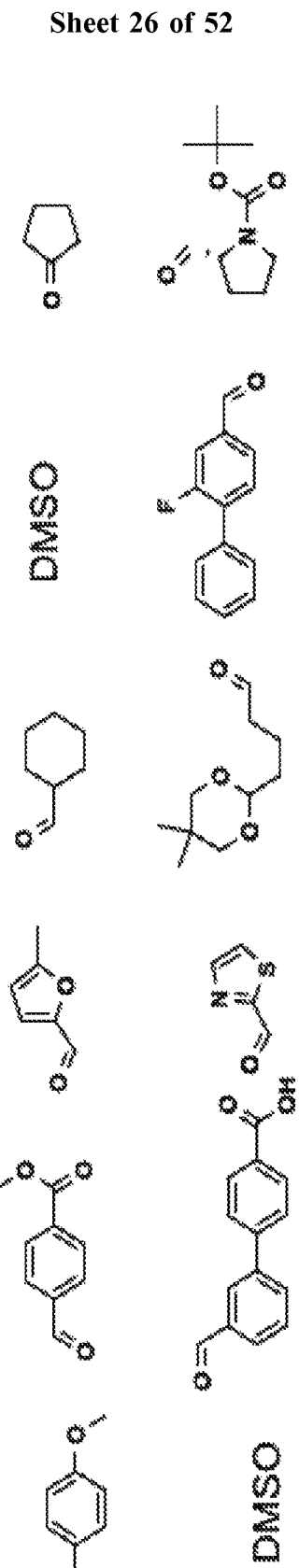
Figure 11A:
Figure 11A:
Figure 11A:
Figure 11A:
Figure 11A:
Figure 11A:
Figure 11A:
Figure 11A:
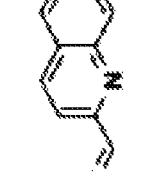
Figure 11A:
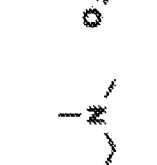
Figure 11A:
Figure 11A:
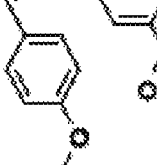
Figure 11A:
Figure 11A:
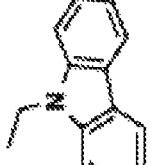
Figure 11A:
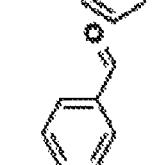
Figure 11A:
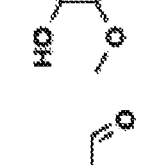
Figure 11A:
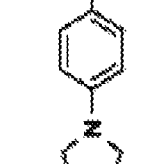
Figure 11A:
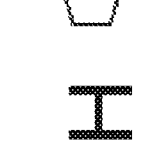
Figure 11B:
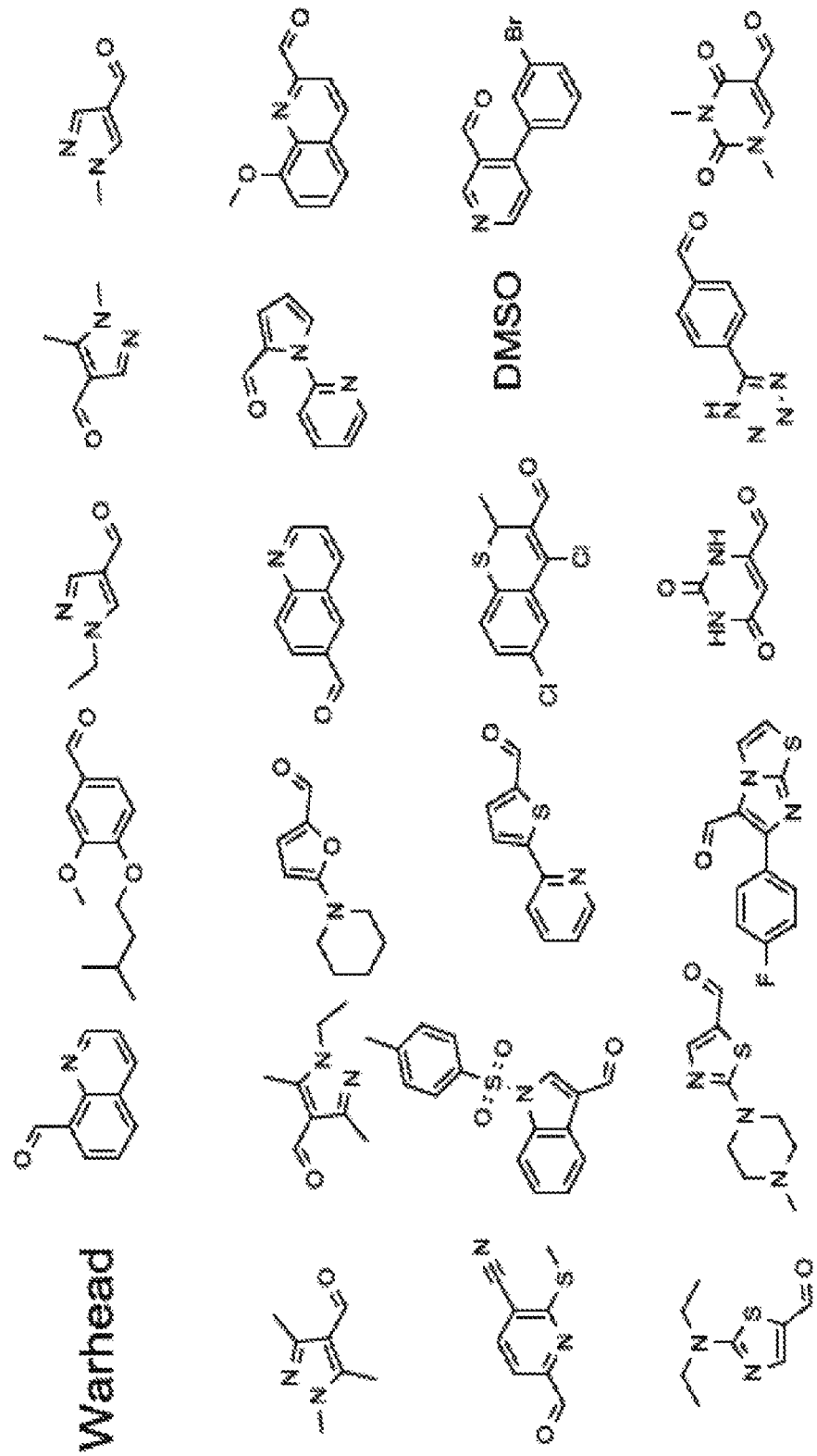
Figure 11B:
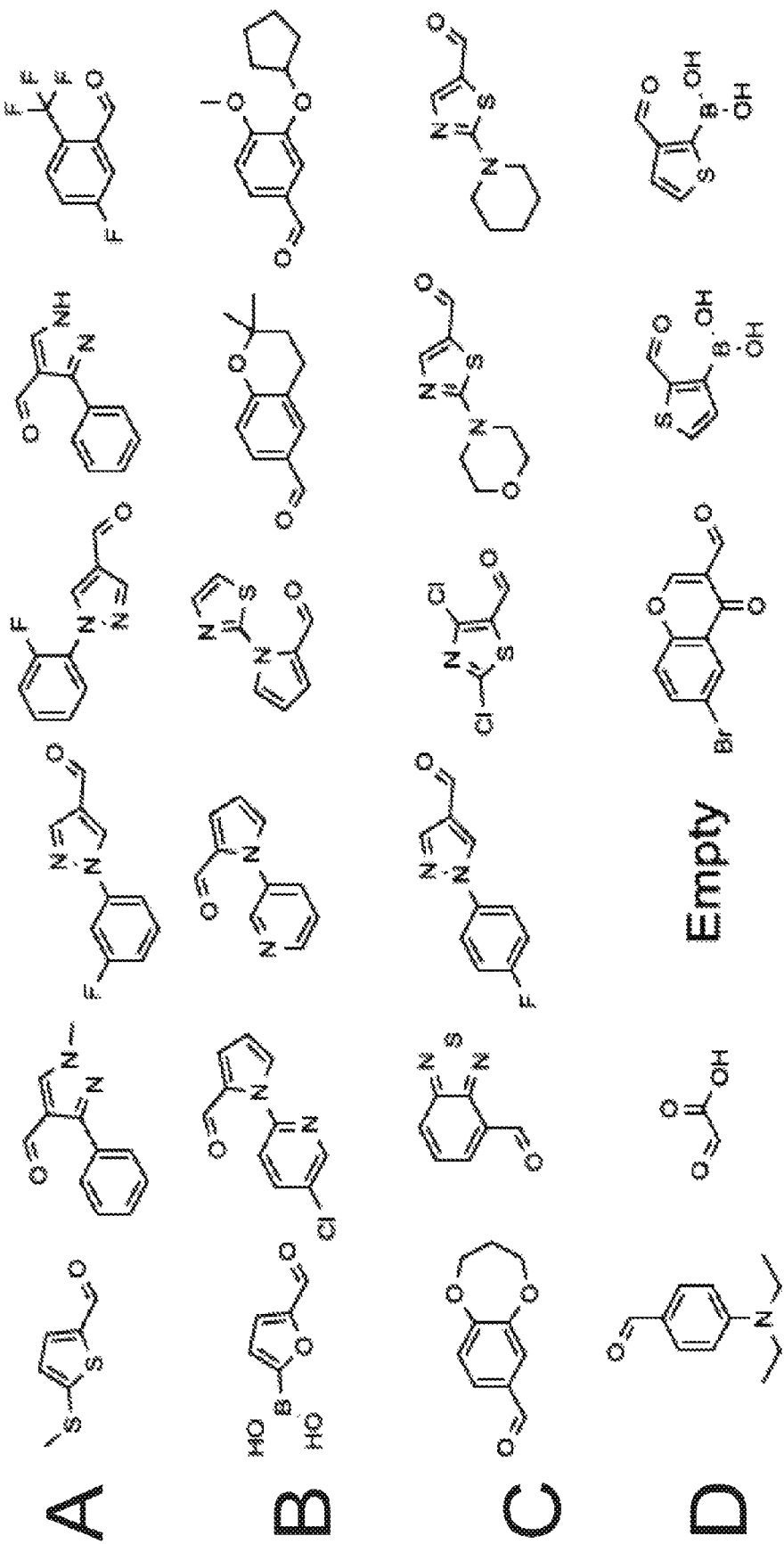
Figure 11B:
Figure 11B:
Figure 11B:
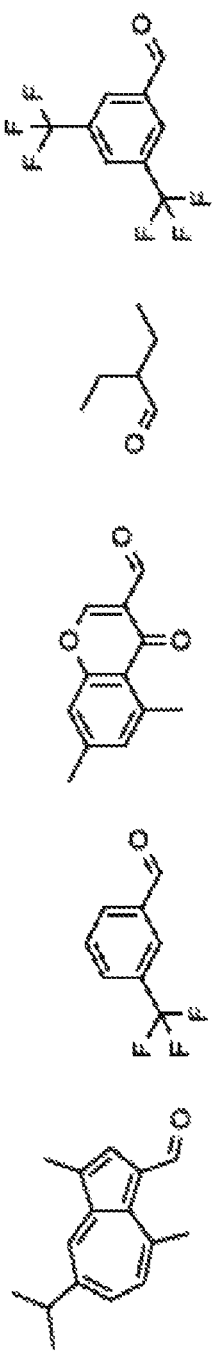
Figure 11B:
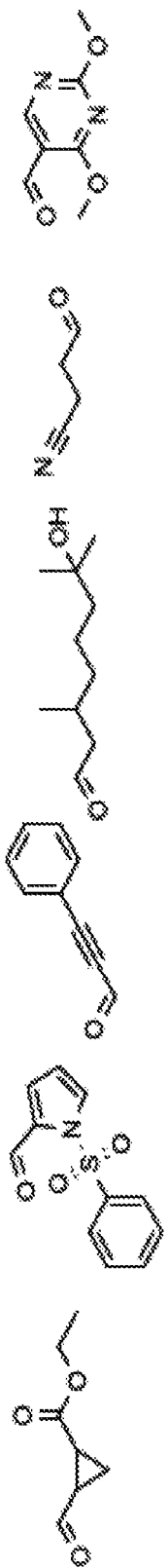
Figure 11C:
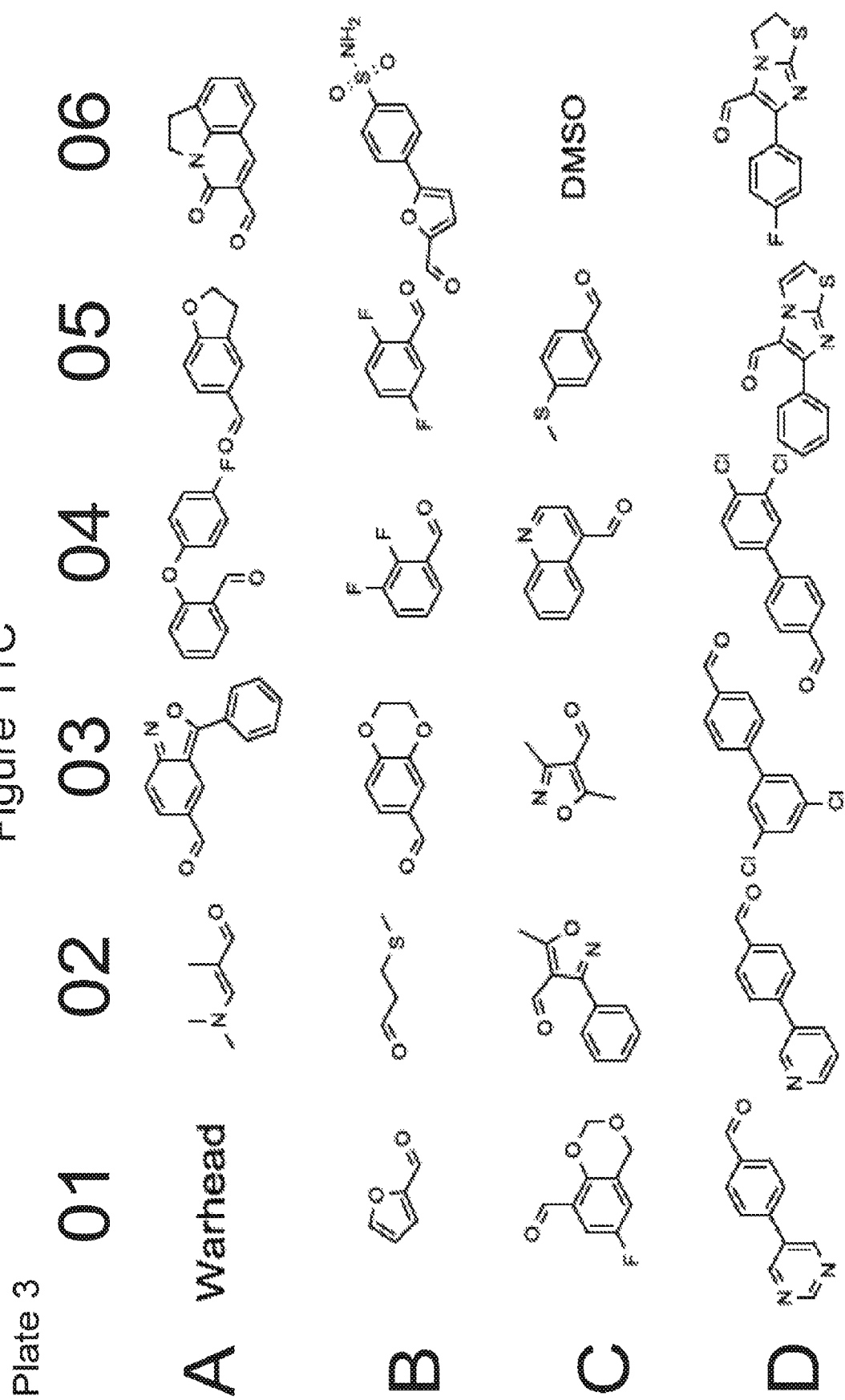
Figure 11C:
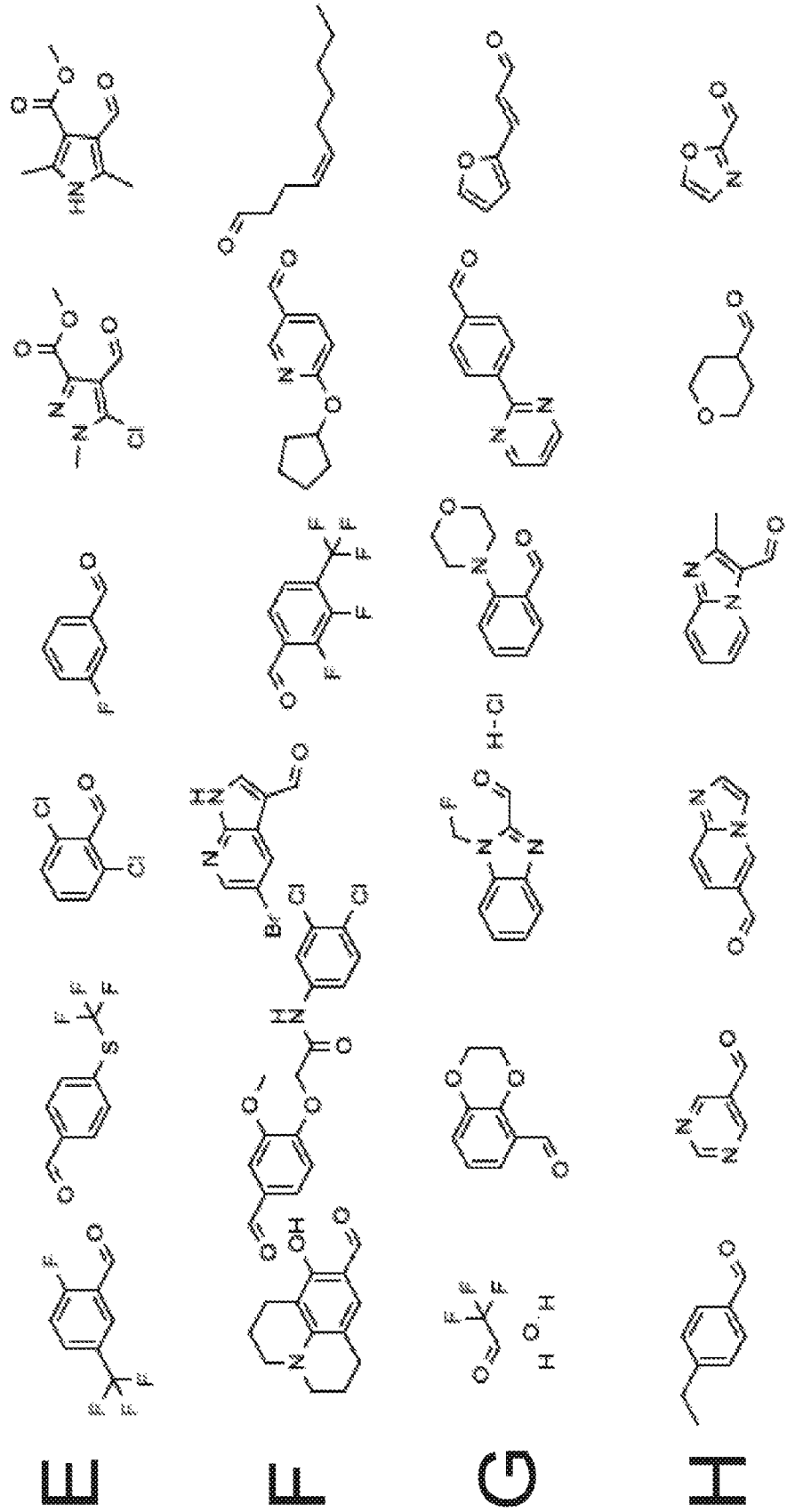
Figure 11C:
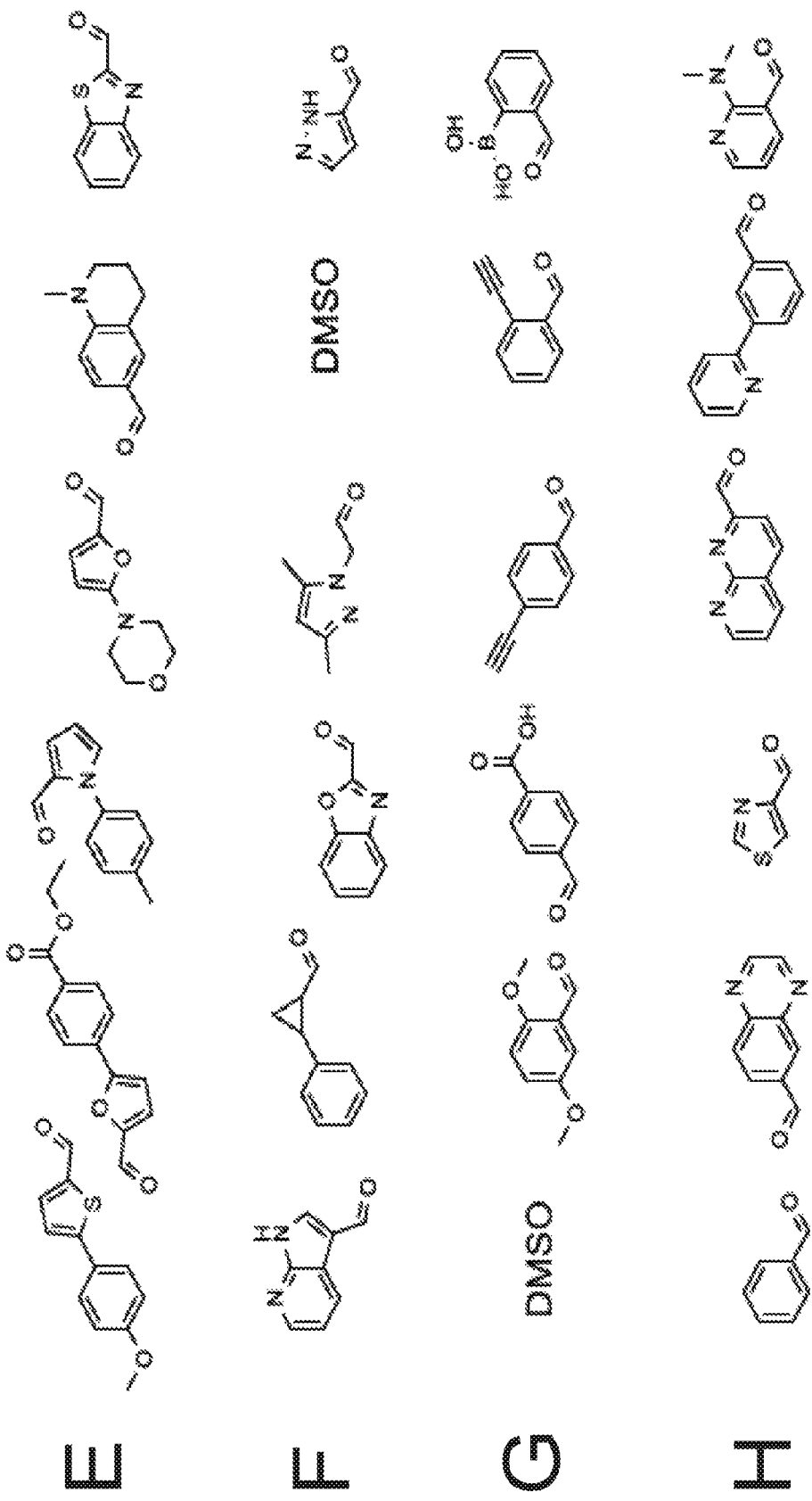
Figure 11D:
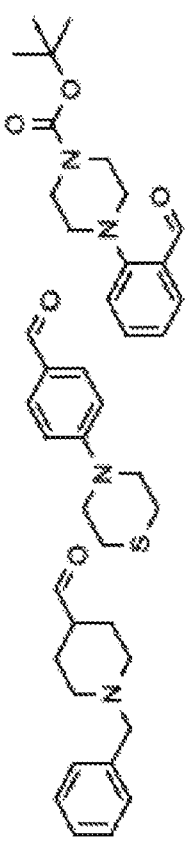
Figure 11D:
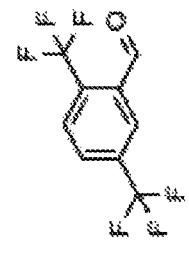
Figure 11D:
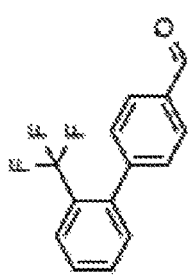
Figure 11D:
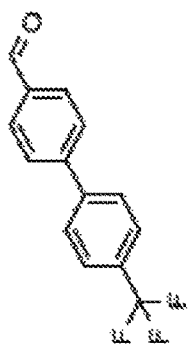
Figure 11D:
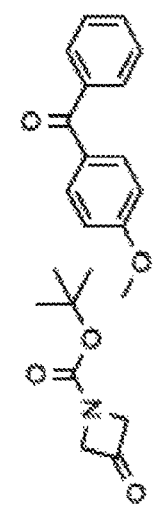
Figure 11D:
Figure 11D:
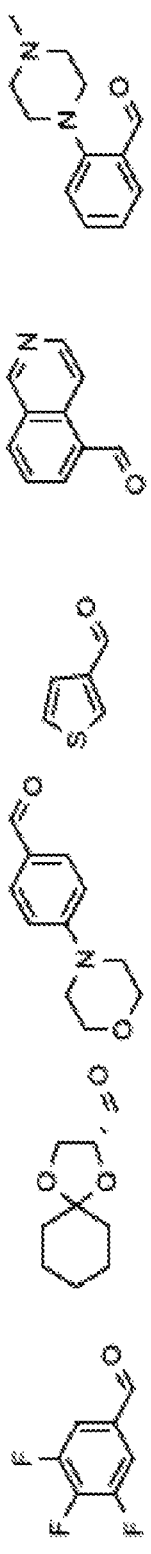
Figure 11D:
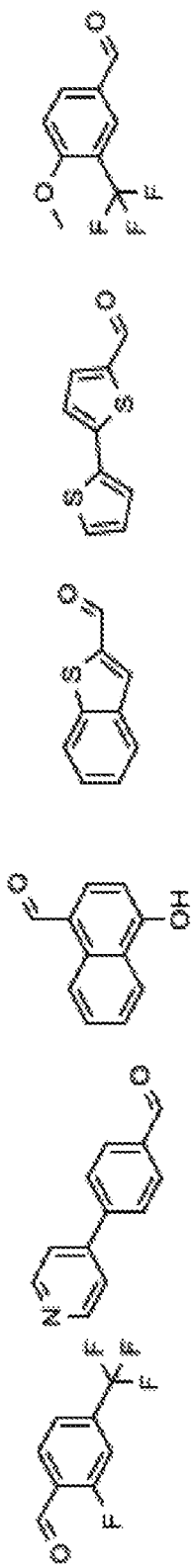
Figure 11D:
Figure 11D:
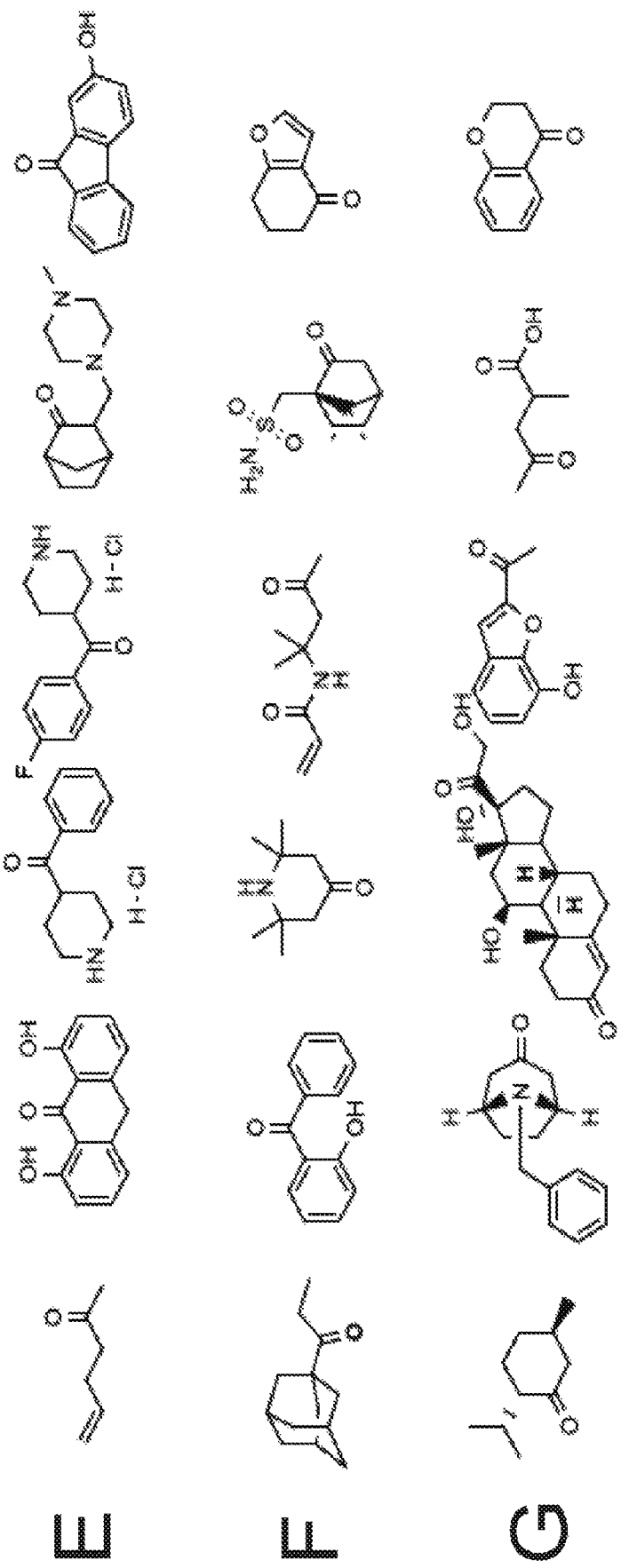
Figure 11D:
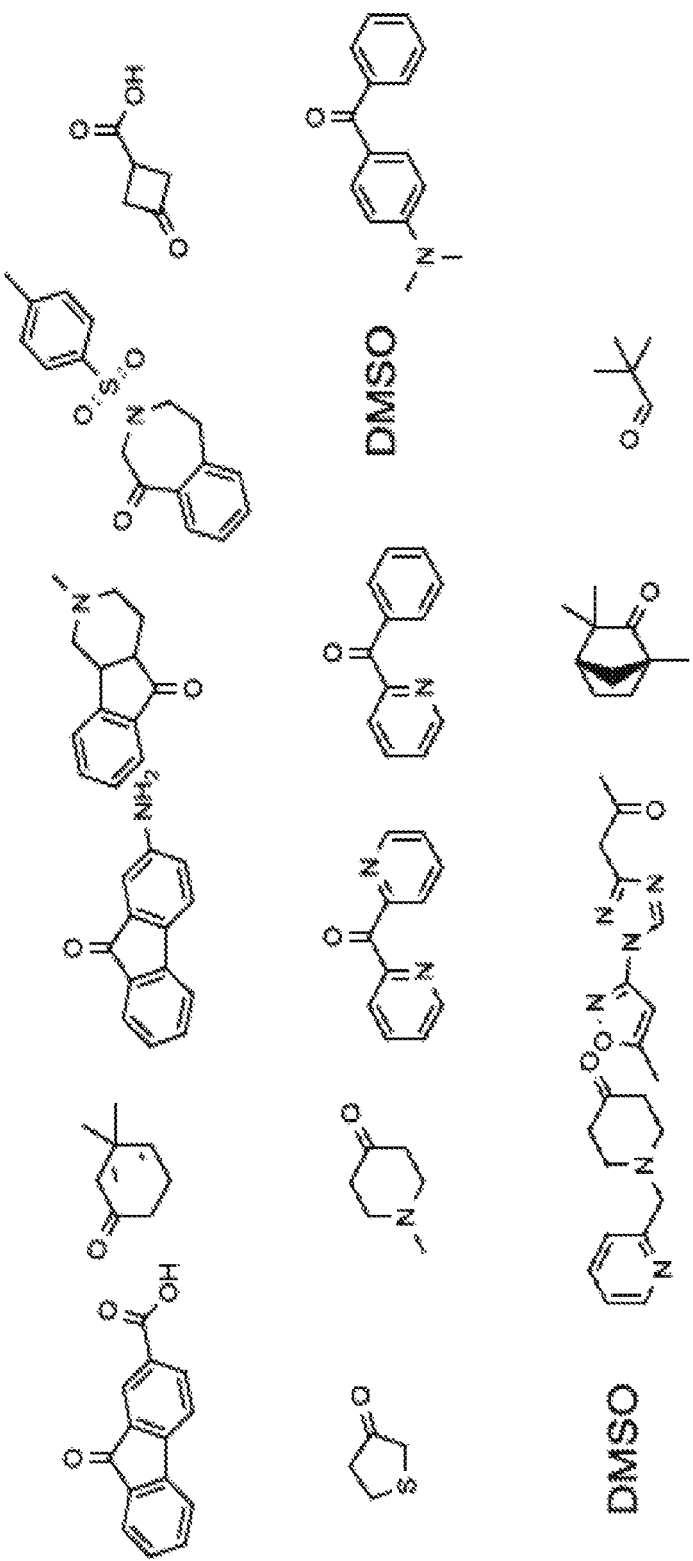
Figure 12A:
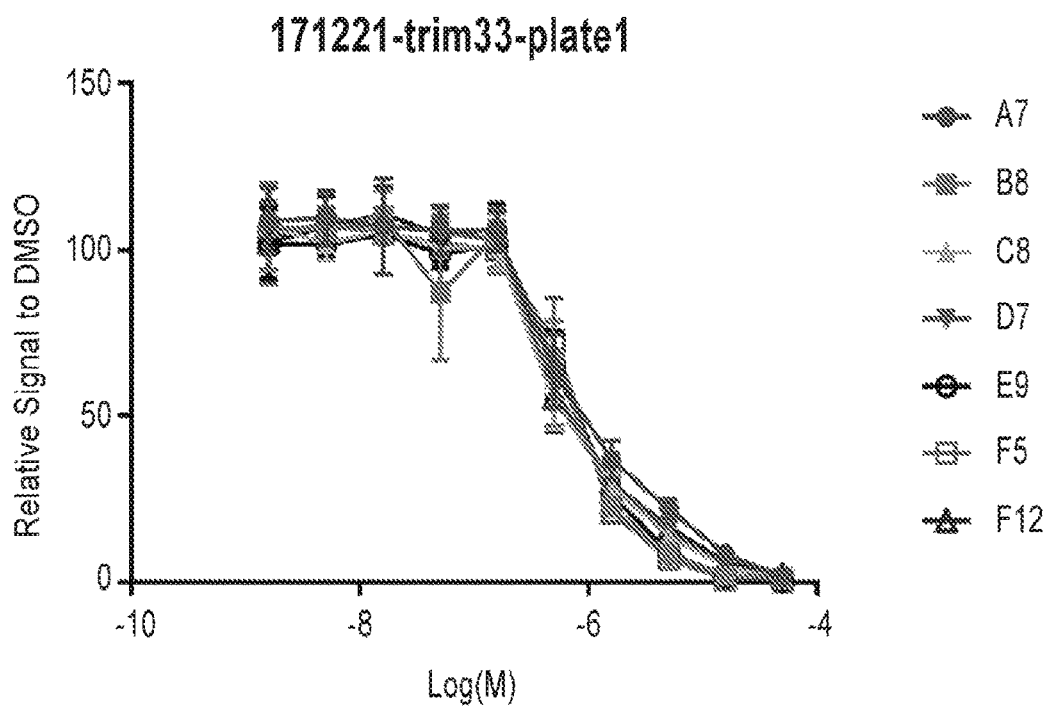
FIGS. 12A-12D are plots displaying TRIM33 and TRIM24 modulating activities of compounds which have the $R_7/R_7'$ in the formulae described in the present application as shown in FIG. 11A.
Figure 12B:
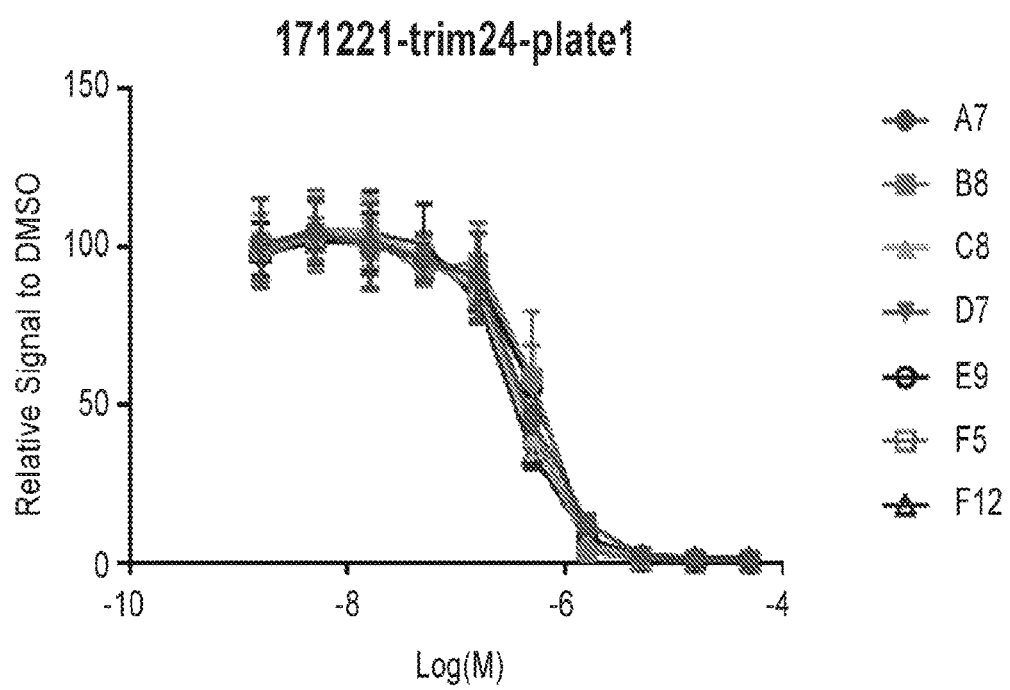
Figure 12C:
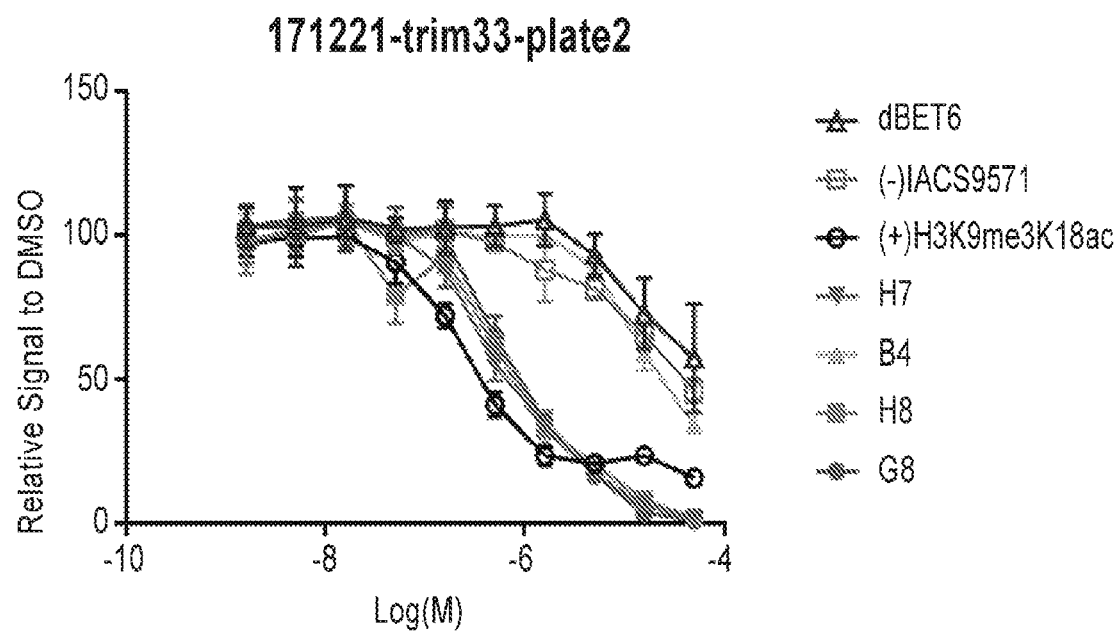
Figure 12D:
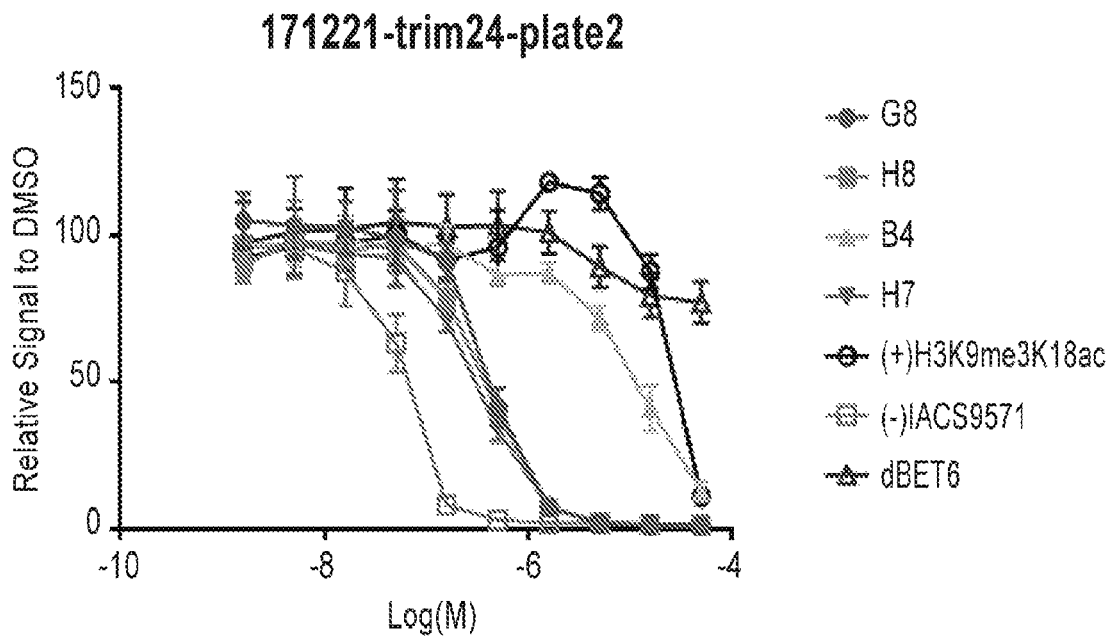

$IC_{50}$ of TRIM 33 and TRIM24 for the compounds which have the $R_7/R_7'$ in the formulae described in the present application shown in FIG. 11A.

|  | $IC_{50}$ (uM) | |
|---|---|---|
|  | TRIM33 | TRIM24 |
| A7 | 0.3054 | 0.1802 |
| B8 | 0.2834 | 0.2252 |
| C8 | 0.2403 | 0.1566 |
| D7 | 0.2498 | 0.1663 |
| E9 | 0.2994 | 0.2213 |
| F5 | 0.3006 | 0.2197 |
| F12 | 0.2335 | 0.1358 |
| G8 | 0.3357 | 0.1648 |
| H8 | 0.3256 | 0.162 |
| B4 | 5.484 | 7.862 |
| H7 | 0.2689 | 0.1334 |
| (+)H3K9me3K18ac | 0.1007 | — |
| (−)IACS9571 | 13.43 | 0.02583 |
| dBET6 | 4.69 | 1.96 |

TABLE 7

Figure 13A:
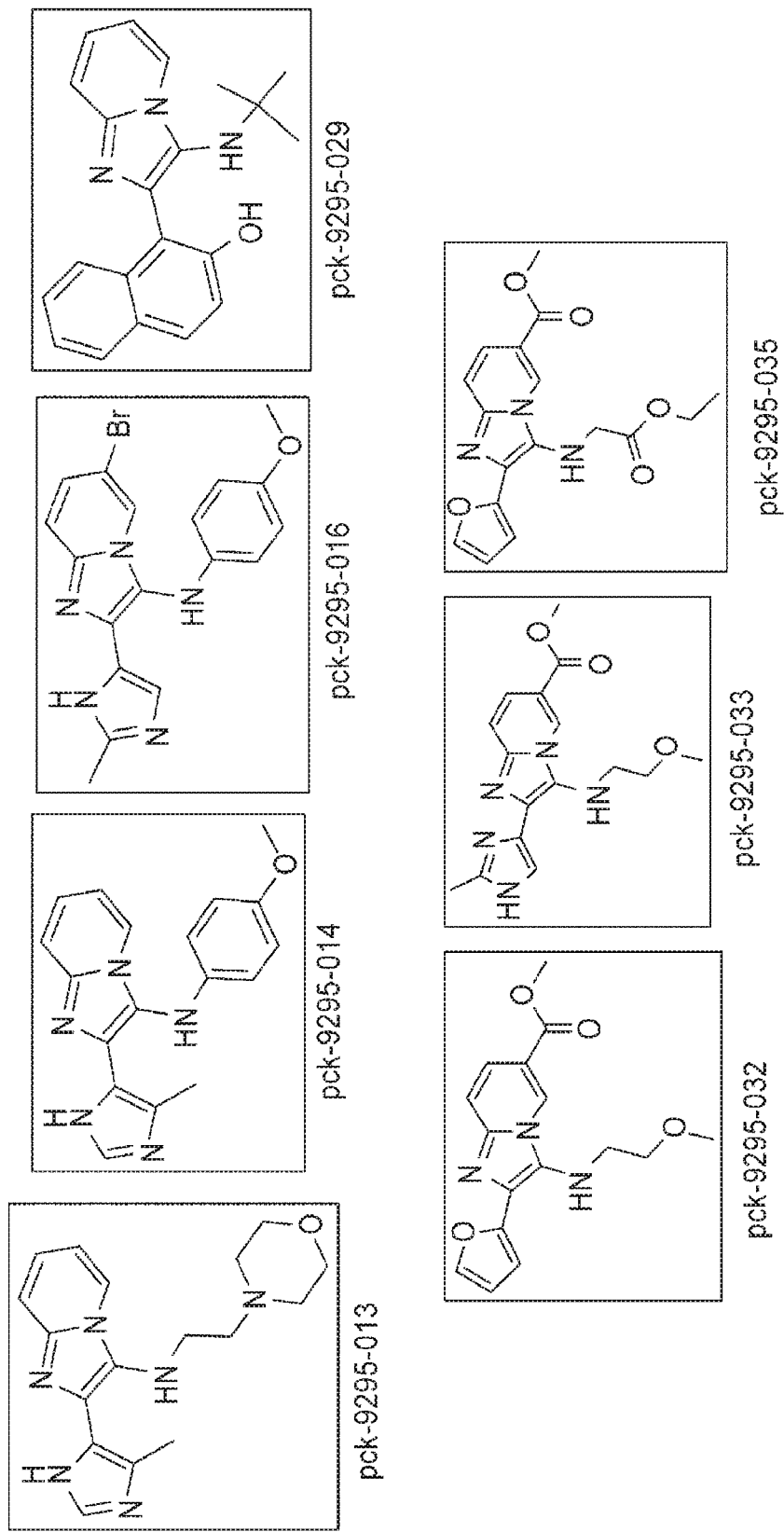
FIGS. 13A-13C are chemical structures of compounds of the present application (FIG. 13A) and corresponding plots displaying TRIM33 and TRIM24 modulating activities of the compounds.
Figure 13B:
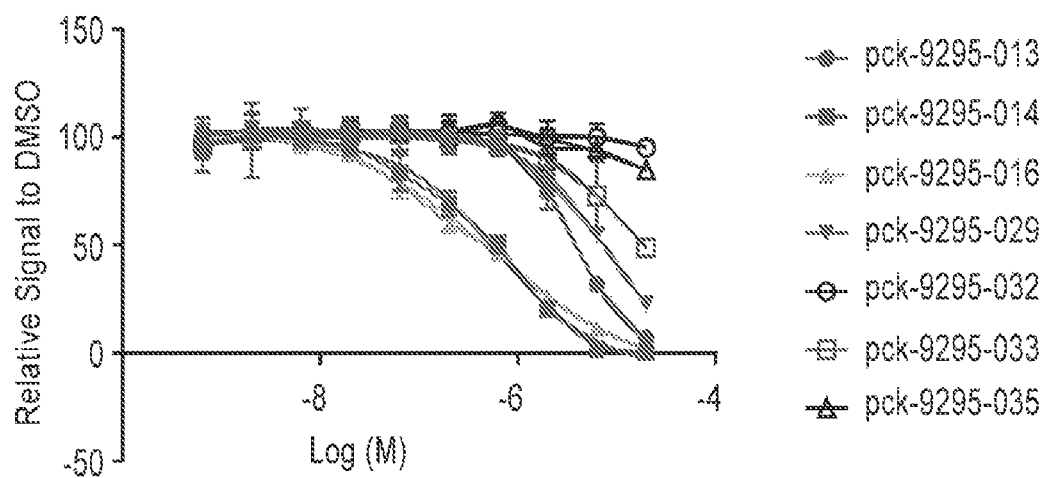
Figure 13C:
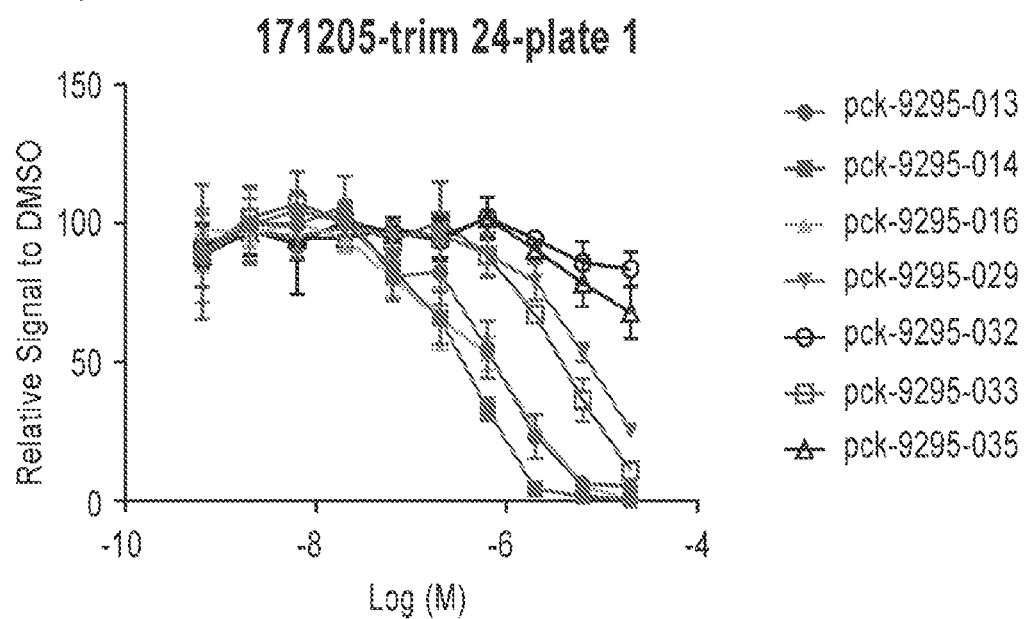

$IC_{50}$ of TRIM33 and TRIM24 for the compounds shown in FIG. 13A.

|  | TRIM 24 $IC_{50}$ (uM) | TRIM 33 $IC_{50}$ (uM) |
|---|---|---|
| pck-9295-013 | 0.7464 | 3.777 |
| pck-9295-014 | 0.356 | 0.641 |
| pck-9295-016 | 0.8183 | 0.5379 |
| pck-9295-029 | 7.763 | 7.451 |
| pck-9295-032 | Not Converged | 21.78 |
| pck-9295-033 | 4.072 | 10.51 |
| pck-9295-035 | 5.247 | 10.76 |

TABLE 8

Figure 14A:
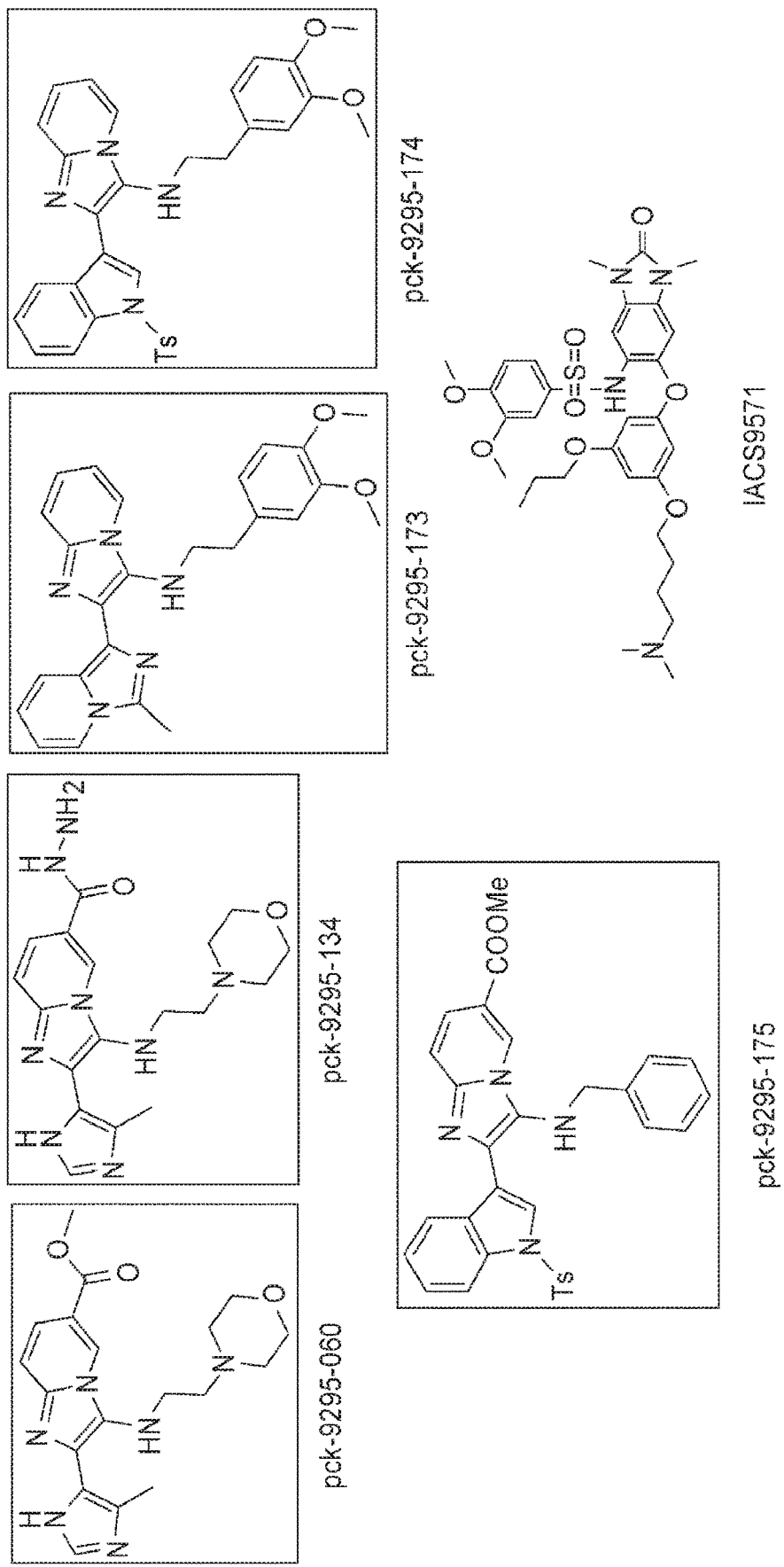
FIGS. 14A-14C are chemical structures of compounds of the present application (FIG. 14A) and corresponding plots displaying TRIM33 and TRIM24 modulating activities of the compounds.
Figure 14B:
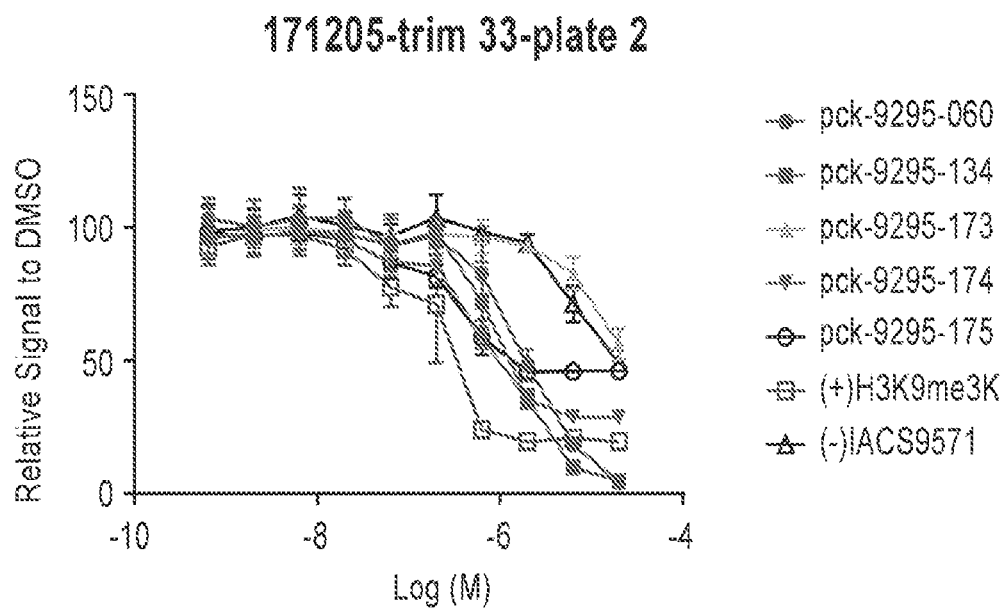
Figure 14C:
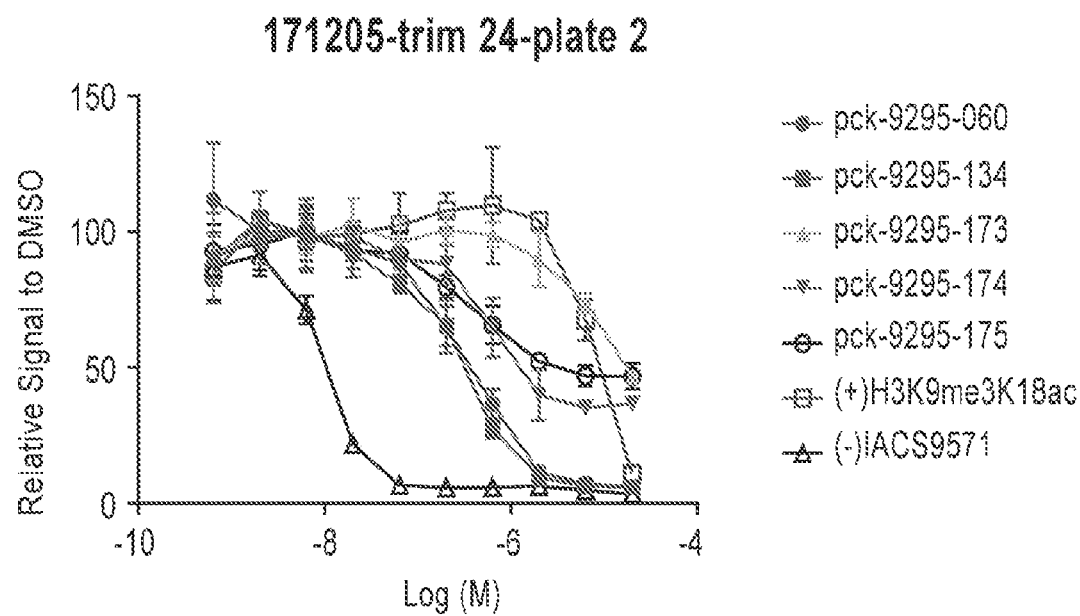
Figure 15A:
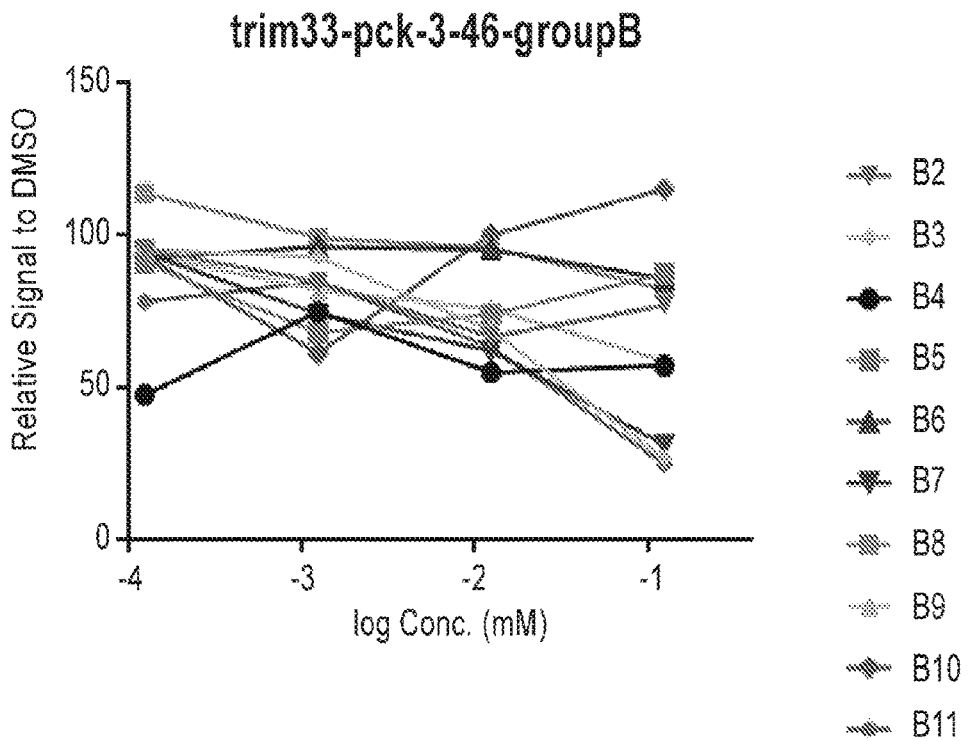
FIGS. 15A-15L are plots showing TRIM33 and TRIM24 modulating activities of compounds of the present application as listed in Table 2e.
Figure 15B:
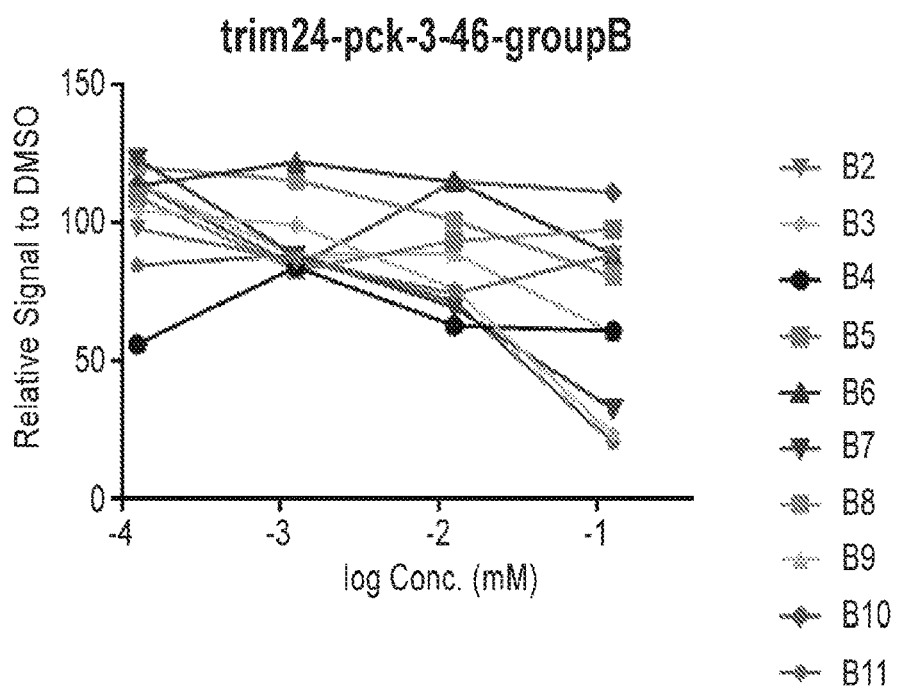
Figure 15C:
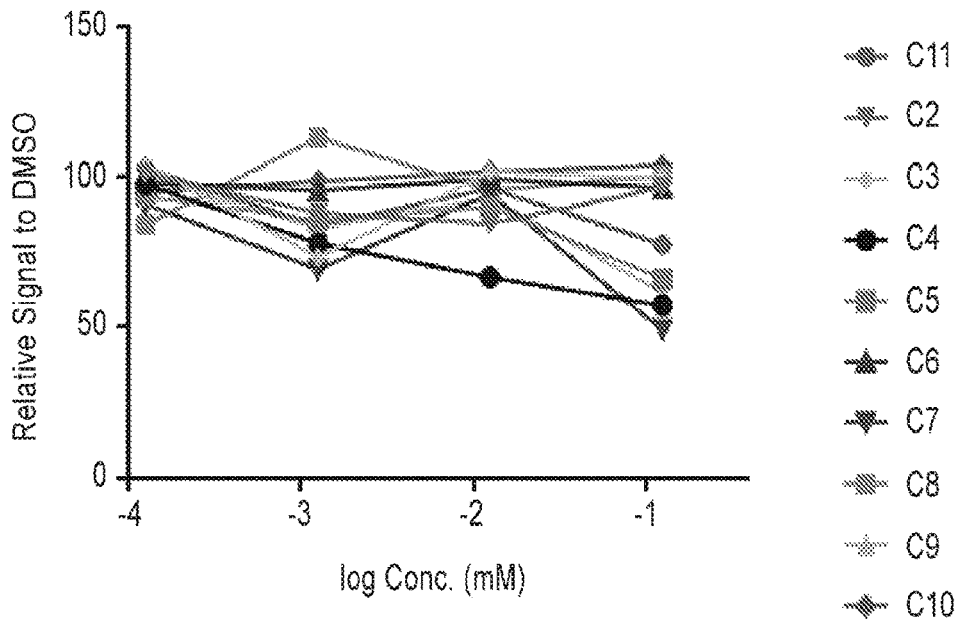
Figure 15D:
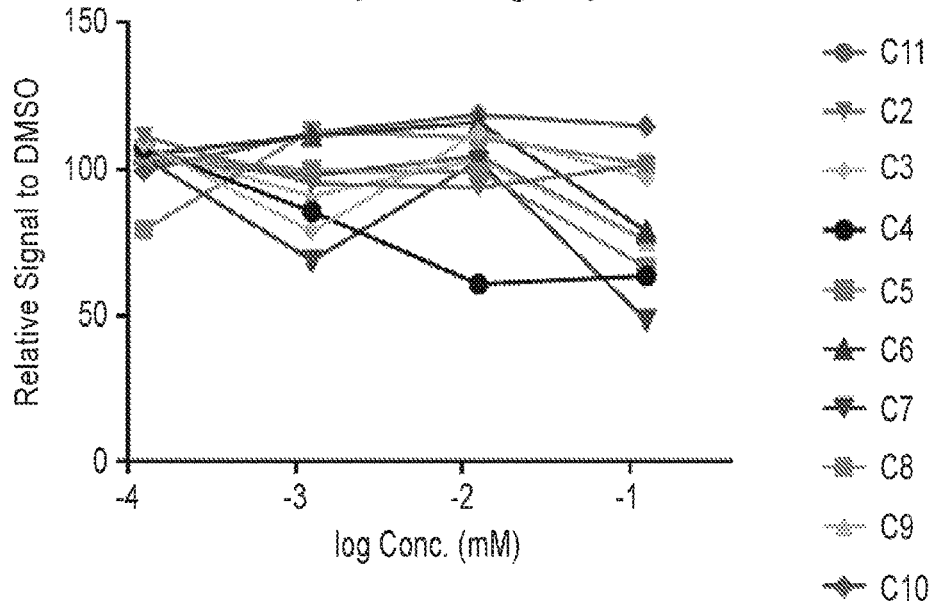
Figure 15E:
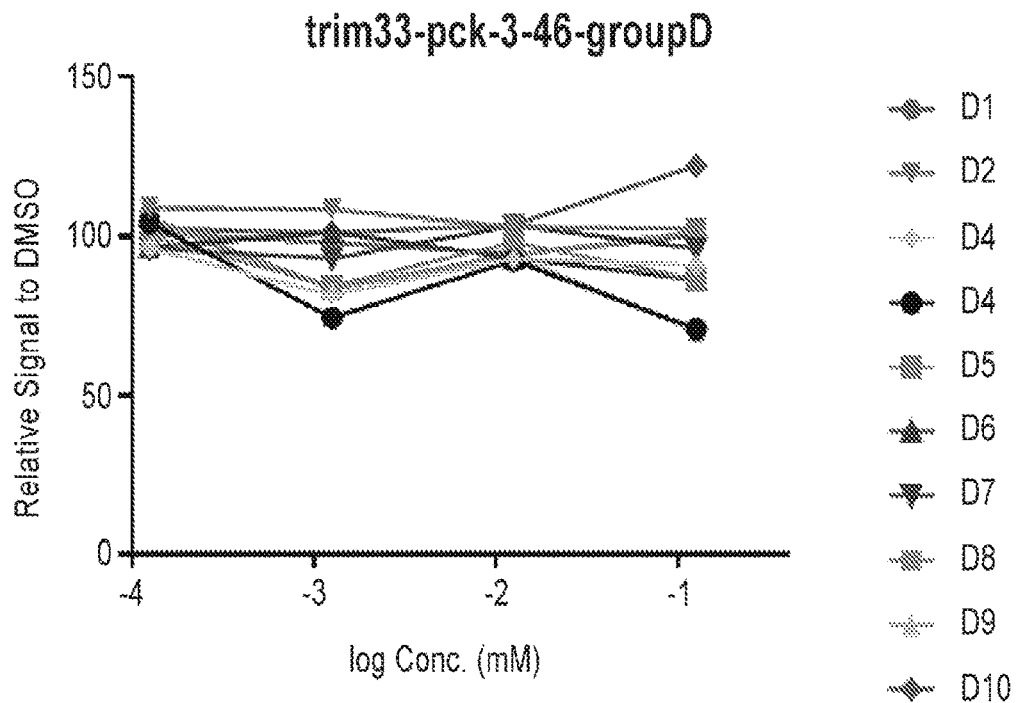
Figure 15F:
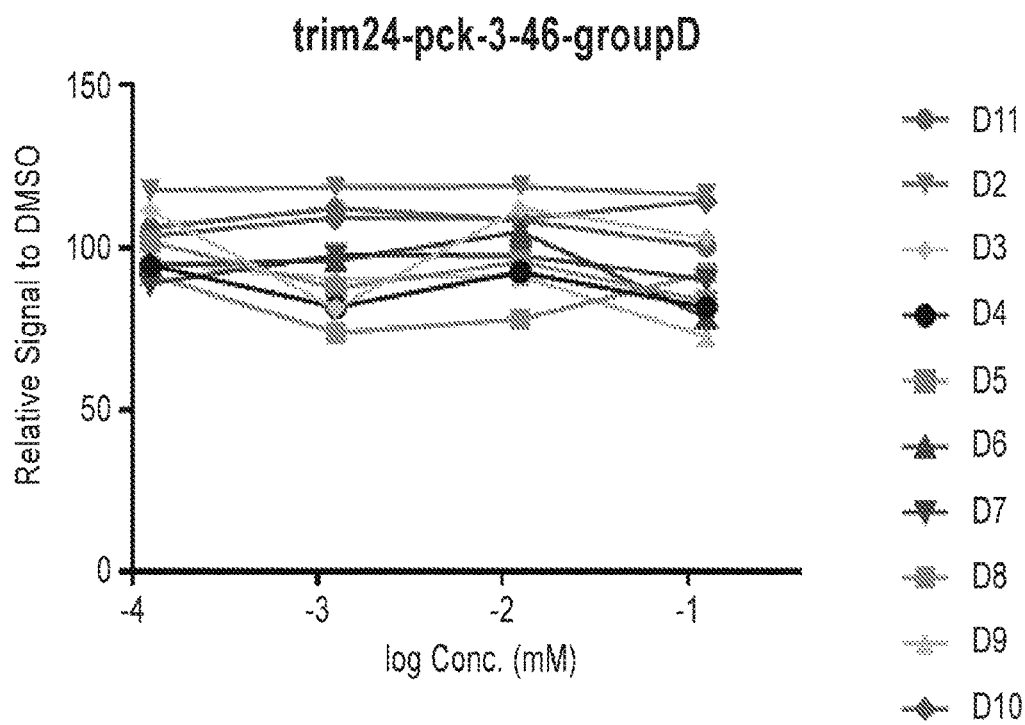
Figure 15G:
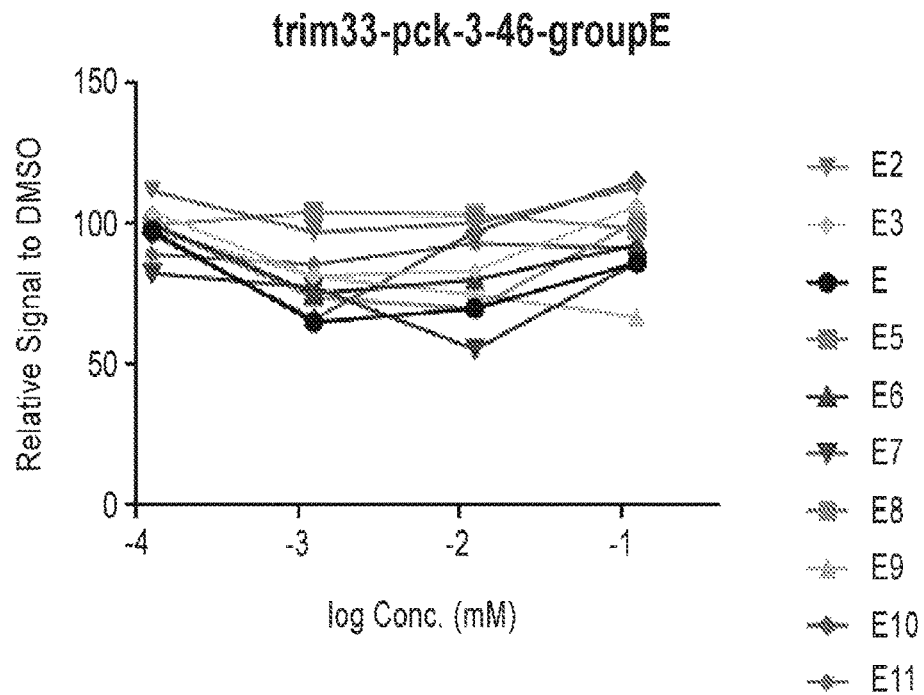
Figure 15H:
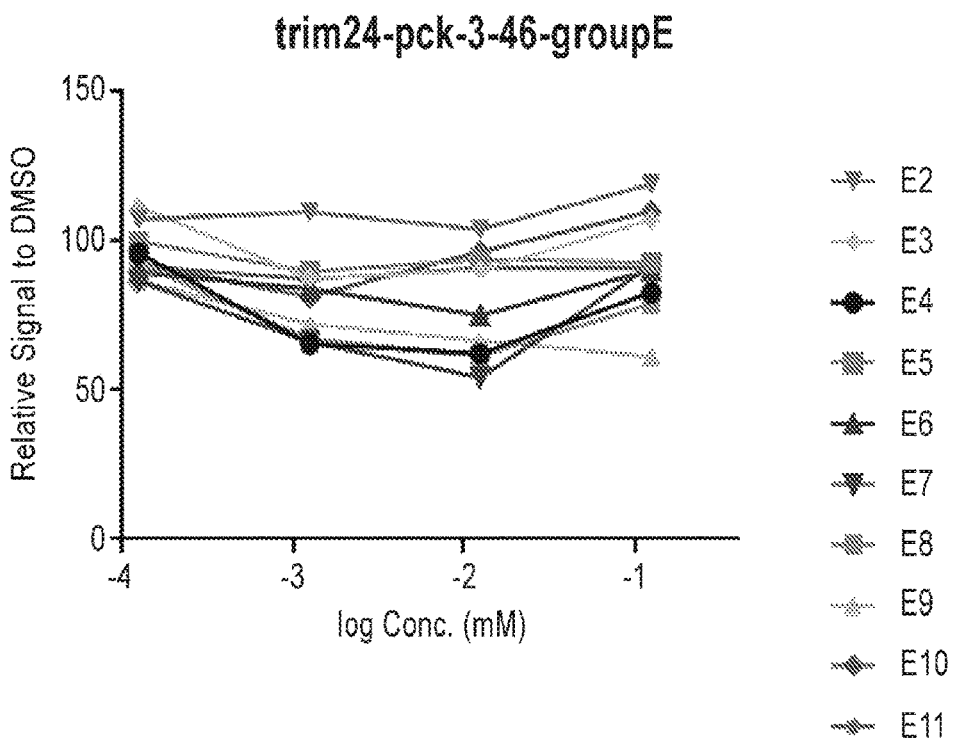
Figure 15I:
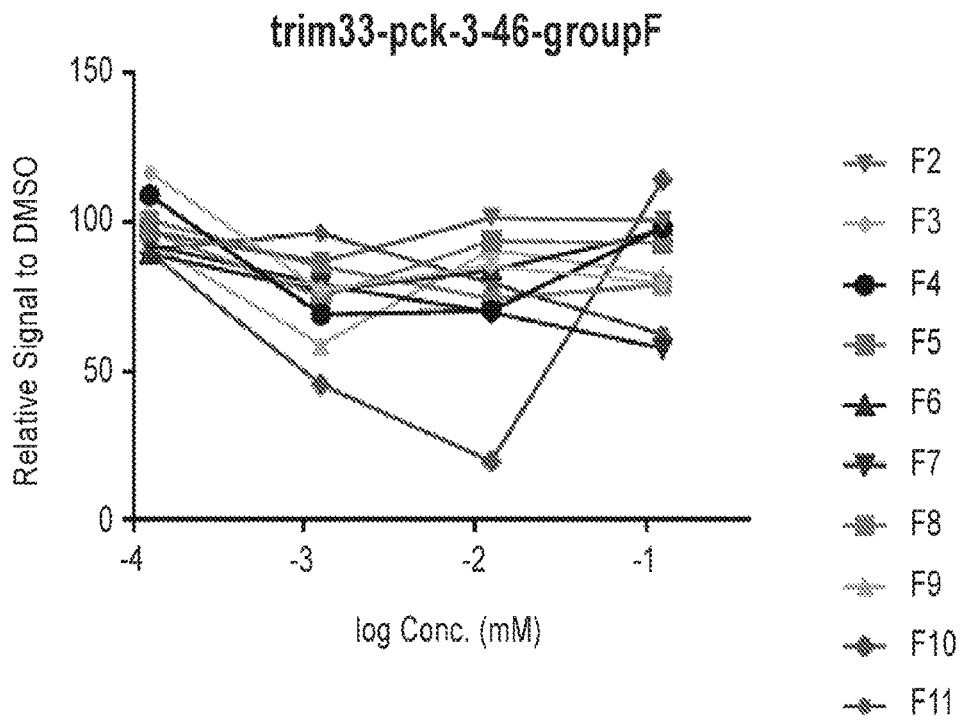
Figure 15J:
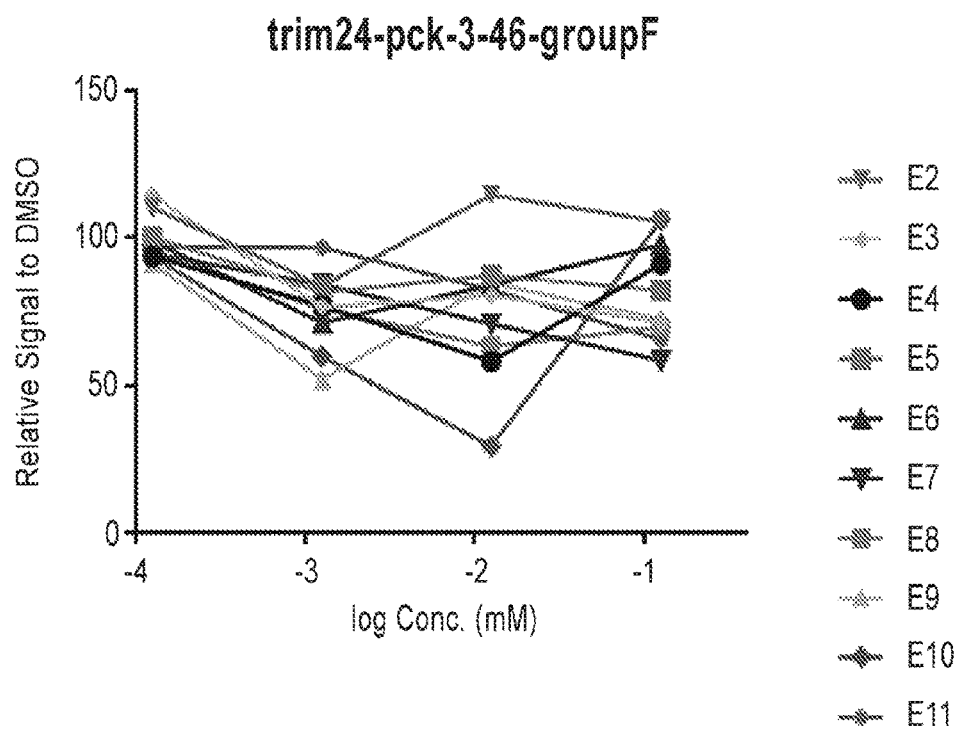
Figure 15K:
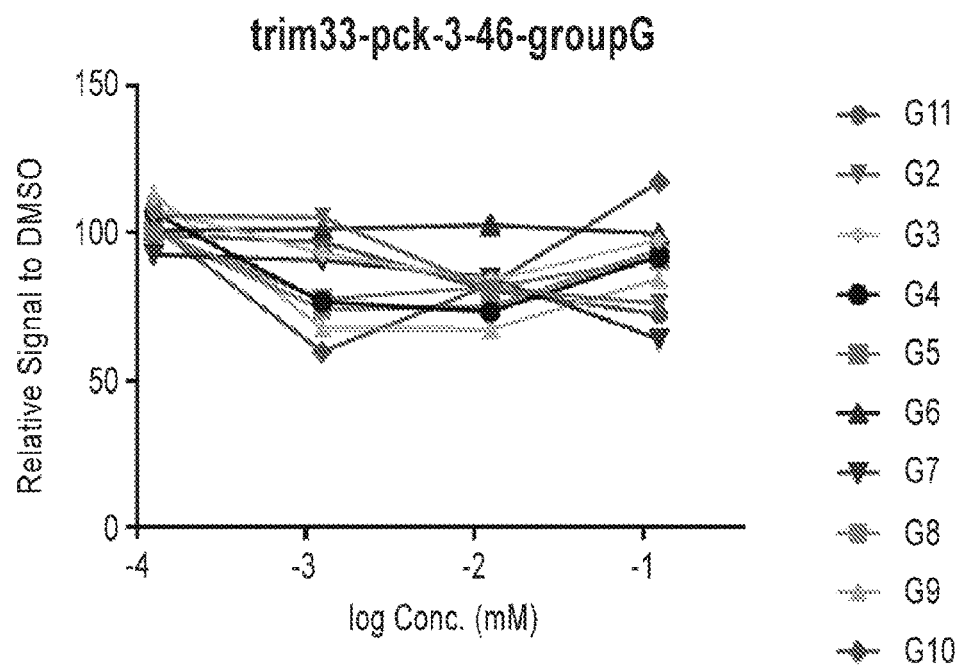
Figure 15L:
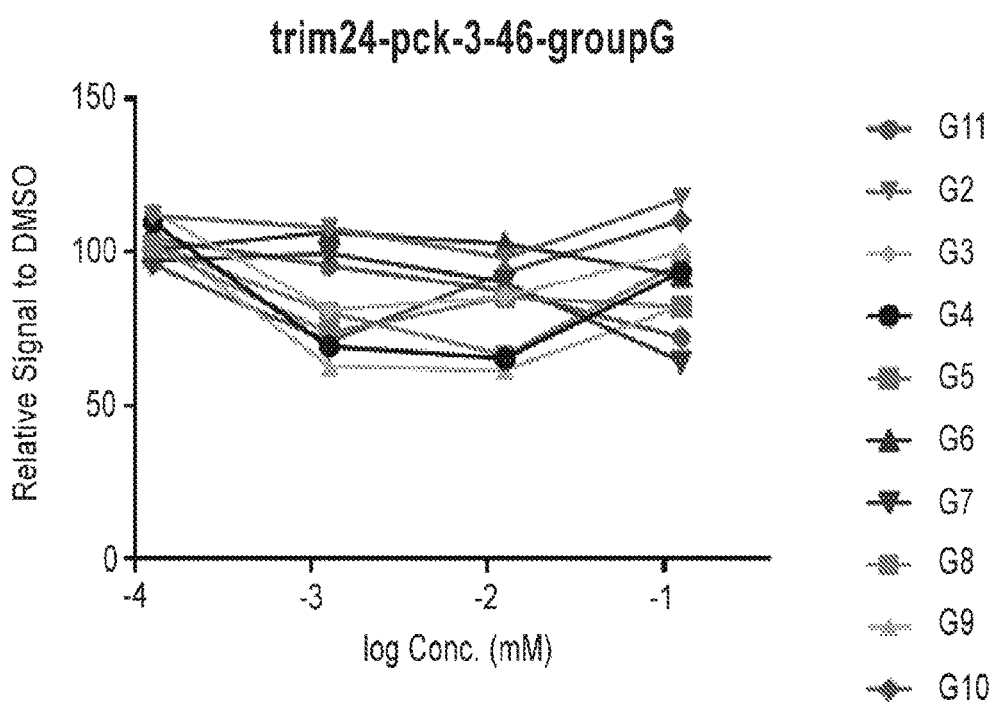
Figure 16A:
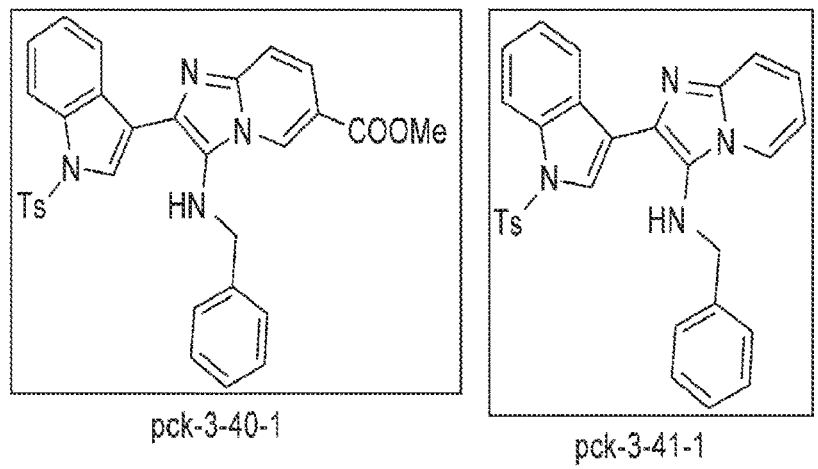
FIGS. 16A-16C are chemical structures of compounds of the present application (FIG. 16A) and corresponding plots displaying TRIM33 and TRIM24 modulating activities of the compounds.
Figure 16B:
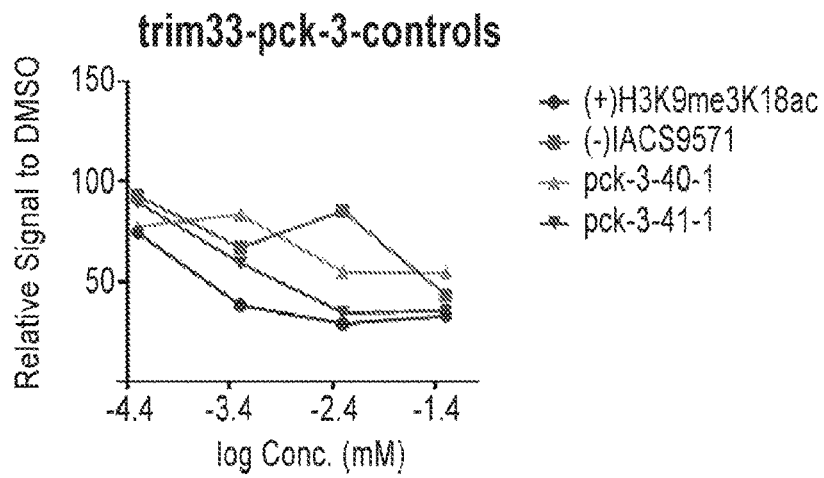
Figure 16C:
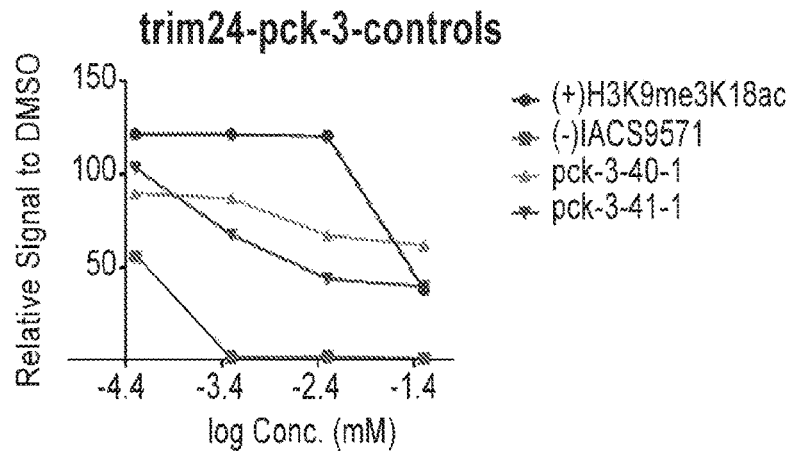

$IC_{50}$ of TRIM33 and TRIM24 for the compounds shown in FIG. 14A.

|  | TRIM 24 $IC_{50}$ (uM) | TRIM 33 $IC_{50}$ (uM) |
|---|---|---|
| pck-9295-060 | 0.3082 | 1.934 |
| pck-9295-134 | 0.3035 | 1.294 |
| pck-9295-173 | 9.444 | 44.34 |

TABLE 8-continued

IC$_{50}$ of TRIM33 and TRIM24 for the compounds shown in FIG. 14A.

| | TRIM 24 IC$_{50}$ (uM) | TRIM 33 IC$_{50}$ (uM) |
|---|---|---|
| pck-9295-174 | 0.5842 | 0.5532 |
| pck-9295-175 | 0.4153 | 0.3198 |
| (+)H3K9me3K18ac | 6.69E+00 | 0.2527 |
| (−)IACS9571 | 0.01107 | 6.323 |

Equivalents

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula Ic:

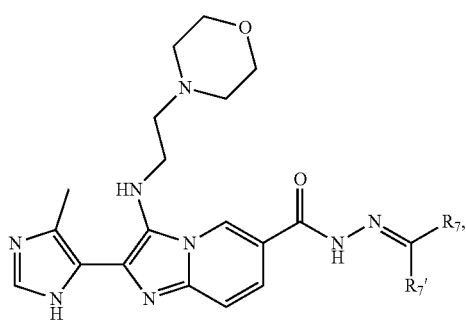

(Ic)

or a pharmaceutically acceptable salt or ester thereof, wherein:
R$_7$ and R$_7$' are each independently H, (C$_1$-C$_4$) alkyl, (C$_1$-C$_4$) haloalkyl, or (CHR$_5$)$_{n2}$-R$_7$a, or R$_7$ and R$_7$', together with the carbon atom to which they are attached, form a C$_3$-C$_8$ cycloalkyl, C$_3$-C$_8$ cycloalkenyl, or a heterocyclyl having one, two, or three 4- to 7-membered rings and 1-4 heteroatoms selected from N, O, and S, wherein the two or three 4- to 7-membered rings are fused, and wherein the cycloalkyl, cycloalkenyl, or heterocyclyl is optionally substituted with one or more R$_{sb2}$;
R$_{7a}$ is OH, SH, S(C$_1$-C$_4$) alkyl, (C$_1$-C$_4$) alkoxy, (C$_1$-C$_4$) haloalkoxy, O—C$_6$-C$_{10}$ aryl, NH$_2$, NH(C$_1$-C$_4$) alkyl, N((C$_1$-C$_4$) alkyl)$_2$, C(O)OH, C(O)(C$_1$-C$_4$) alkyl, C(O)O(C$_1$-C$_4$) alkyl, C(O)NH(C$_1$-C$_4$) alkyl, NHC(O)(C$_1$-C$_4$) alkyl, NHC(O)O(C$_1$-C$_4$) alkyl, NHC(O)NH(C$_1$-C$_4$) alkyl, (C$_2$-C$_8$) alkenyl, (C$_2$-C$_8$) alkynyl, C$_3$-C$_8$ cycloalkyl, C$_3$-C$_8$ a cycloalkenyl, or a heterocyclyl having one, two, or three 4- to 7-membered rings and 1-4 heteroatoms selected from N, O, and S, wherein the two or three 4- to 7-membered rings are fused, or heteroaryl having one or two 5- or 6-membered rings and 1-4 heteroatoms selected from N, O, and S, wherein the two 5- or 6-membered rings are fused, and wherein the alkenyl, alkynyl, cycloalkyl, cycloalkenyl, heterocyclyl, aryl, or heteroaryl is optionally substituted with one or more R$_{sb2}$;
n2 is 0, 1, 2, 3, 4, 5, 6, 7, 8, 9, or 10;

each R$_{sb2}$ is independently (C$_1$-C$_6$) alkyl, (C$_1$-C$_6$) haloalkyl, (C$_1$-C$_6$) alkoxy, (C$_1$-C$_6$) haloalkoxy, (C$_2$-C$_6$) alkenyl, (C$_2$-C$_6$) alkynyl, halogen, nitro, CN, oxo, B(OH)$_2$, OH, SH, S(C$_1$-C$_6$) alkyl, NH$_2$, NH(C$_1$-C$_4$) alkyl, N((C$_1$-C$_4$) alkyl)$_2$, NH(C$_6$-C$_{10}$) aryl, N((C$_6$-C$_{10}$) aryl)$_2$, C(O)OH, C(O)(C$_1$-C$_4$) alkyl, C(O)O(C$_1$-C$_4$) alkyl, C(O)NH(C$_1$-C$_4$) alkyl, NHC(O)(C$_1$-C$_4$) alkyl, NHC(O)O(C$_1$-C$_4$) alkyl, NHC(O)NH(C$_1$-C$_4$) alkyl, S(O)$_o$R$_6$, S(O)$_2$NH$_2$, O—C$_3$-C$_8$ cycloalkyl, O—C$_3$-C$_8$ cycloalkenyl, C$_3$-C$_8$ cycloalkyl, C$_3$-C$_8$ cycloalkenyl, heterocyclyl having one or two 4- to 7-membered rings and 1-4 heteroatoms selected from N, O, and S, C$_6$-C$_{10}$ aryl, or heteroaryl having one or two 5- or 6-membered rings and 1-4 heteroatoms selected from N, O, and S, wherein the cycloalkyl, cycloalkenyl, heterocyclyl, aryl, or heteroaryl is optionally substituted, and the two 4- to 7-membered rings and the two 5- or 6-membered rings are fused, and wherein the (C$_1$-C$_6$) alkyl or (C$_1$-C$_6$) alkoxy is optionally substituted with CN, OH, NH$_2$, NH(C$_1$-C$_4$) alkyl, or N((C$_1$-C$_4$) alkyl)$_2$;
each R$_5$ is independently H or (C$_1$-C$_4$) alkyl;
o is 0, 1, or 2; and
R$_6$ is OH, (C$_1$-C$_4$) alkyl, or C$_6$-C$_{10}$ aryl, wherein the aryl is optionally substituted.

2. A method of inhibiting TRIM33 or treating a disease or disorder in which TRIM33 plays a role in a subject in need thereof, comprising administering to the subject an effective amount of a compound of claim 1, or a pharmaceutically acceptable salt or ester thereof.

3. A compound, which is:

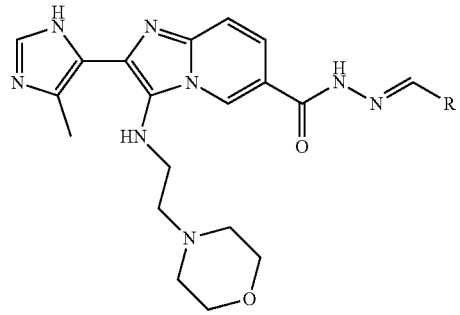

or a pharmaceutically acceptable salt or ester thereof, wherein R is selected from:

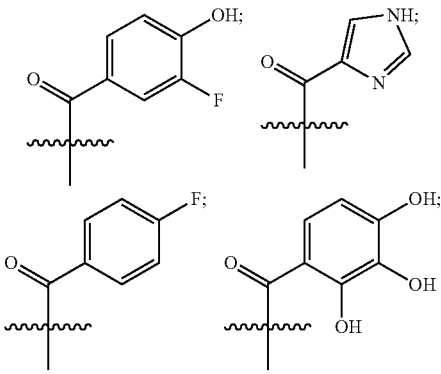

-continued
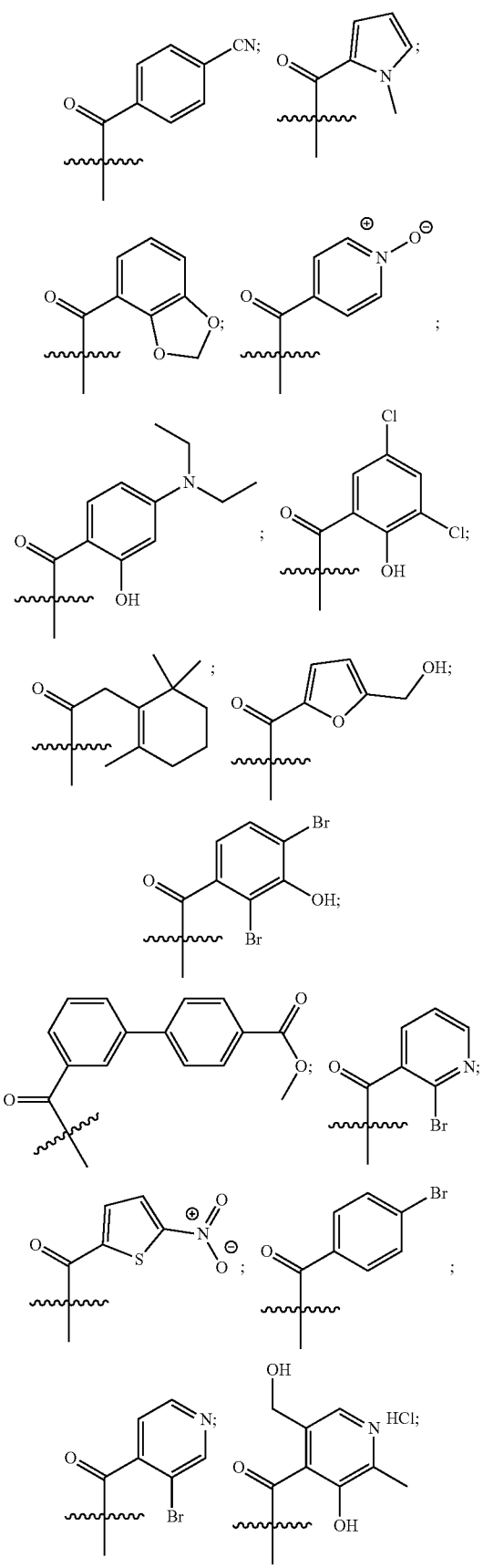
-continued
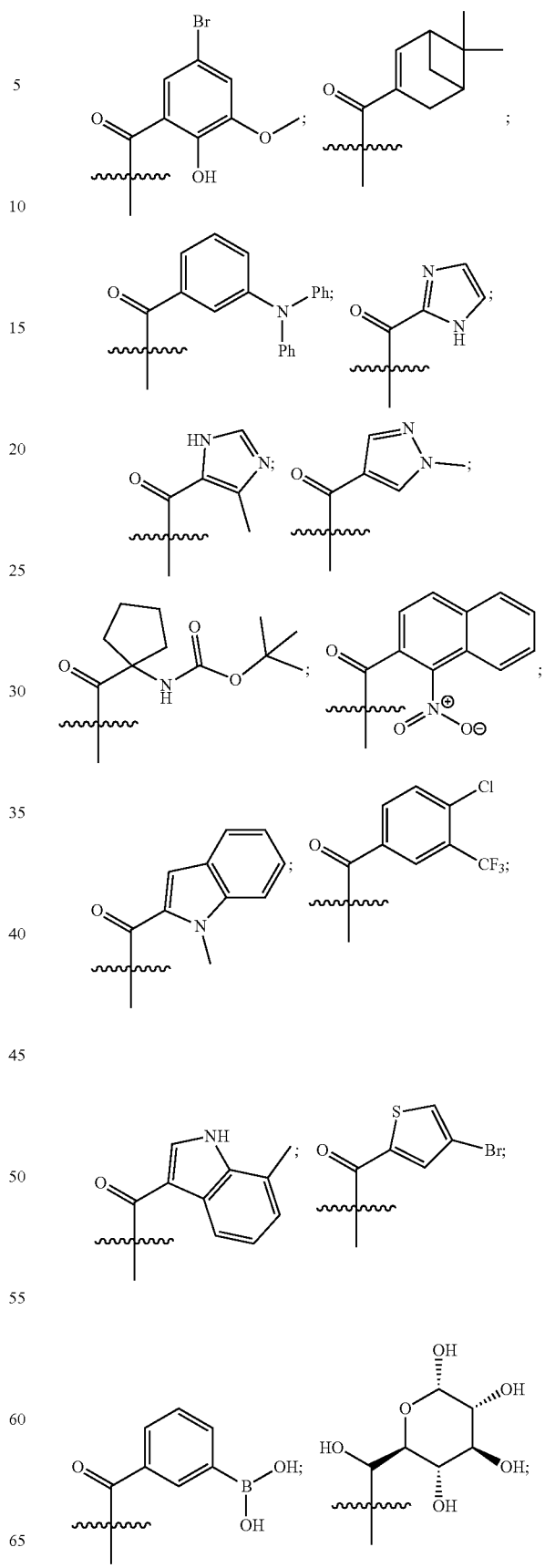

71
-continued
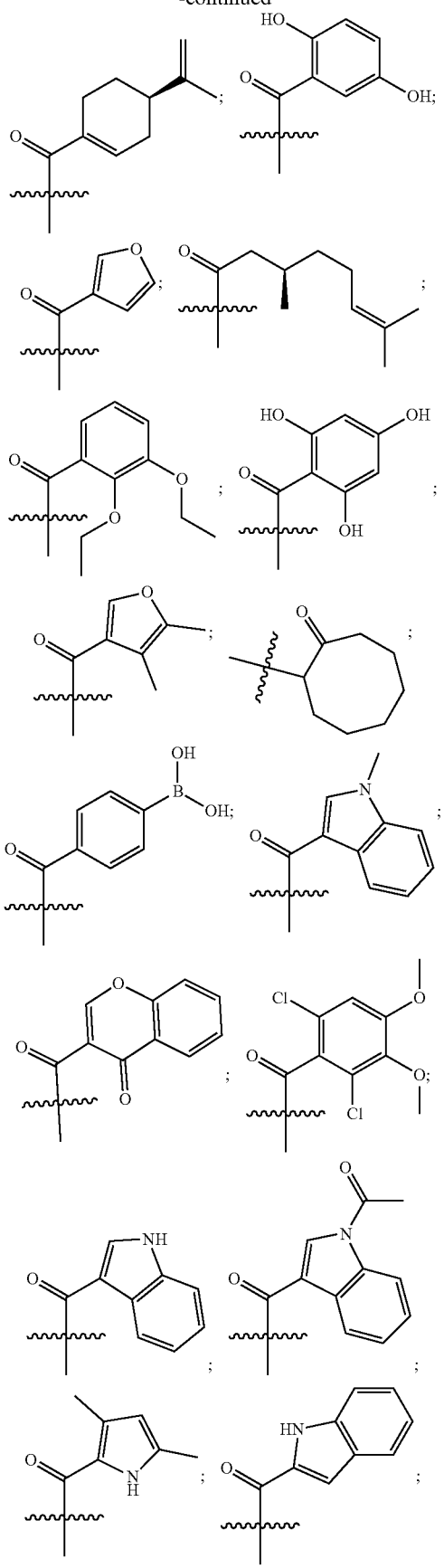
72
-continued
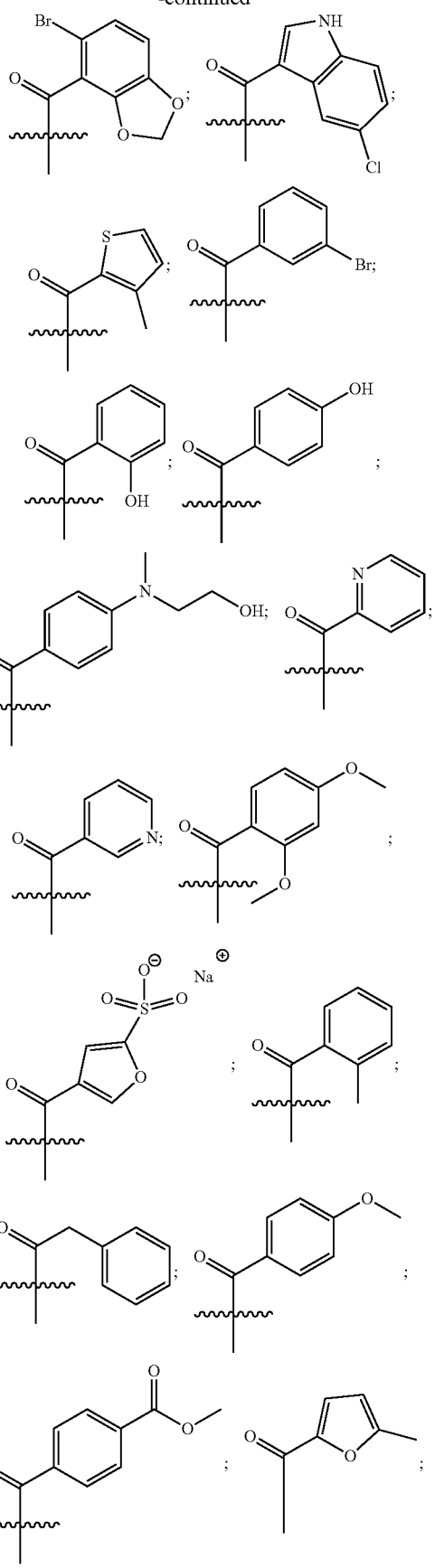

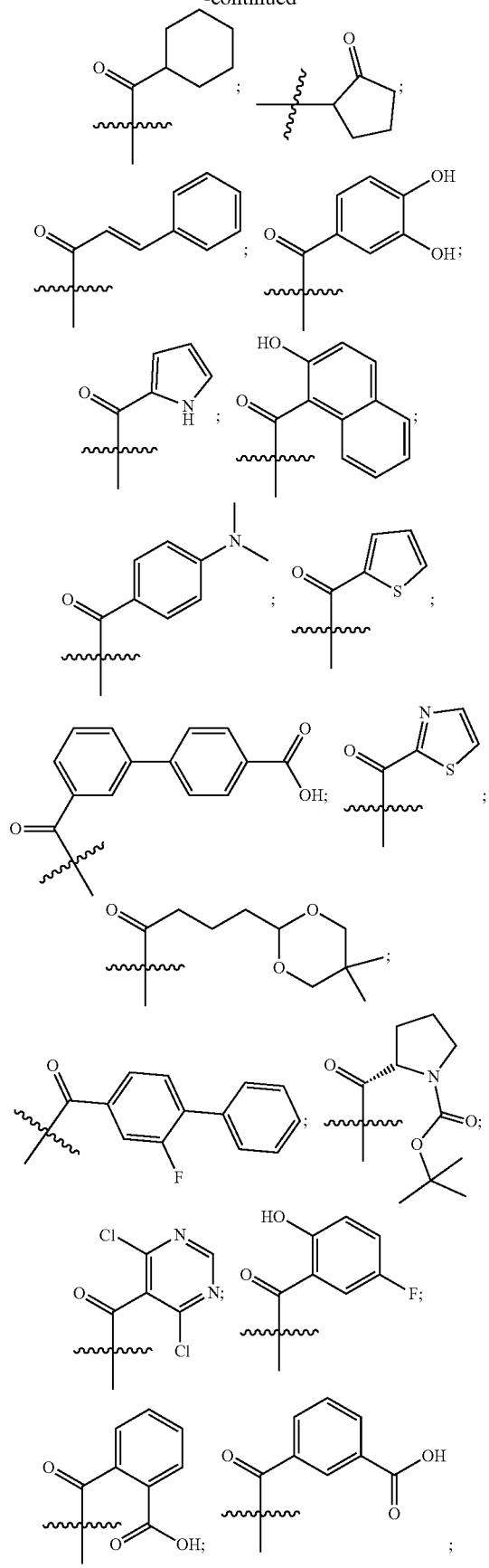
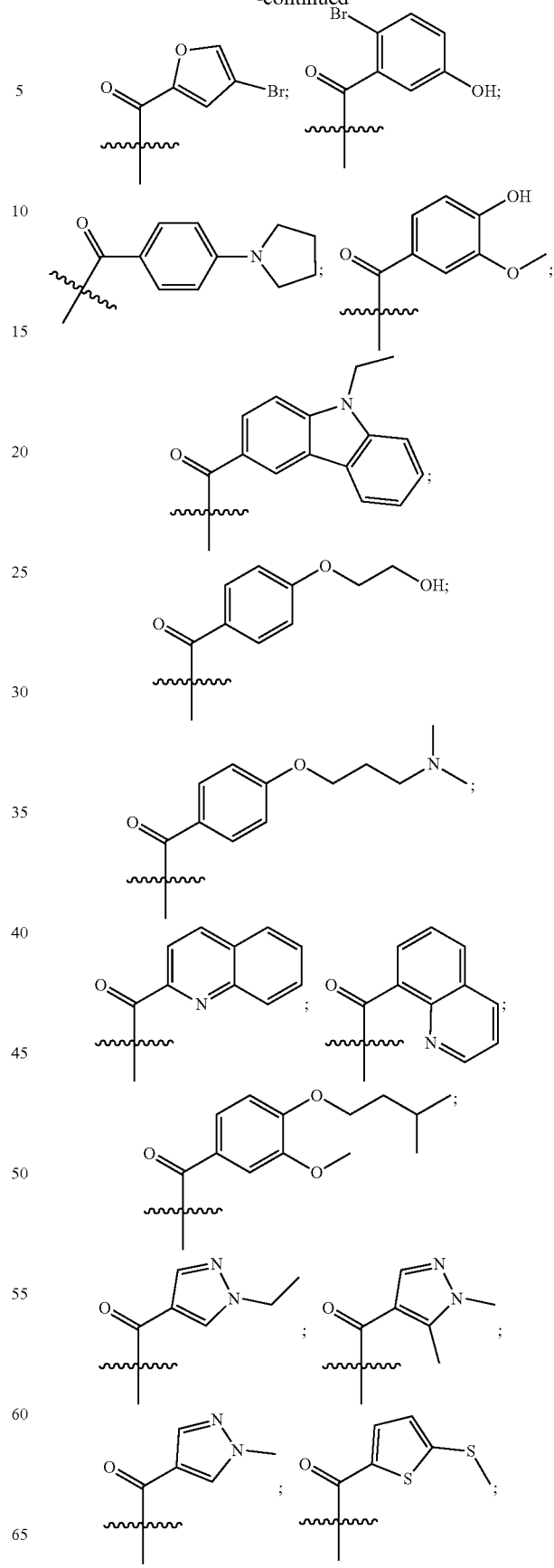

-continued
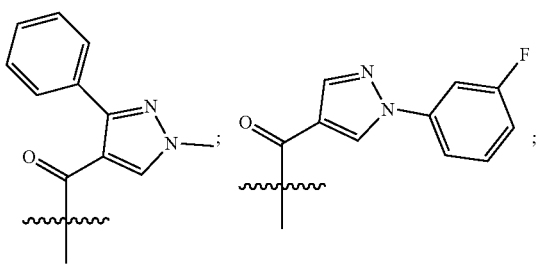
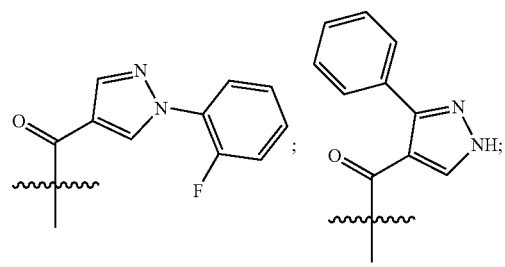
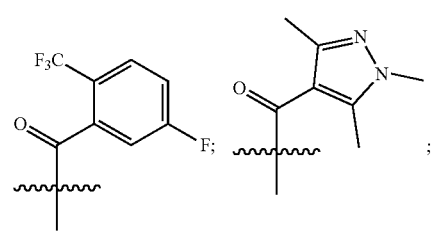
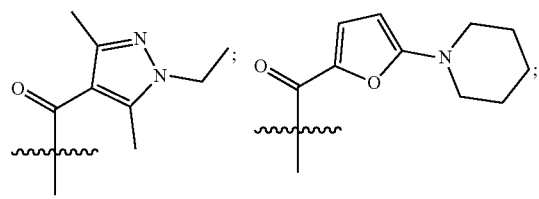
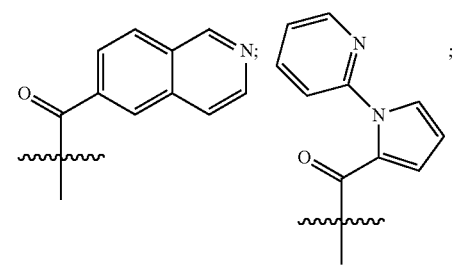
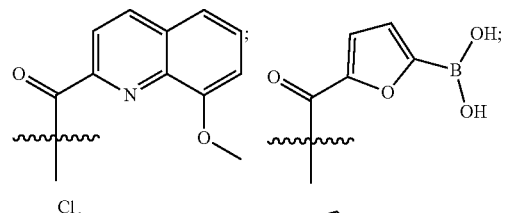
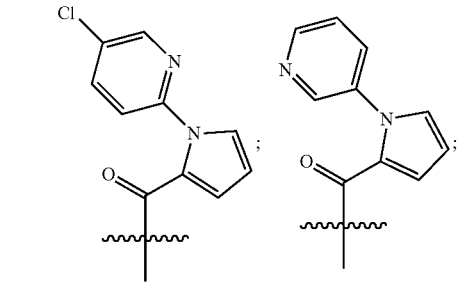
-continued
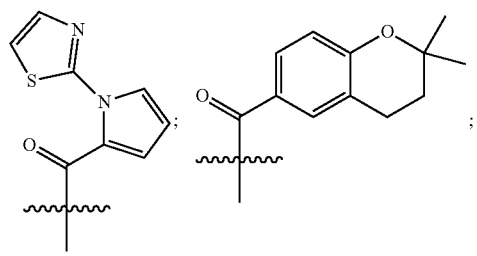
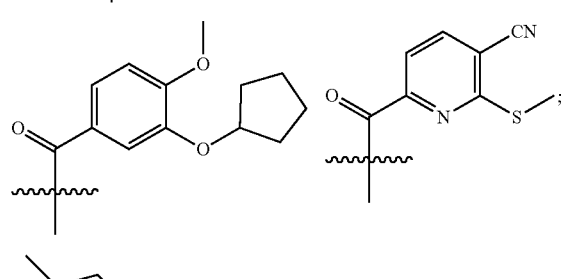
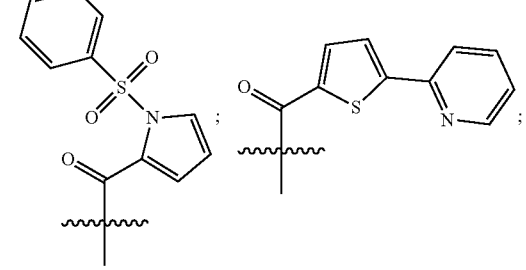
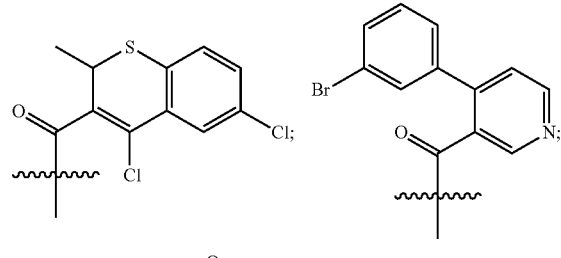
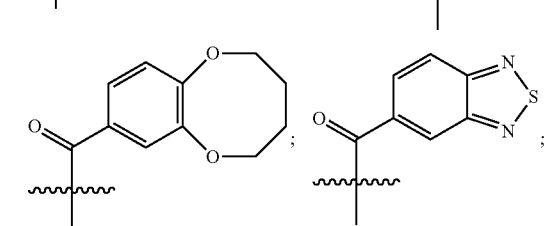
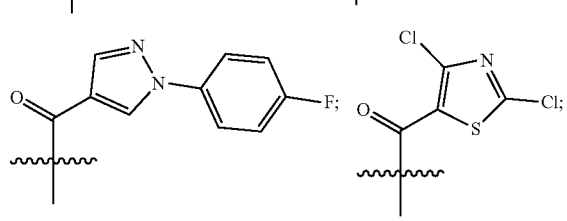
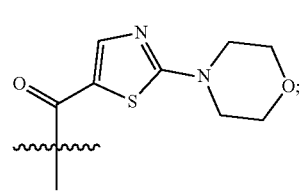

-continued
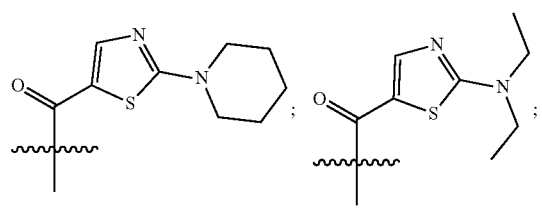
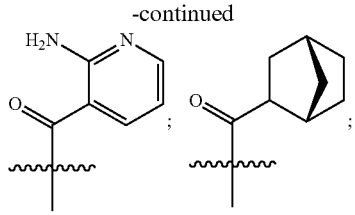
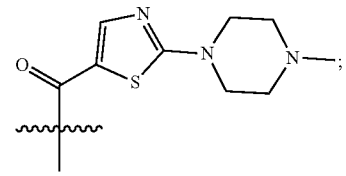
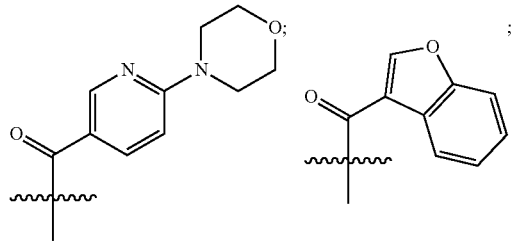
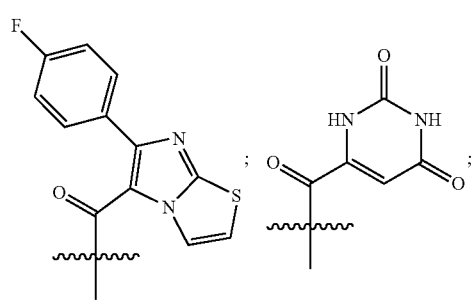
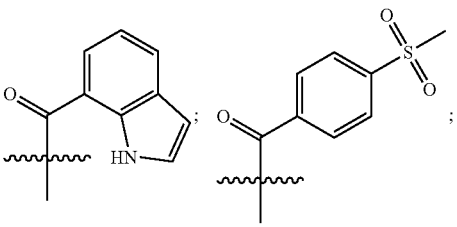
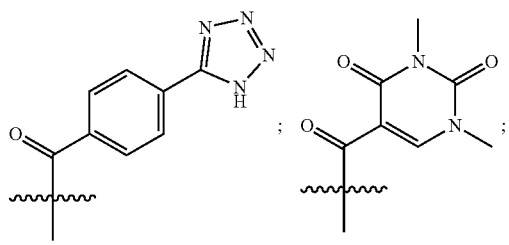
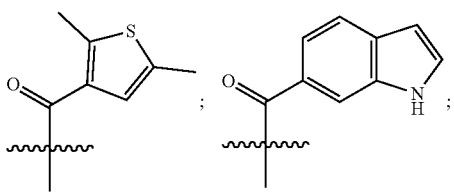
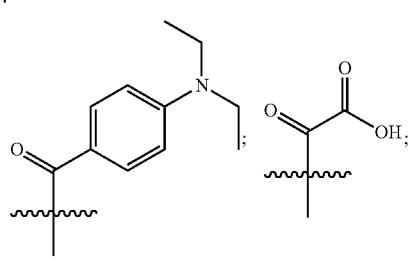
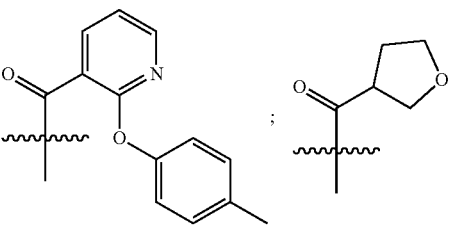
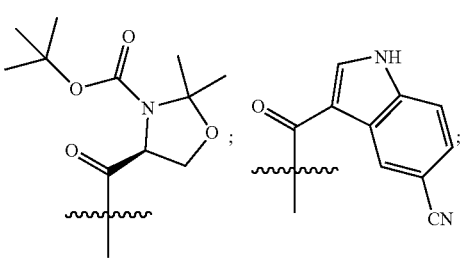
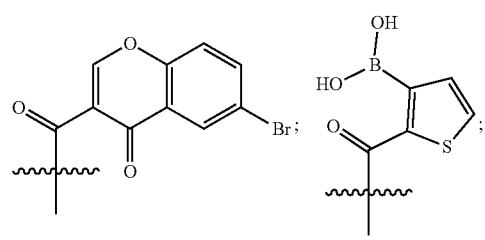
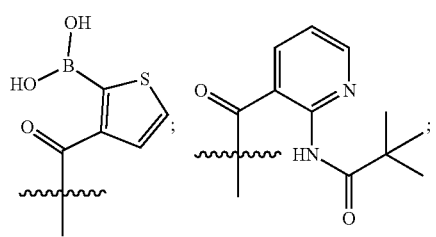
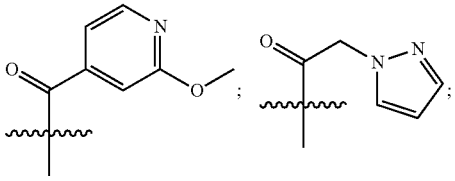

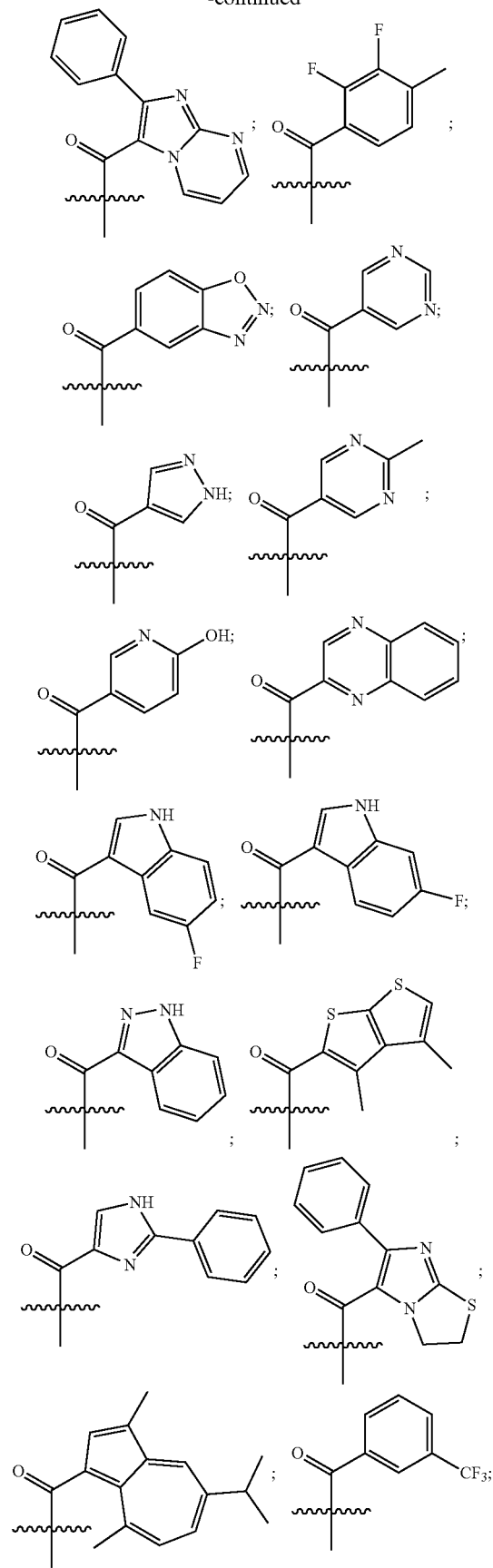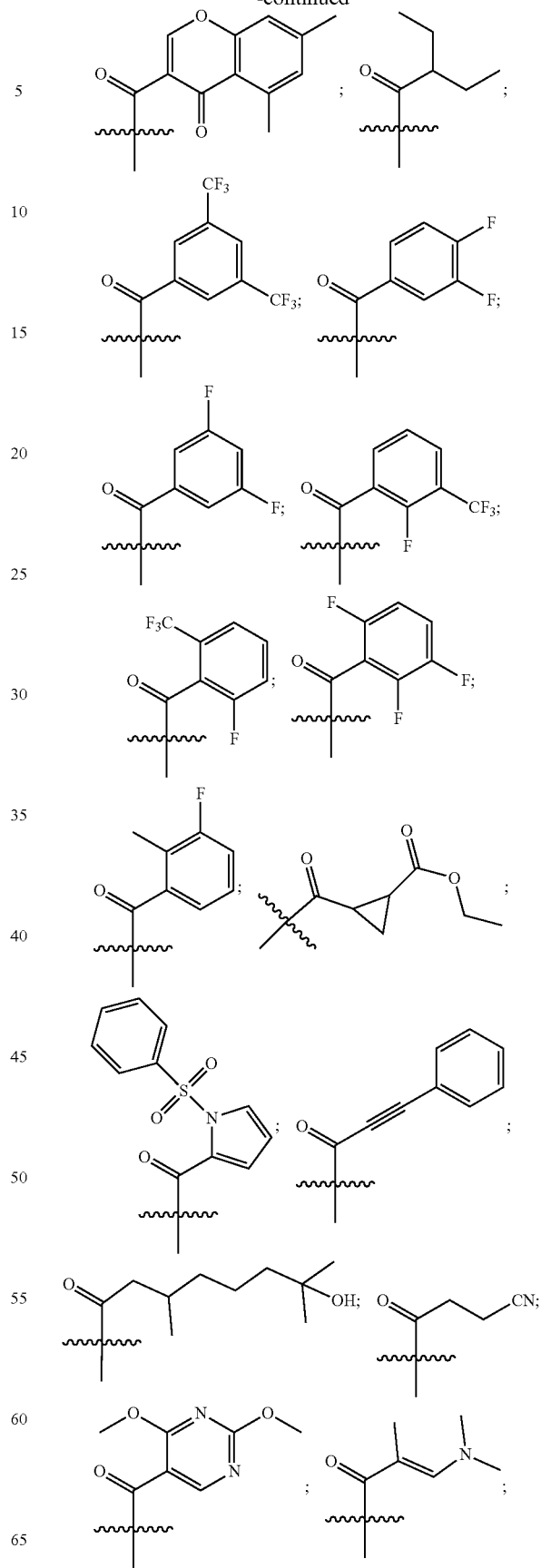

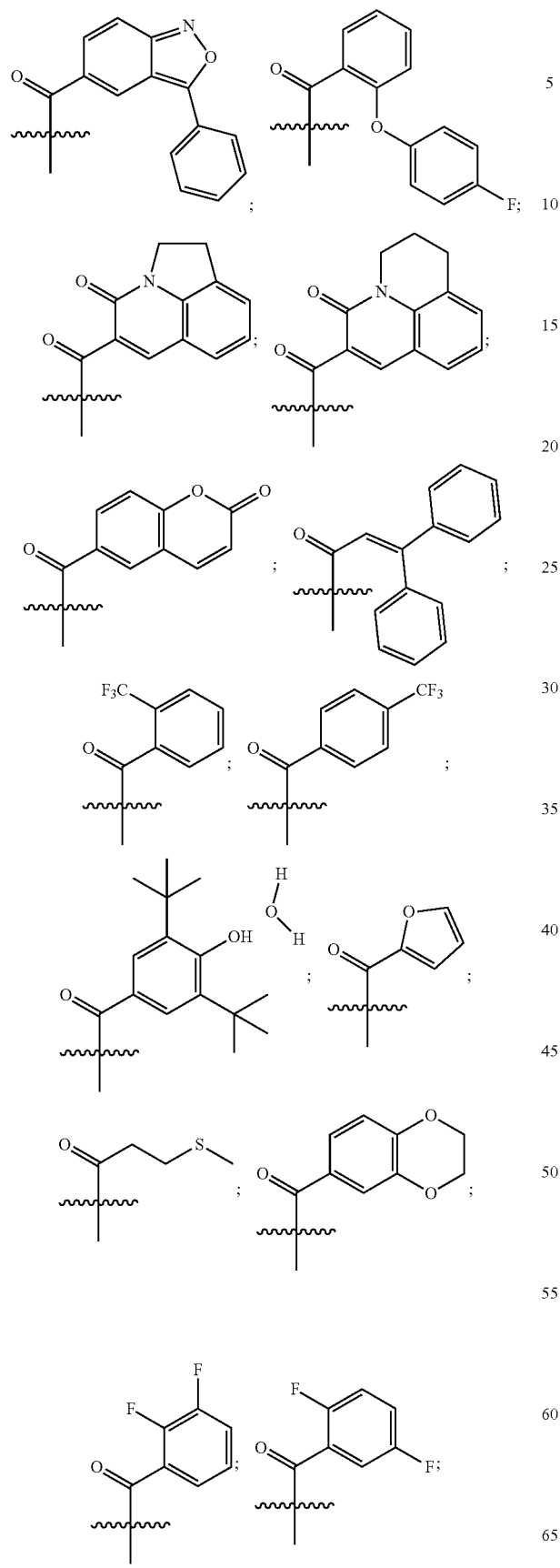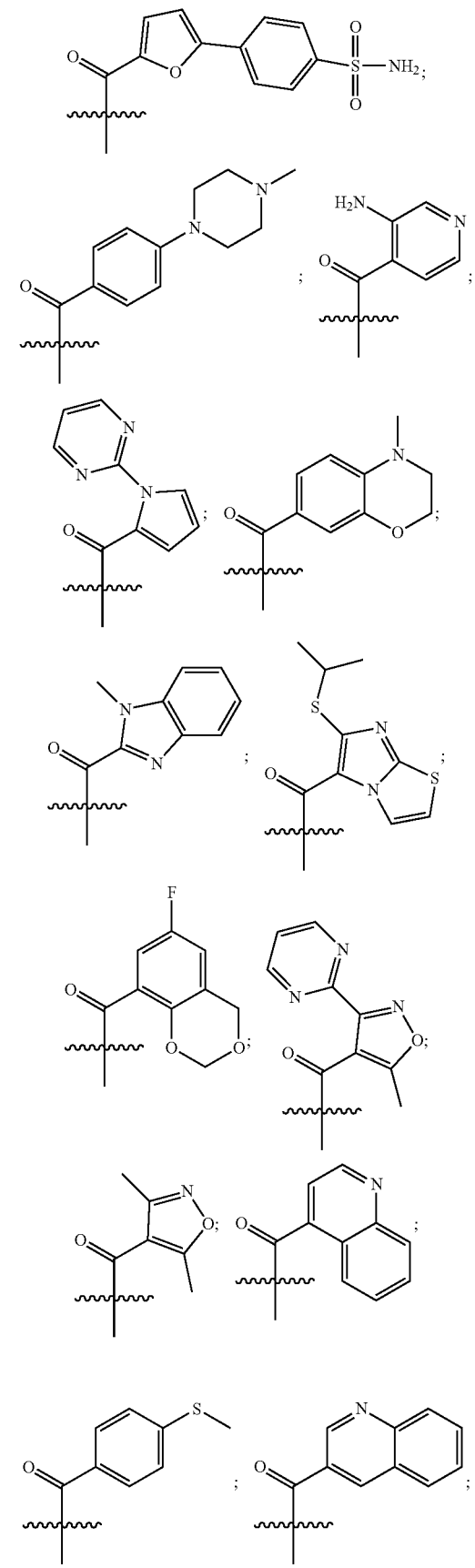

83
-continued
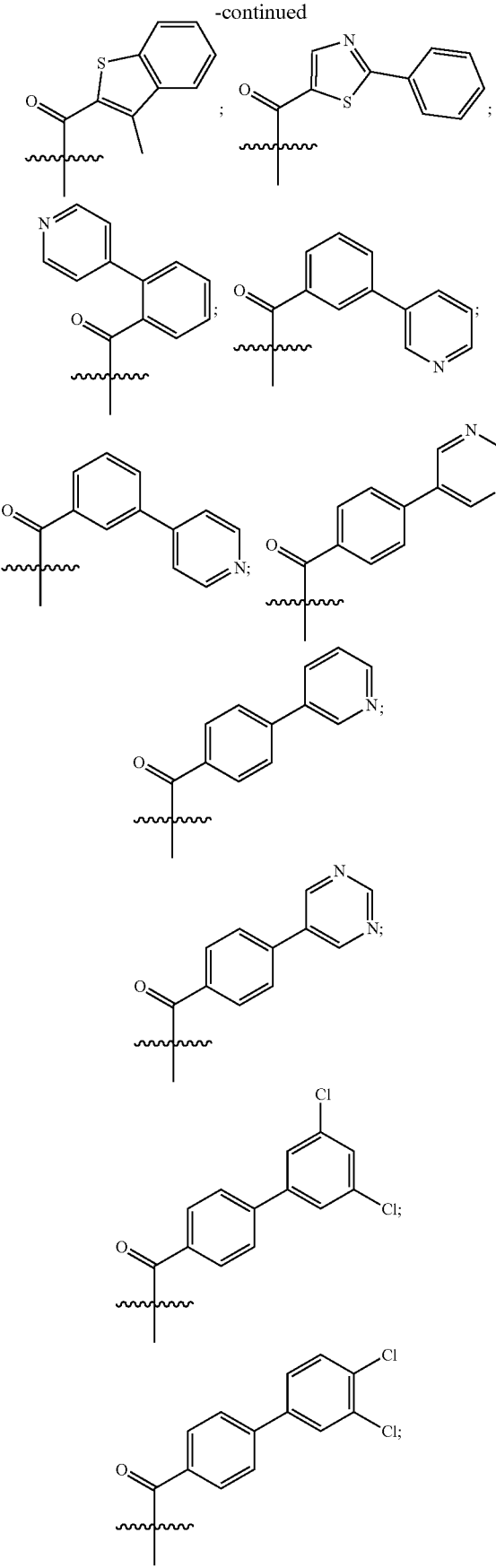
84
-continued
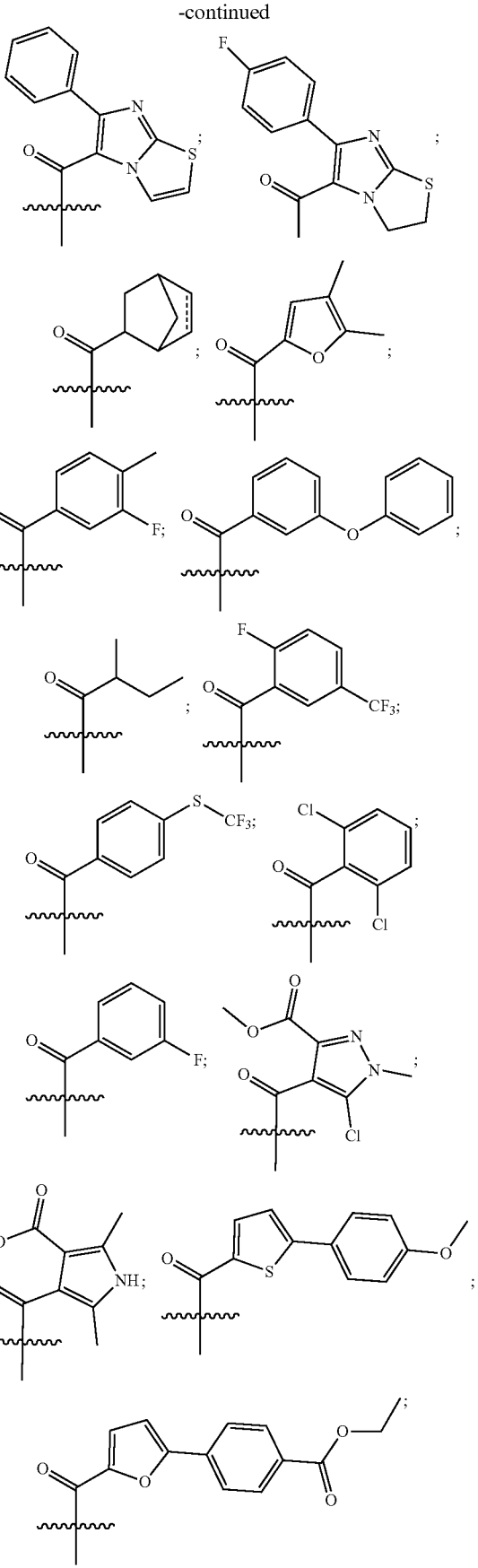

-continued
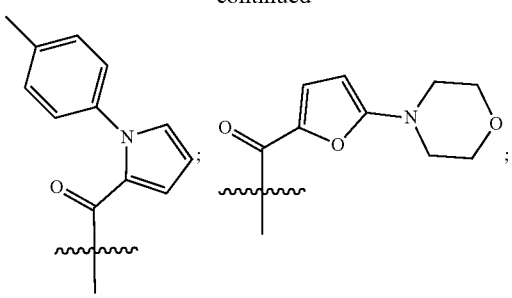
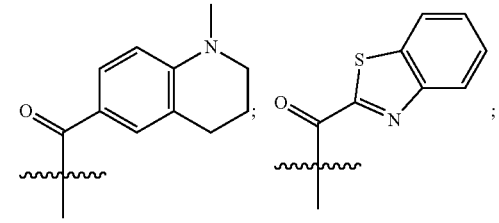
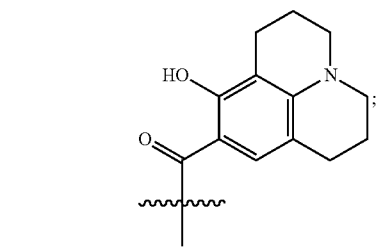
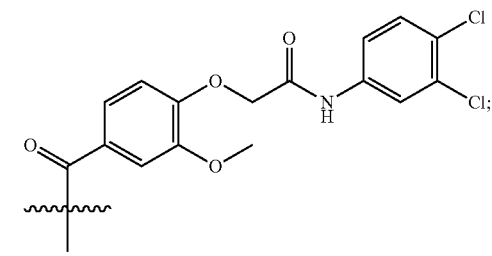
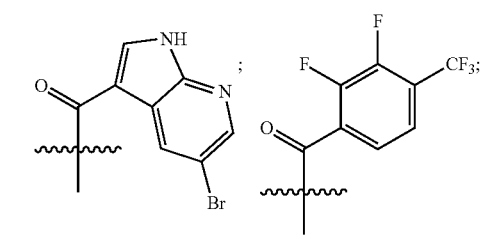
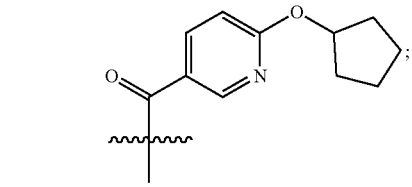
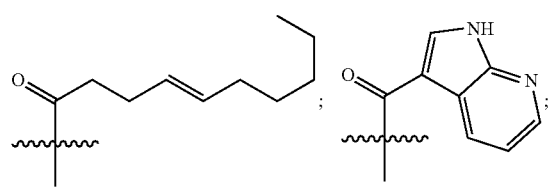
-continued
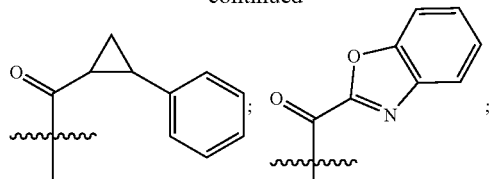
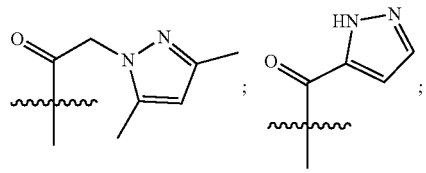
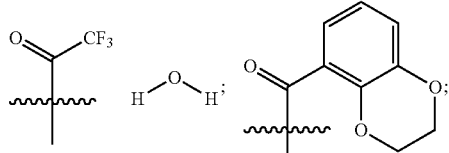
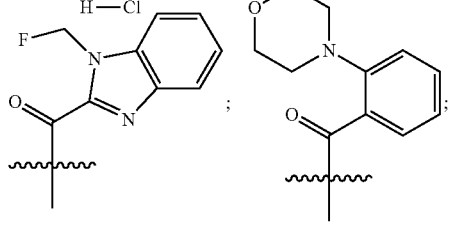
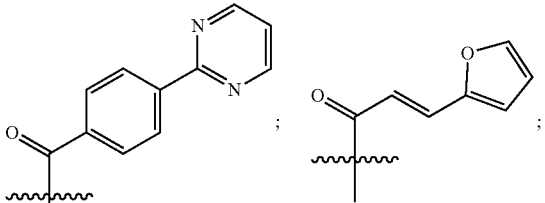
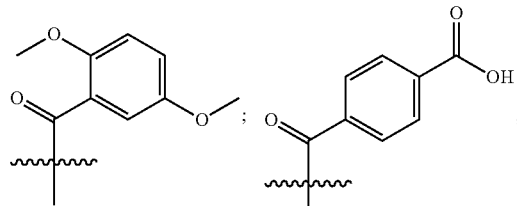
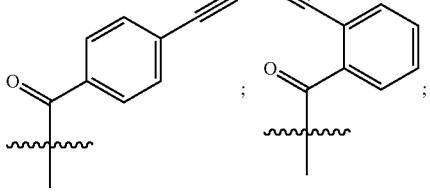
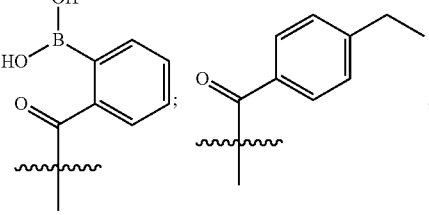

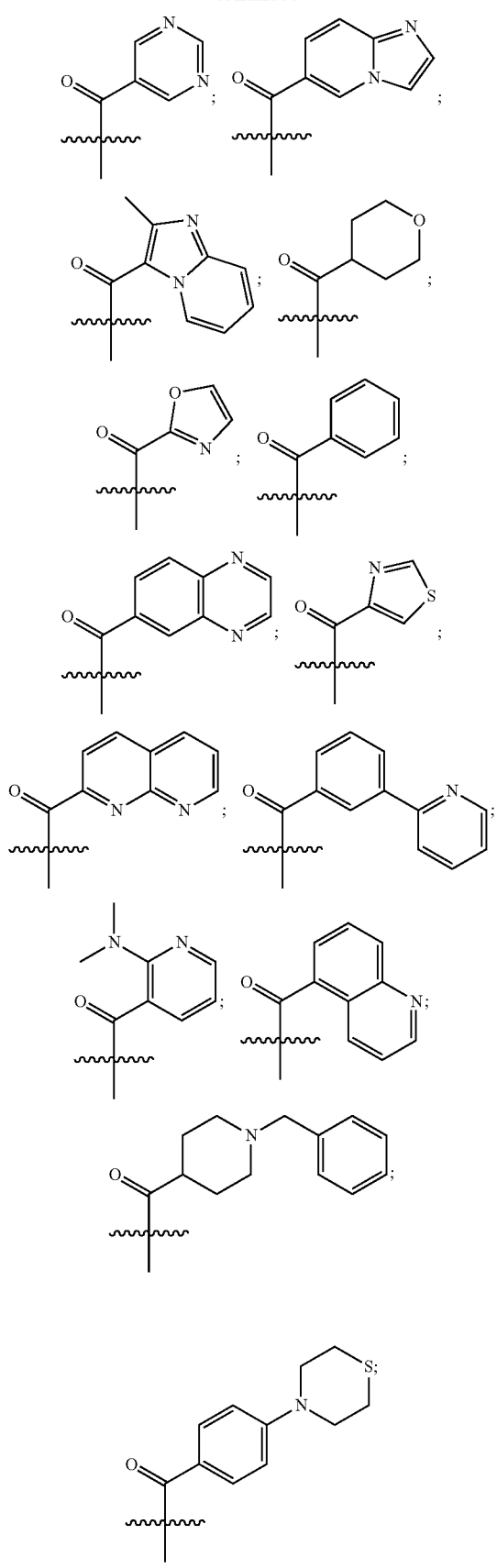
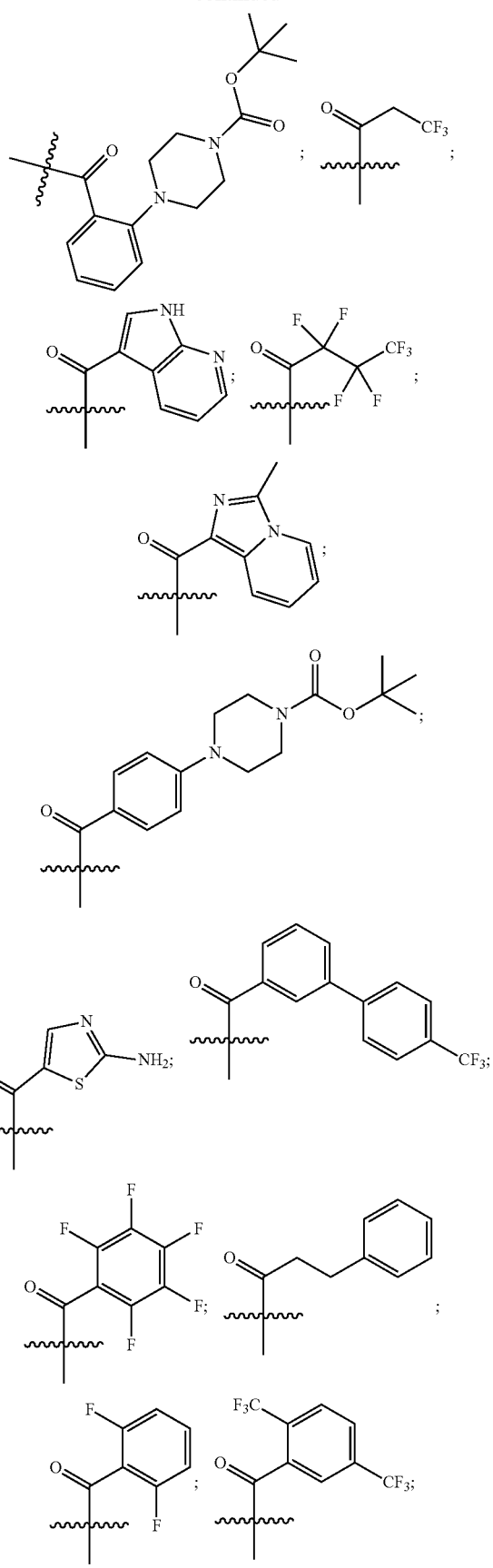

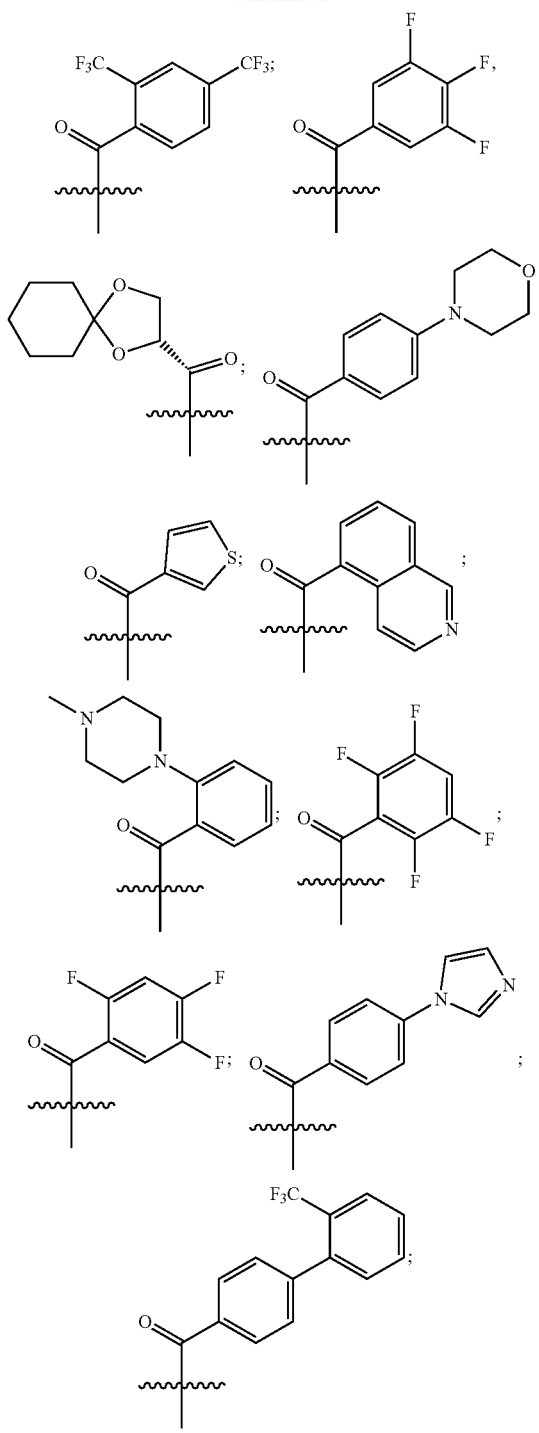
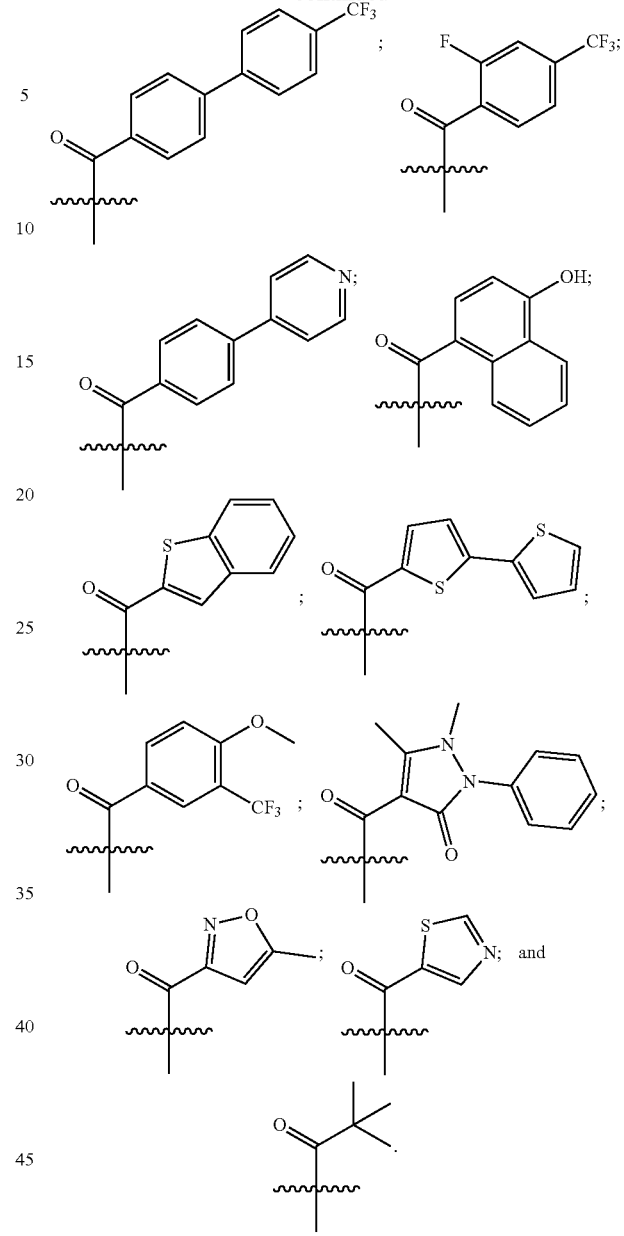
4. A pharmaceutical composition comprising the compound of claim 1, or a pharmaceutically acceptable salt or ester thereof, and a pharmaceutically acceptable carrier.
5. A pharmaceutical composition comprising the compound of claim 3, or a pharmaceutically acceptable salt or ester thereof, and a pharmaceutically acceptable carrier.
* * * * *